US011707531B2

(12) United States Patent
Iyer

(10) Patent No.: US 11,707,531 B2
(45) Date of Patent: Jul. 25, 2023

(54) COMPOUNDS, COMPOSITIONS, AND METHODS FOR THE TREATMENT OF DISEASE

(71) Applicant: F-star Therapeutics, Inc., Cambridge (GB)

(72) Inventor: Radhakrishnan P. Iyer, Shrewsbury, MA (US)

(73) Assignee: F-star Therapeutics, Inc., Cambridge (GB)

( * ) Notice: Subject to any disclaimer, the term of this patent is extended or adjusted under 35 U.S.C. 154(b) by 400 days.

(21) Appl. No.: 16/646,509

(22) PCT Filed: Sep. 11, 2018

(86) PCT No.: PCT/US2018/050471
§ 371 (c)(1),
(2) Date: Mar. 11, 2020

(87) PCT Pub. No.: WO2019/051489
PCT Pub. Date: Mar. 14, 2019

(65) Prior Publication Data
US 2020/0268899 A1    Aug. 27, 2020

Related U.S. Application Data

(60) Provisional application No. 62/649,263, filed on Mar. 28, 2018, provisional application No. 62/556,689, filed on Sep. 11, 2017.

(51) Int. Cl.
*A61K 47/68*    (2017.01)
*A61K 47/64*    (2017.01)
*A61K 47/54*    (2017.01)
*C07H 21/04*    (2006.01)

(52) U.S. Cl.
CPC ........ *A61K 47/6803* (2017.08); *A61K 47/549* (2017.08); *A61K 47/64* (2017.08); *C07H 21/04* (2013.01)

(58) Field of Classification Search
CPC .. A61K 47/6803; A61K 47/64; A61K 47/549; C07H 21/04
USPC ...................................................... 424/181.1
See application file for complete search history.

(56) References Cited

U.S. PATENT DOCUMENTS

| 5,547,941 | A  | 8/1996  | Battistini et al. |
| 7,592,326 | B2 | 9/2009  | Karaolis |
| 7,709,458 | B2 | 5/2010  | Karaolis et al. |
| 8,450,293 | B2 | 5/2013  | Jones et al. |
| 2007/0149462 | A1* | 6/2007 | Iyer ............ C07H 19/20 536/26.13 |
| 2014/0220056 | A1 | 8/2014  | Shishido et al. |
| 2014/0329889 | A1 | 11/2014 | Vance et al. |
| 2015/0374816 | A1 | 12/2015 | Iyer |
| 2016/0362441 | A1 | 12/2016 | Vernejoul et al. |
| 2017/0158772 | A1 | 6/2017  | Thompson et al. |
| 2017/0233430 | A1 | 8/2017  | Adams et al. |
| 2020/0268899 | A1 | 8/2020  | Iyer |
| 2020/0270299 | A1 | 8/2020  | Iyer et al. |

FOREIGN PATENT DOCUMENTS

| CN | 102199183 B | 12/2013 |
| JP | 2009501800 A | 1/2009 |
| WO | WO-2007/011968 A2 | 1/2007 |
| WO | WO-2011/003025 A1 | 1/2011 |
| WO | WO-2013/185052 A1 | 12/2013 |
| WO | WO-2014/093936 A1 | 6/2014 |
| WO | WO-2014/189805 A1 | 11/2014 |
| WO | WO-2015/057699 A2 | 4/2015 |
| WO | WO-2015/095755 A1 | 6/2015 |
| WO | WO-2015/185565 A1 | 12/2015 |
| WO | WO-2016/040684 A1 | 3/2016 |
| WO | WO-2016/096174 A1 | 6/2016 |
| WO | WO-2016.096577 A1 | 6/2016 |
| WO | WO-2016/120305 A1 | 8/2016 |
| WO | WO-2016/145102 A1 | 9/2016 |
| WO | WO-2017/009829 A1 | 1/2017 |
| WO | WO-2017/027645 A1 | 2/2017 |
| WO | WO-2017/027646 A1 | 2/2017 |
| WO | WO-2017/075477 A1 | 5/2017 |
| WO | WO-2017/093933 A1 | 6/2017 |
| WO | WO-2017/096963 A1 | 6/2017 |
| WO | WO 2017/100305  * | 6/2017 |
| WO | WO-2017/106740 A1 | 6/2017 |
| WO | WO-2017/123657 A1 | 7/2017 |
| WO | WO-2017/123669 A1 | 7/2017 |
| WO | WO-2017/151922 A1 | 9/2017 |
| WO | WO-2018/009466 A1 | 1/2018 |
| WO | WO-2018/045204 A1 | 3/2018 |
| WO | WO-2018/067423 A1 | 4/2018 |
| WO | WO-2018/100558 A2 | 6/2018 |

(Continued)

OTHER PUBLICATIONS

Chi et al., "Design and synthesis of specific inhibitors of the 3'-processing step of HIV-1 integrase," Nucleosides, Nucleotides and Nucleic Acids, 24(5-7):481-484 (2005).
Du et al., "Structure-efficacy Relationships of Immunostimulatory Activity of CpG-containing Oligodeoxynucleotides on Mouse Spleen Cells," Acta Pharm Sinic, 28(10): 1637-1644 (2007).
Extended European Search Report for EP Application No. 17824876.1 dated Jan. 3, 2020.
Fei et al., "Catalytic carbene transfer allows the direct customization of cyclic purine dinucleotides," Chem Comm, 50:8499-8502 (2014).
Gaffney et al., "One-flask syntheses of c-di-GMP and the [ R p, R p] and [ R p, S p] Thiophosphate analogues," Organic Letters, 12(14):3269-3271 (2010).

(Continued)

*Primary Examiner* — Yih-Horng Shiao
(74) *Attorney, Agent, or Firm* — Foley Hoag LLP; Dana M. Gordon; Alexander J. Chatterley

(57) ABSTRACT

Disclosed are compounds and compositions for the activation or induction of expression of a pattern recognition receptor (e.g., STING, RIG-I, MDA5), and methods of use thereof.

31 Claims, No Drawings

(56) References Cited

FOREIGN PATENT DOCUMENTS

| WO | WO-2018/118664 A1 | 6/2018 |
|---|---|---|
| WO | WO-2018/118665 A1 | 6/2018 |
| WO | WO-2018/140831 A2 | 8/2018 |
| WO | WO-2018/156625 A1 | 8/2018 |
| WO | WO-2018/198076 A1 | 11/2018 |
| WO | WO-2018/200812 A1 | 11/2018 |
| WO | WO-2018/208667 A1 | 11/2018 |
| WO | WO-2018/234805 A1 | 12/2018 |
| WO | WO-2018/234807 A1 | 12/2018 |
| WO | WO-2018/234808 A1 | 12/2018 |
| WO | WO-2019/051489 A1 | 3/2019 |
| WO | WO-2021/046426 A1 | 3/2021 |

OTHER PUBLICATIONS

Gura, "Systems for identifying New Drugs are Often Faulty," Cancer Models, Science 278(5340):1041-1042 (1997).
Hyodo et al., "Synthesis of cyclic bis(3'-5')diguanylic acid (c-di-GMP) analogs," Tetrahedron, 62(13):3089-3094 (2006).
International Search Report and Written Opinion for International Application No. PCT/US17/40882 dated Sep. 22, 2017.
International Search Report and Written Opinion for International Application No. PCT/US2018/50470 dated Jan. 18, 2019.
International Search Report and Written Opinion for International Application No. PCT/US2018/50471 dated Jan. 23, 2019.
Jeffrey et al., "Development and properties of 6-glucuronide linkers for monoclonal antibody-drug conuugates," Bioconjugate Chem, 17:831-840 (2006).
Jeffrey et al., "Minor groove binder antibodt conjugates employing a water soluble ß-glucuronide linker," Bioorganic & Medicinal Chemistry letters, 17:2278-2280 (2007).
Johnson et al., "Relationships between drug activity in NCI preclinical in vitro and in vivo models and early clinical trials," British Journal of Cancer, 84(10):1424-1431 (2001).
Libanova et al., "Cyclic di-nucleotides: New Era for Small Molecules as Adjuvants," Microb Biotechnol, 5(2): 168-176 (2012).
Pearce et al., "Failure modes in anticancer drug discovery and development," Cancer Drug Design and Discovery, Chapter 18:424-435 (2008).
Rytting, "Acute Leukemia," Merck Manual (Online Edition), 1-6 (2013).
Shanahan et al., "Differential analogue binding by two classes of c-di-GMP riboswitches," Journal of the American Chemical Society, 133(39): 15578-15592 (2011).
Shanahan et al., "Identification of c-di-GMP Derivatives Resistant to an EAL Domain Phosphodiesterase," Biochemistry, 52(2): 365-377 (2013).
Simone, Oncology: Introduction, Cecil Textbook of Medicine, 20th Edition, vol. 1, 1004-1010 (1996).
Smietana et al., "Efficient and simple solid-phase synthesis of short cyclic oligodeoxynucleotides bearing a phosphorothioate linkage," Angewandte Chemie, 41(19):3704-3707 (2002).
Smietana et al., "Solid-phase synthesis and screening of macrocyclic nucleotide-hybrid compounds targeted to hepatitis CNS5B," Chemistry—A European Journal, 10(1):173-181 (2004).
Tezuka et al., "Synthesis of 2'-modified cyclic bis(3'-5') diadenylic acids (c-di-AMPs) and their promotion of cell division in a freshwater green alga," Chemistry Letters, 41(12):1723-1725 (2012).
Zhao et al., "Thiophosphate analogs of c-Di-GMP: Impact on polymorphism," Nucleosides, Nucleotides and Nucleic Acids, 28(5):352-378 (2009).
Zhou et al., "Potent suppression of c-di-GMP synthesis via 1-site allosteric inhibition of diguanylate cyclases with 2'F-c-di-GMP," Bioorganic & Medicinal Chemistry, 21(14):4396-4404 (2013).
Kiburu et al., "A simple solid-phase synthesis of the ubiquitous bacterial signaling molecule, c-di-GMP and analogues", Molecular BioSystems, 4: 518-520 (2008).
International Search Report and Written Opinion for International Application No. PCT/US2020/049513 dated Dec. 17, 2020.
U.S. Appl. No. 16/646,504, Pending.

* cited by examiner

COMPOUNDS, COMPOSITIONS, AND METHODS FOR THE TREATMENT OF DISEASE

RELATED APPLICATIONS

This application is a § 371 (c) National Stage of PCT/US2018/050471, filed Sep. 11, 2018; which claims the benefit of priority to U.S. provisional patent application Nos. 62/649,263, filed Mar. 28, 2018; and 62/556,689, filed Sep. 11, 2017.

FIELD OF DISCLOSURE

Disclosed are compounds that activate in a host in a targeted manner the innate immune defense system and induce expression of pattern recognition receptors, which compounds are via a linker covalently bonded to or suitable for covalent bonding to a second active agent (e.g., an antibody). Also disclosed are compositions, comprising such compounds, and methods of using them for the treatment of a microbial infection or a proliferative disease (e.g., cancer).

BACKGROUND OF DISCLOSURE

Antibody Drug Conjugates (ADCs) are monoclonal antibodies (mAbs) attached to biologically active drugs by chemical linkers with labile bonds (Lu, *J. Int. J Mol. Sci.* (2016) 17:561-583; Perez, H. *Drug Discov. Today* (2013) 00:1-13; Jain, N. *Pharm. Res.* (2015) 323526-3540). By combining the unique targeting capabilities of mAbs with the cancer-killing ability of cytotoxic drugs, ADCs allow sensitive discrimination between healthy and diseased tissue. Accordingly, ADCs represent an important class of biopharmaceutical drugs designed to act as a targeted therapy for the treatment of subjects with various disease states (Ducry, L. *Bioconjugate Chemistry* (2010) 21:5-13)

ADCs are comprised of a drug like small molecule, covalently linked to an antibody. The antibody represents a targeting mechanism tuned to a specific site of action. Upon reaching the site, the ADC is designed to release a small molecule, the drug, allowing it to perform its designed function in a targeted manner, as opposed to diffusing systemically through the entire body of the subject. This targeted approach allows for treatment with drugs that would otherwise require doses so high as to be toxic when administered systemically.

A key feature of the innate immune system is the recognition and elimination of foreign substances. Identification of these pathogenic invaders occurs through host recognition of evolutionarily conserved microbial structures known as pathogen-associated molecular patterns (PAMPs) (Jensen, S. and Thomsen, A. R. *J Virol* (2012) 86:2900-2910). Host recognition may occur by multiple pathways, such as activation of pattern recognition receptors (PRRs), which ultimately lead to downstream signaling events and culminate in the mounting of an immune response.

To date, several PRRs have been identified that serve as sensors of pathogenic infection. For example, the retinoic acid-inducible gene-I (RIG-I) protein is a RNA helicase that also functions as a sensor of microbial-derived RNA. RIG-I is important factor in host recognition of RNA viruses from a variety of different viral families, including Flaviviridae (e.g., West Nile virus, Hepatitis C virus, Japanese encephalitis virus, Dengue virus), Paramyxoviridae (e.g., Sendai virus, Newcastle disease virus, Respiratory syncytial virus, Measles virus), Rhabdoviridae (e.g., Rabies virus), Orthomvxoviridae (e.g., influenza A virus, influenza B virus), and Arenaviridae (e.g., Lassa virus). Stimulator of interferon genes (STING) is a cytoplasmic adaptor protein that activates the TBK1-IRF3 signaling complex, resulting in induction of type I interferons (IFN-β and IFN-α) and other immune pathway proteins. Other PRRs also play a role in sensing microbial-derived nucleic acids, including NOD2, LGP2, MDA5, and a number of Toll-like receptors (TLRs) expressed on the cell surface and within endosomal compartments.

A shortcoming of many current antiviral therapies relates to the emergence of drug resistant variants that occurs upon extended use. In addition, many available treatments require persistent and long-term therapy, which often results in unwanted side effects and the risk of relapse upon conclusion of treatment. Further, many viruses can be subdivided into different genotypes, and certain drugs developed against one genotype may not be active against other genotypes. In contrast, the use of small molecule mimics of viral-derived RNA capable of PRR induction provides an alternate approach to the treatment of viral infection, as these compounds may be agnostic to genotype, may possess both direct antiviral activity as well as the ability to activate the host immune response, and potentially limit the development of drug resistance and toxicity. As such, there exists a need for a new generation of therapies that induce expression of PRRs for use in the treatment of disease and as diagnostic tools.

In addition, RIG-I serves as a biomarker for the prediction of prognosis for certain types of cancer, such as hepatocellular carcinoma (Hou, J. et al, *Cancer Cell* (2014) 25:49-63). Recent publications have highlighted the importance of RIG-1 and STING as mediators of innate and adaptive immunity, and RIG-I and STING agonists have been recognized as immuno-oncology agents in cancer therapy (Li, X. Y. et al, *Mol Cell Oncol* (2014) 1:e968016; Woo, S. R. *Trends in Immunol* (2015) 36:250-256). In particular, RIG-I is involved in the regulation of basic cellular processes such as hematopoietic proliferation and differentiation, maintenance of leukemic stemness, and tumorigenesis of hepatocellular carcinoma, indicating that RIG-I performs an essential function as a tumor suppressor. Importantly, the STING pathway of cytosolic DNA sensing has been shown to play an important mechanistic role in innate immune sensing, driving type IIFN production in cancer and in the context of immune-oncology applications, including therapeutics and diagnostics.

SUMMARY OF DISCLOSURE

Cyclic dinucleotide compounds, compositions comprising cyclic dinucleotide compounds, and related methods of use are described herein.

In one aspect, the disclosure features a compound of Formula (I):

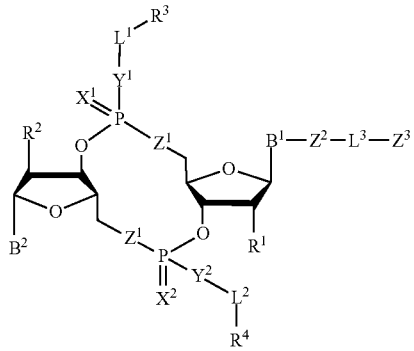

Formula (I)

or a pharmaceutically acceptable salt or stereoisomer thereof,
wherein:
each of $B^1$ and $B^2$ is independently a purinyl nucleobase or pyrimidinyl nucleobase;
each of $X^1$ and $X^2$ is independently O or S;
each of $Y^1$ and $Y^2$ is independently O, S, or $N(R^5)$;
each of $Z^1$ is independently O or S;
$Z^2$ is —O—, —$N(R^5)$—, —S—, —C(O)—, —C(O)N($R^5$)—, —OC(O)N($R^5$)—, —N($R^5$)C(O)O—, -aryl-, -heteroaryl-, —S(O)—, —S(O)$_2$—, —S(O)N(R')—, —S(O)$_2$N($R^5$)— or —N($R^5$)S(O)—;
$Z^3$ is hydrogen, heterocyclyl, heterocyclyl-$C_1$-$C_{20}$-alkylene-$Q^1$, —OH, —N($R^5$)$_2$, $SR^5$, —CHO, —C(O)N($R^5$)$_2$, —OC(O)N($R^5$)$_2$, —N($R^5$)C(O)O$R^5$, aryl, heteroaryl, —S(O)$R^5$, —S(O)$_2R^5$, —S(O)N($R^5$)$_2$, —S(O)$_2$N($R^5$)$_2$, —N($R^5$)S(O)$R^5$, —OSi($C_1$-$C_4$ alkyl)$_3$, or —C(O)$C_2$-$C_6$ alkenyl (e.g., —$C_2$-$C_4$ alkenyl);
$L^1$ is —$C_1$-$C_6$— alkylene (e.g., $C_1$-$C_3$ alkylene) or —$C_1$-$C_6$— heteroalkylene (e.g., —$C_1$-$C_3$ heteroalkylene);
$L^2$ is absent, —$C_1$-$C_6$— alkylene (e.g., —$C_1$-$C_3$— alkylene) or —$C_1$-$C_6$— heteroalkylene, wherein each alkylene and hetero alkylene is optionally substituted with one or more $R^6$;
$L^3$ is oligiopeptide-C(O)—, oligiopeptide-aryl-$C_1$-$C_6$-alkylene-, oligiopeptide-aryl-$C_1$-$C_6$-heteroalkylene, oligiopeptide-aryl-$C_1$-$C_6$-alklyene-C(O)—, oligiopeptide-$C_1$-$C_6$-alkylene-C(O)—, oligiopeptide-$C_1$-$C_6$-heteroalkylene-C(O)—, —$C_1$-$C_{40}$— alkylene (e.g., —$C_1$-$C_{20}$— alkylene), —$C_1$-$C_{40}$— heteroalkylene (e.g., —$C_1$-$C_{20}$— heteroalkyl), —$C_1$-$C_{40}$— alkenylene (e.g., —$C_2$-$C_{20}$— alkenylene), or —$C_1$-$C_{40}$-alkynylene (e.g., —$C_2$-$C_{20}$— alkynylene), wherein the oligopeptide is optionally substituted by one or more $R^{14}$;
Q is C(O), C(S), or $CH_2$;
each of $R^1$ and $R^2$ is independently hydrogen, halo, —CN, —$C_1$-$C_{20}$ alkyl (e.g., —$C_1$-$C_6$ alkyl), or $OR^7$;
each $R^3$ and $R^4$ is independently hydrogen, —$C_1$-$C_{20}$— alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$;
$R^5$ is hydrogen or —$C_1$-$C_{20}$ alkyl (e.g., —$C_1$-$C_6$ alkyl);

$R^6$ is halo, —CN, —$C_1$-$C_{20}$ alkyl (e.g., —$C_1$-$C_6$ alkyl), —$OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$;
$R^7$ is hydrogen, —$C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$;
each $R^8$ is independently —$C_1$-$C_{20}$ alkyl (e.g., —$C_1$-$C_6$ alkyl), —$C_1$-$C_{20}$ heteroalkyl, —C(O), —$C_1$-$C_{20}$ alkyl, —OC(O)—$C_1$-$C_{20}$ alkyl (e.g., —$C_1$-$C_6$ alkyl), —C(O)O—$C_1$-$C_{20}$ alkyl (e.g., —$C_1$-$C_6$ alkyl), —OC(O)O—$C_1$-$C_{20}$ alkyl (e.g., —$C_1$-$C_6$ alkyl), —C(O)N($R^5$)—$C_1$-$C_{20}$ alkyl (e.g., —$C_1$-$C_6$ alkyl), —N($R^5$)C(O)—$C_1$-$C_{20}$ alkyl (e.g., —$C_1$-$C_6$ alkyl), —OC(O)N($R^5$)—$C_1$-$C_{20}$ alkyl (e.g., —$C_1$-$C_6$ alkyl), —O-aryl, —O-heteroaryl, —C(O)-aryl, —C(O)-heteroaryl, —OC(O)-aryl, —C(O)O-aryl, —OC(O)-heteroaryl, —C(O)O-heteroaryl, —C(O)O-aryl, —C(O)O-heteroaryl, —C(O)N($R^5$)-aryl, —C(O)N($R^5$)-heteroaryl, —N($R^5$)C(O)-aryl, —N($R^5$)$_2$C(O)-aryl, or —N($R^5$)C(O)-heteroaryl, —S(O)$_2$N($R^5$)-aryl, wherein each alkyl, heteroalkyl, aryl, and heteroaryl is optionally substituted by one or more $R^9$;
each $R^9$ is independently —$C_1$-$C_{20}$ alkyl, —O—$C_1$-$C_{20}$ alkyl, —$C_1$-$C_{20}$ heteroalkyl, halo, —CN, —OH, oxo, aryl, heteroaryl, —O-aryl, or —O-heteroaryl;
$Q^1$ is C(O), C(S), or $CH_2$; and
each $R^{16}$ is independently, —$C_1$-$C_{20}$ alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), C(O)N($R^4$)$_2$ cycloalkyl, heterocyclyl, aryl, or heteroaryl.

In some embodiments, the compound is a compound of Formula (I-a), (I-b), (I-c), or (I-d):

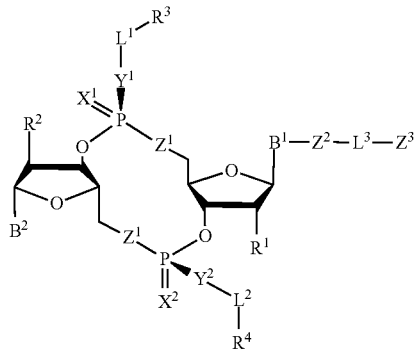

Formula (I-a)

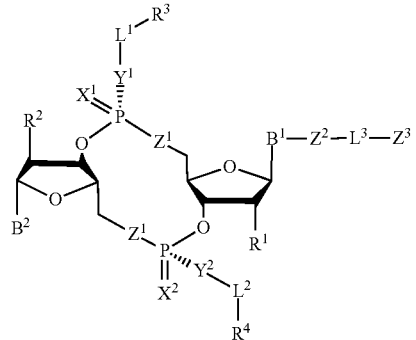

Formula (I-b)

Formula (I-c)
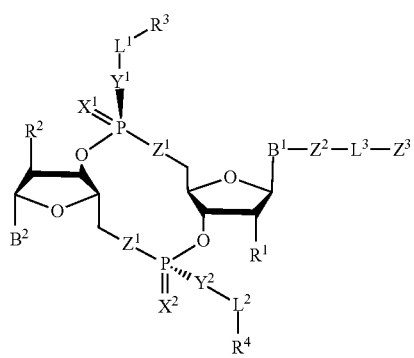
Formula (I-d)
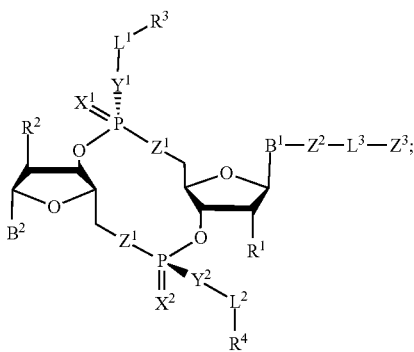
or a pharmaceutically acceptable salt or stereoisomer thereof.
In some embodiments, the compound is a compound of Formula (I-e), (I-f), (I-g), (I-H) or (I-i):
Formula (I-e)
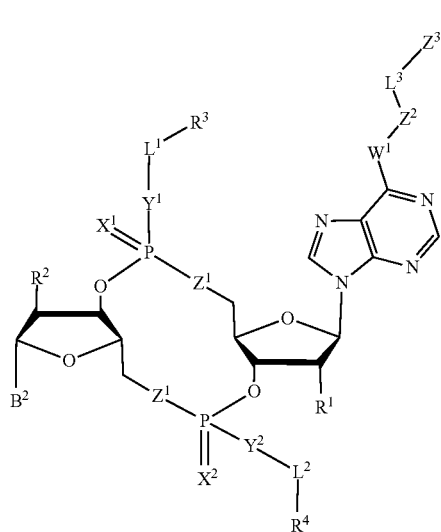
Formula (I-f)
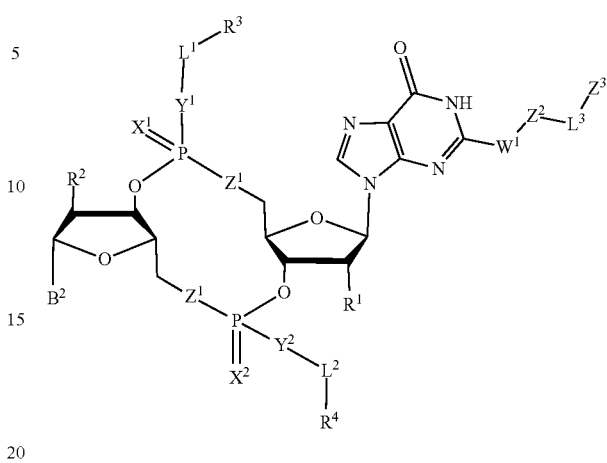
Formula (I-g)
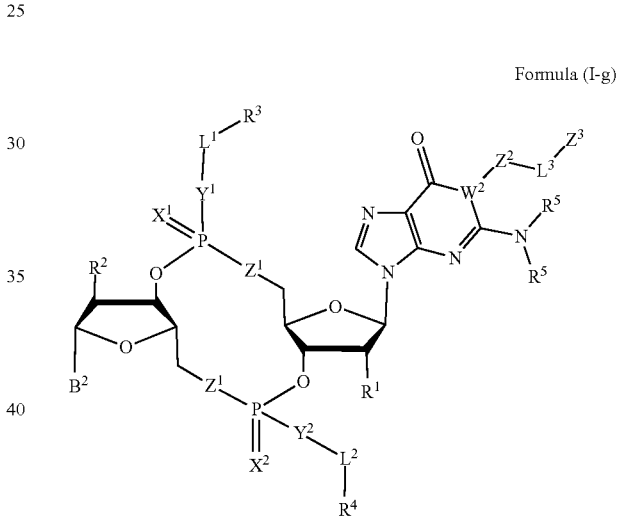
Formula (I-h)
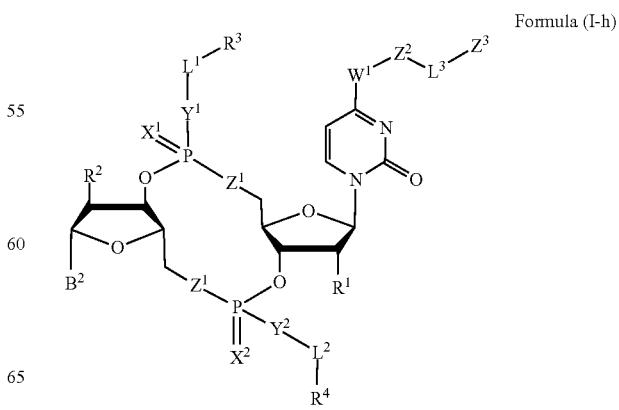

-continued

Formula (I-i)

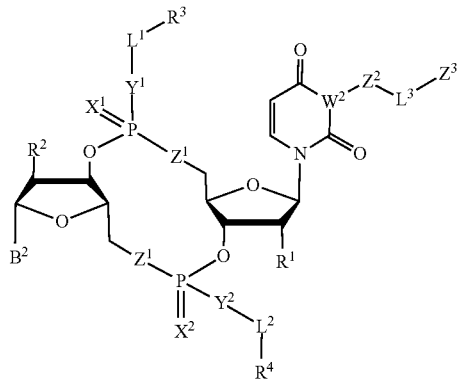

Formula (I-j)

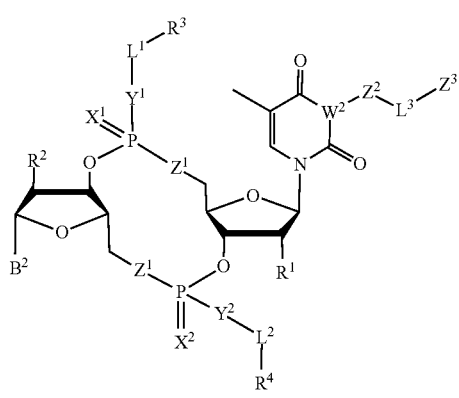

or a pharmaceutically acceptable salt or stereoisomer thereof, wherein:
$W^1$ is $N(R^5)$, —O—CH; and
$W^2$ is N or CH.

In one aspect, the disclosure features a compound of Formula (II):

Formula (II)

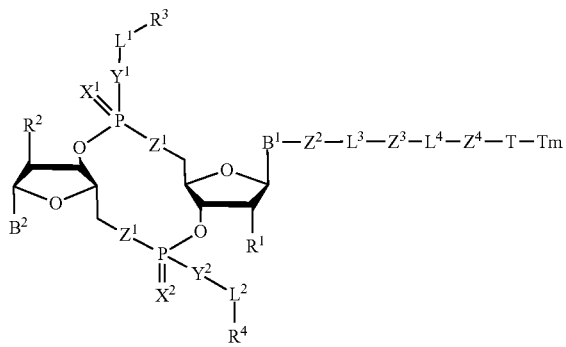

or a pharmaceutically acceptable salt or stereoisomer thereof,
wherein:
Tm is a targeting moiety;
each of $B^1$ and $B^2$ is independently a purinyl nucleobase or pyrimidinyl nucleobase;
each of $X^1$ and $X^2$ is independently O or S;
each of $Y^1$ and $Y^2$ is independently O, S, or $N(R^5)$;
each of $Z^1$ is independently O or S;
$Z^2$ is —O—, —$N(R^5)$—, —S—, —C(O)—, —C(O)N($R^5$)—, —OC(O)N($R^5$)—, —N($R^5$)C(O)O—, -aryl-, -heteroaryl-, —S(O)—, —S(O)$_2$—, —S(O)N($R^5$)—, —S(O)$_2$N($R^5$)— or —N($R^5$)S(O)—;
$Z^3$ is absent, hydrogen, heterocyclyl, heterocyclyl-$C_1$-$C_{20}$-alkylene-$Q^1$, —OH, —N($R^5$)$_2$, $SR^5$, —CHO, —C(O)N($R^5$)$_2$, —OC(O)N($R^5$)$_2$, —N($R^5$)C(O)OR$^5$, aryl, heteroaryl, —S(O)R$^5$, —S(O)$_2$R$^5$, —S(O)N($R^5$)$_2$, —S(O)$_2$N($R^5$)$_2$, —N($R^5$)S(O)R$^5$, —OSi($C_1$-$C_4$ alkyl)$_3$, or —C(O)$C_2$-$C_6$ alkenyl (e.g., —$C_2$-$C_4$ alkenyl);
$Z^4$ is a self-immolative group or absent;
T is a absent or spacer group;
each $L^1$ and $L^2$ is absent, —$C_1$-$C_6$— alkylene (e.g., —$C_1$-$C_3$— alkylene) or —$C_1$-$C_6$-heteroalkylene, wherein each alkylene and heteroalkyl is optionally substituted with one or more $R^6$;
$L^3$ is oligiopeptide-C(O)—, oligiopeptide-aryl-$C_1$-$C_6$-alkylene-, oligiopeptide-aryl-$C_1$-$C_6$-alklyene-C(O)—, oligiopeptide-aryl-$C_1$-$C_6$-heteroalkylene, oligiopeptide-$C_1$-$C_6$-alkylene-C(O)—, oligiopeptide-$C_1$-$C_6$-heteroalkylene-C(O)—, —$C_1$-$C_{40}$-alkylene (e.g., —$C_1$-$C_{20}$ alkylene), —$C_1$-$C_{40}$— heteroalkylene (e.g., —$C_1$-$C_{20}$-heteroalkyl), —$C_1$-$C_{40}$— alkenylene (e.g., —$C_2$-$C_{20}$— alkenylene), or —$C_1$-$C_{40}$-alkynylene (e.g., —$C_2$-$C_{20}$— alkynylene), wherein the oligopeptide is optionally substituted by one or more $R^{14}$;
$L^4$ is absent or a linker connecting $Z^3$ and $Z^4$;
$Q^1$ is C(O), C(S), or CH$_2$;
each of $R^1$ and $R^2$ is independently hydrogen, halo, —CN, —$C_1$-$C_{20}$ alkyl (e.g., $C_1$-$C_6$ alkyl), or —OR;
each $R^3$ and $R^4$ is independently hydrogen, —$C_1$-$C_{20}$— alkyl (e.g., —$C_1$-$C_6$ alkyl), —$C_1$-$C_{20}$ heteroalkyl (e.g., —$C_1$-$C_6$ heteroalkyl). —OC(O)O$C_1$-$C_{20}$ alkyl (e.g., —$C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$;
$R^5$ is hydrogen or —$C_1$-$C_{20}$ alkyl (e.g., —$C_1$-$C_6$ alkyl);
$R^6$ is halo, —CN, —$C_1$-$C_{20}$ alkyl (e.g., —$C_1$-$C_6$ alkyl), —OR$^7$, oxo, cycloalkyl, heterocyclyl, aryl, or heteroaryl, wherein each alkyl, cycloalkyl, heterocyclyl, aryl, and heteroaryl is optionally substituted with one or more $R^9$;
$R^7$ is hydrogen, —$C_1$-$C_{20}$ alkyl (e.g., —$C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$;
each $R^8$ is independently —$C_1$-$C_{20}$ alkyl (e.g., —$C_1$-$C_6$ alkyl), —$C_1$-$C_{20}$ heteroalkyl, —C(O)—$C_1$-$C_{20}$ alkyl, —OC(O)—$C_1$-$C_{20}$ alkyl (e.g., —$C_1$-$C_6$ alkyl), —C(O)O—$C_1$-$C_{20}$ alkyl (e.g., —$C_1$-$C_6$ alkyl), —OC(O)O—$C_1$-$C_{20}$ alkyl (e.g., —$C_1$-$C_6$ alkyl), —C(O)N($R^5$)—$C_1$-$C_{20}$ alkyl (e.g., —$C_1$-$C_6$ alkyl), —N($R^5$)C(O)—$C_1$-$C_{20}$ alkyl (e.g., —$C_1$-$C_6$ alkyl), —OC(O)N($R^5$)—$C_1$-$C_{20}$ alkyl (e.g., —$C_1$-$C_6$ alkyl), —O-aryl, —O— heteroaryl, —C(O)-aryl, —C(O)-heteroaryl, —OC(O)-aryl, —C(O)O-aryl, —OC(O)— heteroaryl, —C(O)O-heteroaryl, —C(O)O-aryl, —C(O)O-heteroaryl, —C(O)N($R^5$)-aryl, —C(O)N($R^5$)-heteroaryl, —N($R^5$)C(O)-aryl, —N($R^5$)$_2$C(O)-aryl, or —N($R^5$)C(O)-heteroaryl, —S(O)$_2$N($R^5$)-aryl, wherein each alkyl, heteroalkyl, aryl, and heteroaryl is optionally substituted by one or more $R^9$;
each $R^9$ is independently —$C_1$-$C_{20}$ alkyl, —O—$C_1$-$C_{20}$ alkyl, —$C_1$-$C_{20}$ heteroalkyl, halo, —CN, —OH, oxo, aryl, heteroaryl, —O-aryl, or —O-heteroaryl; and
each $R^{16}$ is independently, —$C_1$-$C_{20}$ alkyl (e.g., —$C_1$-$C_6$ alkyl), —$C_1$-$C_{20}$ heteroalkyl (e.g., —$C_1$-$C_6$ heteroalkyl), —OC(O)OC$_1$-C$_{20}$ alkyl (e.g., —C$_1$-C$_6$ alkyl), C(O)N(R$^4$)$_2$ cycloalkyl, heterocyclyl, aryl, or heteroaryl.

In some embodiments, the compound is a compound of Formula (II-a), (II-b), (II-c), or (II-d):

Formula (II-a)
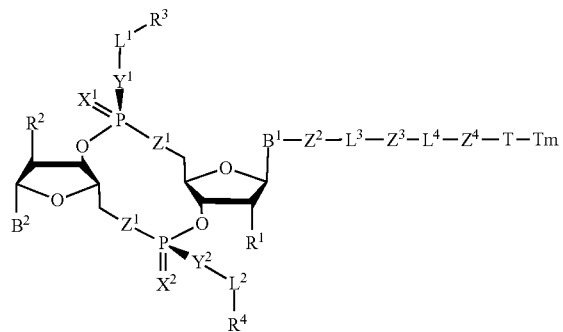

Formula (II-b)
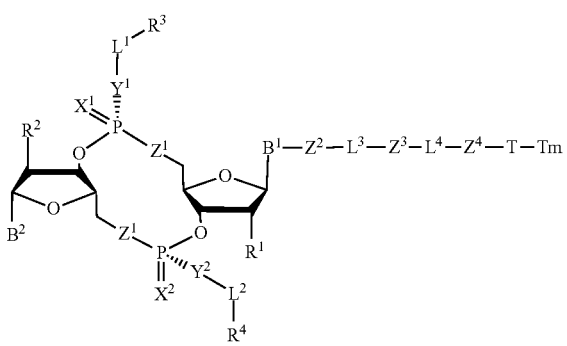

Formula (II-c)
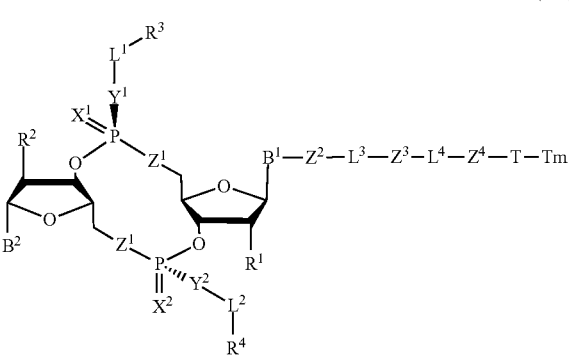

Formula (II-d)
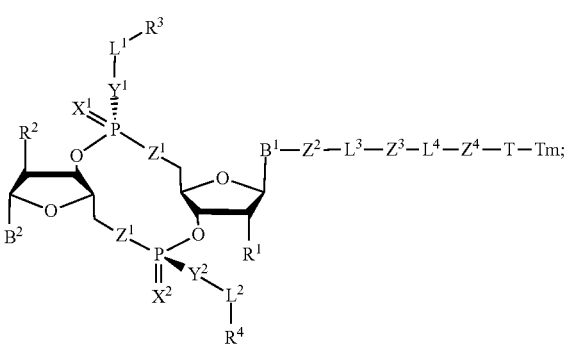

or a pharmaceutically acceptable salt or stereoisomer thereof.

In some embodiments, the compound is a compound of Formula (II-e), (II-f), (II-g), (II-h) or (II-i):

Formula (II-e)
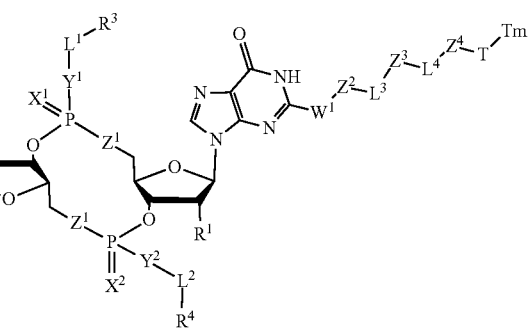

Formula (II-f)

Formula (II-g)
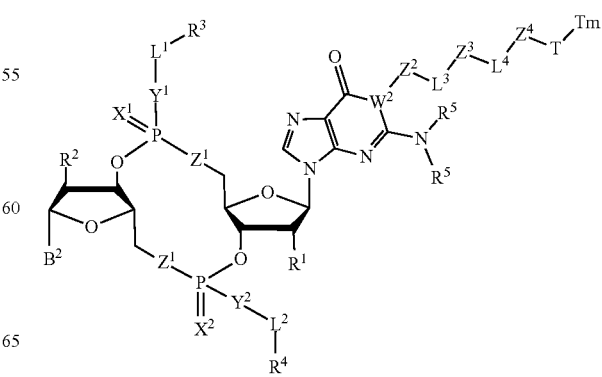

-continued

Formula (II-h)

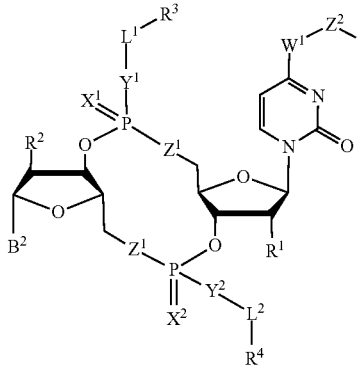

Formula (II-i)

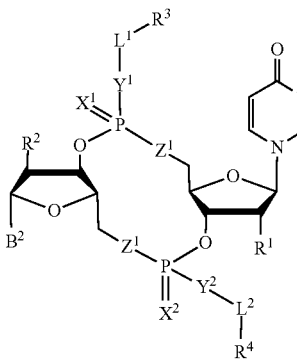

Formula (II-j)

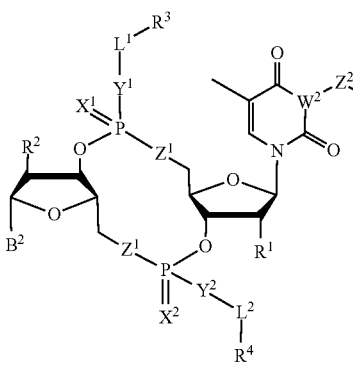

or a pharmaceutically acceptable salt or stereoisomer thereof, wherein:

$W^1$ is $N(R^5)$, —O—CH; and $W^2$ is N or CH.

In one aspect, the present disclosure describes a method of inducing the expression of a pattern recognition receptor in a subject suffering from a microbial infection, comprising administering to the subject a therapeutically effective amount of a compound of Formula (I), Formula (I)

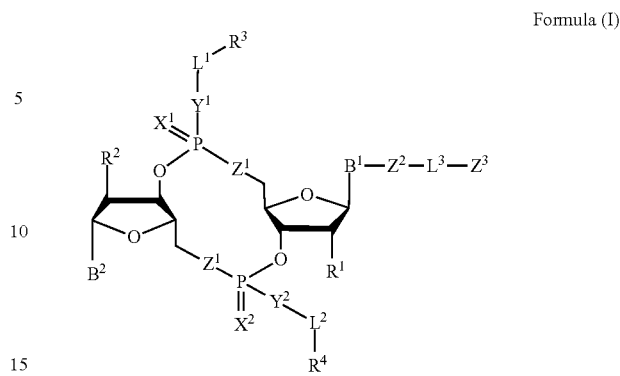

or a pharmaceutically acceptable salt or stereoisomer thereof, wherein:

each of $B^1$ and $B^2$ is independently a purinyl nucleobase or pyrimidinyl nucleobase;

each of $X^1$ and $X^2$ is independently O or S;

each of $Y^1$ and $Y^2$ is independently O, S, or $N(R^5)$;

each of $Z^1$ is independently O or S;

$Z^2$ is —O—, —$N(R^5)$—, —S—, —C(O)—, —C(O)N($R^5$)—, —OC(O)N($R^5$)—, —N($R^5$)C(O)O—, -aryl-, -heteroaryl-, —S(O)—, —S(O)$_2$—, —S(O)N($R^5$)—, —S(O)$_2$N($R^5$)— or —N($R^5$)S(O)—;

$Z^3$ is hydrogen, heterocyclyl, heterocyclyl-$C_1$-$C_{20}$-alkylene-$Q^1$, —OH, —N($R^5$)$_2$, $SR^5$, —CHO, —C(O)N($R^5$)$_2$, —OC(O)N($R^5$)$_2$, —N($R^5$)C(O)O$R^5$, aryl, heteroaryl, —S(O)$R^5$, —S(O)$_2R^5$, —S(O)N($R^5$)$_2$, —S(O)$_2$N($R^5$)$_2$, —N($R^5$)S(O)$R^5$, —OSi($C_1$-$C_4$ alkyl)$_3$, or —C(O)$C_2$-$C_6$ alkenyl (e.g., —$C_2$-$C_4$ alkenyl);

$L^1$ is —$C_1$-$C_6$— alkylene (e.g., $C_1$-$C_3$ alkylene) or —$C_1$-$C_6$— heteroalkylene (e.g., —$C_1$-$C_3$ heteroalkylene);

$L^2$ is absent, —$C_1$-$C_6$— alkylene (e.g., —$C_1$-$C_3$— alkylene) or —$C_1$-$C_6$— heteroalkylene, wherein each alkylene and hetero alkylene is optionally substituted with one or more $R^6$;

$L^3$ is oligiopeptide-C(O)—, oligiopeptide-aryl-$C_1$-$C_6$-alkylene-, oligiopeptide-aryl-$C_1$-$C_6$-heteroalkylene, oligiopeptide-aryl-$C_1$-$C_6$-alklyene-C(O)—, oligiopeptide-$C_1$-$C_6$-alkylene-C(O)—, oligiopeptide-$C_1$-$C_6$-heteroalkylene-C(O)—, —$C_1$-$C_{40}$— alkylene (e.g., —$C_1$-$C_{20}$— alkylene), —$C_1$-$C_{40}$— heteroalkylene (e.g., —$C_1$-$C_{20}$— heteroalkyl), —$C_1$-$C_{40}$— alkenylene (e.g., —$C_2$-$C_{20}$— alkenylene), or —$C_1$-$C_{40}$-alkynylene (e.g., —$C_2$-$C_{20}$— alkynylene), wherein the oligopeptide is optionally substituted by one or more $R^{14}$;

Q is C(O), C(S), or $CH_2$;

each of $R^1$ and $R^2$ is independently hydrogen, halo, —CN, —$C_1$-$C_{20}$ alkyl (e.g., —$C_1$-$C_6$ alkyl), or $OR^7$;

each $R^3$ and $R^4$ is independently hydrogen, —$C_1$-$C_{20}$— alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$;

$R^5$ is hydrogen or —$C_1$-$C_{20}$ alkyl (e.g., —$C_1$-$C_6$ alkyl);

$R^6$ is halo, —CN, —$C_1$-$C_{20}$ alkyl (e.g., —$C_1$-$C_6$ alkyl), —$OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$;

$R^7$ is hydrogen, $—C_1-C_{20}$ alkyl (e.g., $C_1-C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$;

each $R^8$ is independently $—C_1-C_{20}$ alkyl (e.g., $—C_1-C_6$ alkyl), $—C_1-C_{20}$ heteroalkyl, $—C(O)—$, $—C_1-C_{20}$ alkyl, $—OC(O)—C_1-C_{20}$ alkyl (e.g., $—C_1-C_6$ alkyl), $—C(O)O—C_1-C_{20}$ alkyl (e.g., $—C_1-C_6$ alkyl), $—OC(O)O—C_1-C_{20}$ alkyl (e.g., $—C_1-C_6$ alkyl), $—C(O)N(R^5)—C_1-C_{20}$ alkyl (e.g., $—C_1-C_6$ alkyl), $—N(R^5)C(O)—C_1-C_{20}$ alkyl (e.g., $—C_1-C_6$ alkyl), $—OC(O)N(R^5)—C_1-C_{20}$ alkyl (e.g., $—C_1-C_6$ alkyl), $—O$-aryl, $—O$-heteroaryl, $—C(O)$-aryl, $—C(O)$-heteroaryl, $—OC(O)$-aryl, $—C(O)O$-aryl, $—OC(O)$-heteroaryl, $—C(O)O$-heteroaryl, $—C(O)O$-aryl, $—C(O)O$-heteroaryl, $—C(O)N(R^5)$-aryl, $—C(O)N(R^5)$-heteroaryl, $—N(R^5)C(O)$-aryl, $—N(R^5)_2C(O)$-aryl, or $—N(R^5)C(O)$-heteroaryl, $—S(O)_2N(R^5)$-aryl, wherein each alkyl, heteroalkyl, aryl, and heteroaryl is optionally substituted by one or more $R^9$;

each $R^9$ is independently $—C_1-C_{20}$ alkyl, $—O—C_1-C_{20}$ alkyl, $—C_1-C_{20}$ heteroalkyl, halo, $—CN$, $—OH$, oxo, aryl, heteroaryl, $—O$-aryl, or $—O$-heteroaryl;

$Q^1$ is C(O), C(S), or $CH_2$; and each $R^{16}$ is independently, $—C_1-C_{20}$ alkyl (e.g., $—C_1-C_6$ alkyl), $—C_1-C_{20}$ heteroalkyl (e.g., $—C_1-C_6$ heteroalkyl), $—OC(O)OC_1-C_{20}$ alkyl (e.g., $—C_1-C_6$ alkyl), $C(O)N(R^4)_2$ cycloalkyl, heterocyclyl, aryl, or heteroaryl.

In one aspect, the present disclosure describes a method of inducing the expression of a pattern recognition receptor in a subject suffering from a microbial infection, comprising administering to the subject a therapeutically effective amount of a compound of Formula (II),

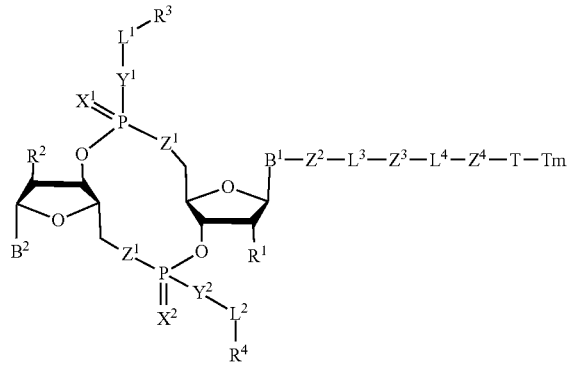

Formula (II)

or a pharmaceutically acceptable salt or stereoisomer thereof, wherein:

Tm is a targeting moiety:

each of $B^1$ and $B^2$ is independently a purinyl nucleobase or pyrimidinyl nucleobase;

each of $X^1$ and $X^2$ is independently O or S;

each of $Y^1$ and $Y^2$ is independently O, S, or $N(R^5)$;

each of $Z^1$ is independently O or S;

$Z^2$ is $—O—$, $—N(R^5)—$, $—S—$, $—C(O)—$, $—C(O)N(R^5)—$, $—OC(O)N(R^5)—$, $—N(R^5)C(O)O—$, -aryl-, -heteroaryl-, $—S(O)—$, $—S(O)_2—$, $—S(O)N(R^5)—$, $—S(O)_2N(R^5)—$ or $—N(R^5)S(O)—$;

$Z^3$ is absent, hydrogen, heterocyclyl, heterocyclyl-$C_1-C_{20}$-alkylene-$Q^1$, $—OH$, $—N(R^5)_2$, $SR^5$, $—CHO$, $—C(O)N(R^5)_2$, $—OC(O)N(R^5)_2$, $—N(R^5)C(O)OR^5$, aryl, heteroaryl, $—S(O)R^5$, $—S(O)_2R^5$, $—S(O)N(R^5)_2$, $—S(O)_2N(R^5)_2$, $—N(R^5)S(O)R^5$, $—OSi(C_1-C_4$ alkyl$)_3$, or $—C(O)C_2-C_6$ alkenyl (e.g., $—C_2-C_4$ alkenyl);

$Z^4$ is a self-immolative group or absent;

T is a absent or spacer group;

each $L^1$ and $L^2$ is absent, $—C_1-C_6—$ alkylene (e.g., $—C_1-C_3—$ alkylene) or $—C_1-C_6$-heteroalkylene, wherein each alkylene and heteroalkyl is optionally substituted with one or more $R^6$;

$L^3$ is oligopeptide-C(O)—, oligopeptide-aryl-$C_1-C_6$-alkylene-, oligopeptide-aryl-$C_1-C_6$-alklyene-C(O)—, oligopeptide-aryl-$C_1-C_6$-heteroalkylene, oligopeptide-$C_1$-$C_6$-alkylene-C(O)—, oligopeptide-$C_1$-$C_6$-heteroalkylene-C(O)—, $—C_1-C_{40}$-alkylene (e.g., $—C_1-C_{20}—$ alkylene), $—C_1-C_{40}—$ heteroalkylene (e.g., $—C_1-C_{20}$-heteroalkyl), $—C_1-C_{40}—$ alkenylene (e.g., $—C_2-C_{20}—$ alkenylene), or $—C_1-C_{40}$-alkynylene (e.g., $—C_2-C_{20}—$ alkynylene), wherein the oligopeptide is optionally substituted by one or more $R^{14}$;

$L^4$ is absent or a linker connecting $Z^3$ and $Z^4$;

$Q^1$ is C(O), C(S), or $CH_2$;

each of $R^1$ and $R^2$ is independently hydrogen, halo, $—CN$, $—C_1-C_{20}$ alkyl (e.g., $C_1-C_6$ alkyl), or $—OR^7$;

each $R^3$ and $R^4$ is independently hydrogen, $—C_1-C_{20}—$ alkyl (e.g., $—C_1-C_6$ alkyl), $—C_1-C_{20}$ heteroalkyl (e.g., $—C_1-C_6$ heteroalkyl), $—OC(O)OC_1-C_{20}$ alkyl (e.g., $—C_1-C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$;

$R^5$ is hydrogen or $—C_1-C_{20}$ alkyl (e.g., $—C_1-C_6$ alkyl);

$R^6$ is halo, $—CN$, $—C_1-C_{20}$ alkyl (e.g., $—C_1-C_6$ alkyl), $—OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$;

$R^7$ is hydrogen, $—C_1-C_{20}$ alkyl (e.g., $—C_1-C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$;

each $R^8$ is independently $—C_1-C_{20}$ alkyl (e.g., $—C_1-C_6$ alkyl), $—C_1-C_{20}$ heteroalkyl, $—C(O)—C_1-C_2$ alkyl, $—OC(O)—C_1-C_{20}$ alkyl (e.g., $—C_1-C_6$ alkyl), $—C(O)O—C_1-C_{20}$ alkyl (e.g., $—C_1-C_6$ alkyl), $—OC(O)O—C_1-C_{20}$ alkyl (e.g., $—C_1-C_6$ alkyl), $—C(O)N(R^5)—C_1-C_{20}$ alkyl (e.g., $—C_1-C_6$ alkyl), $—N(R^5)C(O)—C_1-C_{20}$ alkyl (e.g., $—C_1-C_6$ alkyl), $—OC(O)N(R^5)—C_1-C_{20}$ alkyl (e.g., $—C_1-C_6$ alkyl), $—O$-aryl, $—O—$ heteroaryl, $—C(O)$-aryl, $—C(O)$-heteroaryl, $—OC(O)$-aryl, $—C(O)O$-aryl, $—OC(O)—$ heteroaryl, $—C(O)O$-heteroaryl, $—C(O)O$-aryl, $—C(O)O$-heteroaryl, $—C(O)N(R^5)$-aryl, $—C(O)N(R^5)$-heteroaryl, $—N(R^5)C(O)$-aryl, $—N(R^5)_2C(O)$-aryl, or $—N(R^5)C(O)$-heteroaryl, $—S(O)_2N(R^5)$-aryl, wherein each alkyl, heteroalkyl, aryl, and heteroaryl is optionally substituted by one or more $R^9$;

each $R^9$ is independently $—C_1-C_{20}$ alkyl, $—O—C_1-C_{20}$ alkyl, $—C_1-C_{20}$ heteroalkyl, halo, $—CN$, $—OH$, oxo, aryl, heteroaryl, $—O$-aryl, or $—O$-heteroaryl; and each $R^{16}$ is independently, $—C_1-C_{20}$ alkyl (e.g., $—C_1-C_6$ alkyl), $—C_1-C_{20}$ heteroalkyl (e.g., $—C_1-C_6$ heteroalkyl), $—OC(O)OC_1-C_{20}$ alkyl (e.g., $—C_1-C_6$ alkyl), $C(O)N(R^4)_2$ cycloalkyl, heterocyclyl, aryl, or heteroaryl.

In another aspect, the disclosure features a method of treating cancer in a subject, comprising administering to the subject a therapeutically effective amount of a compound of Formula (I), Formula (I)

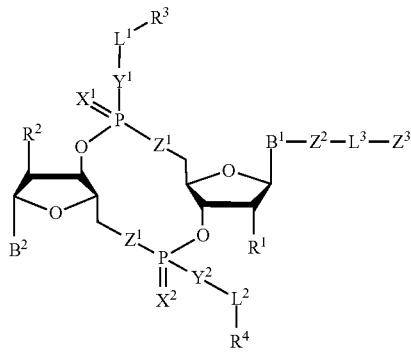

or a pharmaceutically acceptable salt or stereoisomer thereof,
wherein:
each of $B^1$ and $B^2$ is independently a purinyl nucleobase or pyrimidinyl nucleobase;
each of $X^1$ and $X^2$ is independently O or S;
each of $Y^1$ and $Y^2$ is independently O, S, or $N(R^5)$;
each of $Z^1$ is independently O or S;
$Z^2$ is —O—, —$N(R^5)$—, —S—, —C(O)—, —C(O)N($R^5$)—, —OC(O)N($R^5$)—, —N($R^5$)C(O)O—, -aryl-, -heteroaryl-, —S(O)—, —S(O)$_2$—, —S(O)N($R^5$)—, —S(O)$_2$N($R^5$)— or —N($R^5$)S(O)—;
$Z^3$ is hydrogen, heterocyclyl, heterocyclyl-$C_1$-$C_{20}$-alkylene-$Q^1$, —OH, —N($R^5$)$_2$, $SR^5$, —CHO, —C(O)N($R^5$)$_2$, —OC(O)N($R^5$)$_2$, —N($R^5$)C(O)O$R^5$, aryl, heteroaryl, —S(O)$R^5$, —S(O)$_2R^5$, —S(O)N($R^5$)$_2$, —S(O)$_2$N($R^5$)$_2$, —N($R^5$)S(O)$R^5$, —OSi($C_1$-$C_4$ alkyl)$_3$, or —C(O)$C_2$-$C_6$ alkenyl (e.g., —$C_2$-$C_4$ alkenyl);
$L^1$ is —$C_1$-$C_6$— alkylene (e.g., $C_1$-$C_3$ alkylene) or —$C_1$-$C_6$— heteroalkylene (e.g., —$C_1$-$C_3$ heteroalkylene);
$L^2$ is absent, —$C_1$-$C_6$— alkylene (e.g., —$C_1$-$C_3$— alkylene) or —$C_1$-$C_6$— heteroalkylene, wherein each alkylene and hetero alkylene is optionally substituted with one or more $R^6$;
$L^3$ is oligopeptide-C(O)—, oligopeptide-aryl-$C_1$-$C_6$-alkylene-, oligopeptide-aryl-$C_1$-$C_6$-heteroalkylene, oligopeptide-aryl-$C_1$-$C_6$-alkylene-C(O)—, oligopeptide-$C_1$-$C_6$-alkylene-C(O)—, oligopeptide-$C_1$-$C_6$-heteroalkylene-C(O)—, —$C_1$-$C_{40}$— alkylene (e.g., —$C_1$-$C_{20}$— alkylene), —$C_1$-$C_{40}$— heteroalkylene (e.g., —$C_1$-$C_{20}$— heteroalkyl), —$C_1$-$C_{40}$— alkenylene (e.g., —$C_2$-$C_{20}$— alkenylene), or —$C_1$-$C_{40}$-alkynylene (e.g., —$C_2$-$C_{20}$— alkynylene), wherein the oligopeptide is optionally substituted by one or more $R^{14}$;
Q is C(O), C(S), or $CH_2$;
each of $R^1$ and $R^2$ is independently hydrogen, halo, —CN, —$C_1$-$C_{20}$ alkyl (e.g., —$C_1$-$C_6$ alkyl), or $OR^7$;
each $R^3$ and $R^4$ is independently hydrogen, —$C_1$-$C_{20}$— alkyl (e.g., —$C_1$-$C_6$ alkyl), —$C_1$-$C_2$ heteroalkyl (e.g., —$C_1$-$C_6$ heteroalkyl), —OC(O)O$C_1$-$C_{20}$ alkyl (e.g., —$C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$;
$R^5$ is hydrogen or —$C_1$-$C_{20}$ alkyl (e.g., —$C_1$-$C_6$ alkyl);
$R^6$ is halo, —CN, —$C_1$-$C_{20}$ alkyl (e.g., —$C_1$-$C_6$ alkyl), —$OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$;

$R^7$ is hydrogen, —$C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$;
each $R^8$ is independently —$C_1$-$C_{20}$ alkyl (e.g., —$C_1$-$C_6$ alkyl), —$C_1$-$C_{20}$ heteroalkyl, —C(O), —$C_1$-$C_{20}$ alkyl, —OC(O)—$C_1$-$C_{20}$ alkyl (e.g., —$C_1$-$C_6$ alkyl), —C(O)O—$C_1$-$C_{20}$ alkyl (e.g., —$C_1$-$C_6$ alkyl), —OC(O)O—$C_1$-$C_{20}$ alkyl (e.g., —$C_1$-$C_6$ alkyl), —C(O)N($R^5$)—$C_1$-$C_{20}$ alkyl (e.g., —$C_1$-$C_6$ alkyl), —N($R^5$)C(O)—$C_1$-$C_{20}$ alkyl (e.g., —$C_1$-$C_6$ alkyl), —OC(O)N(R')—$C_1$-$C_{20}$ alkyl (e.g., —$C_1$-$C_6$ alkyl), —O-aryl, —O-heteroaryl, —C(O)-aryl, —C(O)-heteroaryl, —OC(O)-aryl, —C(O)O-aryl, —OC(O)-heteroaryl, —C(O)O-heteroaryl, —C(O)O-aryl, —C(O)O-heteroaryl, —C(O)N($R^5$)-aryl, —C(O)N($R^5$)-heteroaryl, —N($R^5$)C(O)-aryl, —N($R^5$)$_2$C(O)-aryl, or —N($R^5$)C(O)-heteroaryl, —S(O)$_2$N($R^5$)-aryl, wherein each alkyl, heteroalkyl, aryl, and heteroaryl is optionally substituted by one or more $R^9$;
each $R^9$ is independently —$C_1$-$C_{20}$ alkyl, —O—$C_1$-$C_{20}$ alkyl, —$C_1$-$C_{20}$ heteroalkyl, halo, —CN, —OH, oxo, aryl, heteroaryl, —O-aryl, or —O-heteroaryl;
$Q^1$ is C(O), C(S), or $CH_2$; and
each $R^{16}$ is independently, —$C_1$-$C_{20}$ alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), C(O)N($R^4$)$_2$ cycloalkyl, heterocyclyl, aryl, or heteroaryl.

In another aspect, the disclosure features a method of treating cancer in a subject, comprising administering to the subject a therapeutically effective amount of a compound of Formula (II), Formula (II)

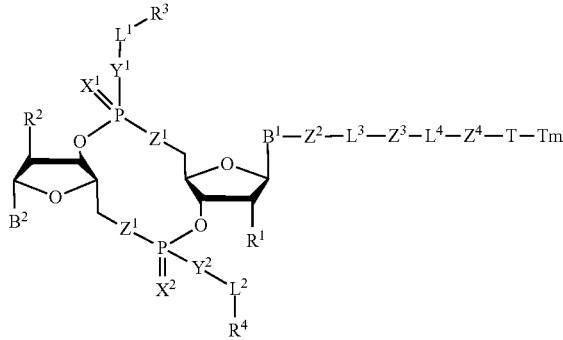

or a pharmaceutically acceptable salt or stereoisomer thereof,
wherein:
Tm is a targeting moiety;
each of $B^1$ and $B^2$ is independently a purinyl nucleobase or pyrimidinyl nucleobase;
each of $X^1$ and $X^2$ is independently O or S;
each of $Y^1$ and $Y^2$ is independently O, S, or $N(R^5)$;
each of $Z^1$ is independently O or S;
$Z^2$ is —O—, —$N(R^5)$—, —S—, —C(O)—, —C(O)N($R^5$)—, —OC(O)N($R^5$)—, —N($R^5$)C(O)O—, -aryl-, -heteroaryl-. —S(O)—, —S(O)$_2$—, —S(O)N($R^5$)—, —S(O)$_2$N($R^5$)— or —N($R^5$)S(O)—;
$Z^3$ is absent, hydrogen, heterocyclyl, heterocyclyl-$C_1$-$C_{20}$-alkylene-$Q^1$, —OH, —N($R^5$)$_2$, $SR^5$, —CHO, —C(O)N($R^5$)$_2$, —OC(O)N($R^5$)$_2$, —N($R^5$)C(O)O$R^5$, aryl, heteroaryl, —S(O)$R^5$, —S(O)$_2R^5$, —S(O)N($R^5$)$_2$, —S(O)$_2$N $(R^5)_2$, —$N(R^5)S(O)R^5$, —$OSi(C_1-C_4$ alkyl$)_3$, or —$C(O)$ $C_2-C_6$ alkenyl (e.g., —$C_2-C_4$ alkenyl);

$Z^4$ is a self-immolative group or absent;

T is a absent or spacer group;

each $L^1$ and $L^2$ is absent, —$C_1-C_6$— alkylene (e.g., —$C_1$-$C_3$— alkylene) or —$C_1-C_6$-heteroalkylene, wherein each alkylene and heteroalkyl is optionally substituted with one or more $R^6$;

$L^3$ is oligopeptide-C(O)—, oligopeptide-aryl-$C_1$-$C_6$-alkylene-, oligopeptide-aryl-$C_1$-$C_6$-heteroalkylene, oligopeptide-aryl-$C_1$-$C_6$-alklyene-C(O)—, oligopeptide-$C_1$-$C_6$-alkylene-C(O)—, oligopeptide-$C_1$-$C_6$-heteroalkylene-C(O)—, —$C_1$-$C_{40}$-alkylene (e.g., —$C_1$-$C_{20}$— alkylene), —$C_1$-$C_{40}$— heteroalkylene (e.g., —$C_1$-$C_{20}$-heteroalkyl), —$C_1$-$C_{40}$— alkenylene (e.g., —$C_2$-$C_{20}$— alkenylene), or —$C_1$-$C_{40}$-alkynylene (e.g., —$C_2$-$C_{20}$— alkynylene), wherein the oligopeptide is optionally substituted by one or more $R^{14}$;

$L^4$ is absent or a linker connecting $Z^3$ and $Z^4$;

$Q^1$ is C(O), C(S), or $CH_2$;

each of $R^1$ and $R^2$ is independently hydrogen, halo, —CN, —$C_1$-$C_{20}$ alkyl (e.g., $C_1$-$C_6$ alkyl), or —OR;

each $R^3$ and $R^4$ is independently hydrogen, —$C_1$-$C_{20}$— alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$;

$R^5$ is hydrogen or —$C_1$-$C_{20}$ alkyl (e.g., —$C_1$-$C_6$ alkyl);

$R^6$ is halo, —CN, —$C_1$-$C_{20}$ alkyl (e.g., —$C_1$-$C_6$ alkyl), —$OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$;

$R^7$ is hydrogen, —$C_1$-$C_{20}$ alkyl (e.g., —$C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$;

each $R^8$ is independently —$C_1$-$C_{20}$ alkyl (e.g., —$C_1$-$C_6$ alkyl), —$C_1$-$C_{20}$ heteroalkyl, —C(O)—$C_1$-$C_{20}$ alkyl, —OC(O)—$C_1$-$C_{20}$ alkyl (e.g., —$C_1$-$C_6$ alkyl), —C(O)O—$C_1$-$C_{20}$ alkyl (e.g., —$C_1$-$C_6$ alkyl), —OC(O)O—$C_1$-$C_{20}$ alkyl (e.g., —$C_1$-$C_6$ alkyl), —C(O)N($R^5$)—$C_1$-$C_{20}$ alkyl (e.g., —$C_1$-$C_6$ alkyl), —N($R^5$)C(O)—$C_1$-$C_{20}$ alkyl (e.g., —$C_1$-$C_6$ alkyl), —OC(O)N($R^5$)—$C_1$-$C_{20}$ alkyl (e.g., —$C_1$-$C_6$ alkyl), —O-aryl, —O— heteroaryl, —C(O)-aryl, —C(O)-heteroaryl, —OC(O)-aryl, —C(O)O-aryl, —OC(O)— heteroaryl, —C(O)O-heteroaryl, —C(O)O-aryl, —C(O)O-heteroaryl, —C(O)N($R^5$)-aryl, —C(O)N($R^5$)-heteroaryl, —N($R^5$)C(O)-aryl, —N($R^5$)$_2$C(O)-aryl, or —N($R^5$)C(O)-heteroaryl, —S(O)$_2$N($R^5$)-aryl, wherein each alkyl, heteroalkyl, aryl, and heteroaryl is optionally substituted by one or more $R^9$;

each $R^9$ is independently —$C_1$-$C_{20}$ alkyl, —O—$C_1$-$C_{20}$ alkyl, —$C_1$-$C_{20}$ heteroalkyl, halo, —CN, —OH, oxo, aryl, heteroaryl, —O-aryl, or —O-heteroaryl; and each $R^{16}$ is independently, —$C_1$-$C_{20}$ alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), C(O)N($R^4$)$_2$ cycloalkyl, heterocyclyl, aryl, or heteroaryl.

In another aspect, the disclosure features a composition, comprising a vaccine, and a vaccine adjuvant comprising a compound of Formula (I),

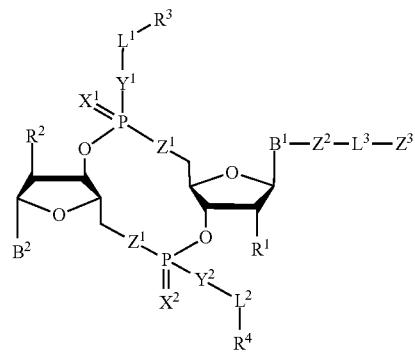

Formula (I)

or a pharmaceutically acceptable salt or stereoisomer thereof, wherein:

each of $B^1$ and $B^2$ is independently a purinyl nucleobase or pyrimidinyl nucleobase;

each of $X^1$ and $X^2$ is independently O or S;

each of $Y^1$ and $Y^2$ is independently O, S, or N($R^5$);

each of $Z^1$ is independently O or S;

$Z^2$ is —O—, —N($R^5$)—, —S—, —C(O)—, —C(O)N($R^5$)—, —OC(O)N($R^5$)—, —N($R^5$)C(O)O—, -aryl-, -heteroaryl-, —S(O)—, —S(O)$_2$—, —S(O)N($R^5$)—, —S(O)$_2$N($R^5$)— or —N($R^5$)S(O)—;

$Z^3$ is hydrogen, heterocyclyl, heterocyclyl-$C_1$-$C_{20}$-alkylene-$Q^1$, —OH, —N($R^5$)$_2$, $SR^5$, —CHO, —C(O)N($R^5$)$_2$, —OC(O)N($R^5$)$_2$, —N($R^5$)C(O)$OR^5$, aryl, heteroaryl, —S(O)$R^5$, —S(O)$_2R^5$, —S(O)N($R^5$)$_2$, —S(O)$_2$N($R^5$)$_2$, —N($R^5$)S(O)$R^5$, —OSi($C_1$-$C_4$ alkyl)$_3$, or —C(O)$C_2$-$C_6$ alkenyl (e.g., —$C_2$-$C_4$ alkenyl);

$L^1$ is —$C_1$-$C_6$— alkylene (e.g., $C_1$-$C_3$ alkylene) or —$C_1$-$C_6$— heteroalkylene (e.g., —$C_1$-$C_3$ heteroalkylene);

$L^2$ is absent, —$C_1$-$C_6$— alkylene (e.g., —$C_1$-$C_3$— alkylene) or —$C_1$-$C_6$— heteroalkylene, wherein each alkylene and hetero alkylene is optionally substituted with one or more $R^6$;

$L^3$ is oligopeptide-C(O)—, oligopeptide-aryl-$C_1$-$C_6$-alkylene-, oligopeptide-aryl-$C_1$-$C_6$-heteroalkylene, oligopeptide-aryl-$C_1$-$C_6$-alklyene-C(O)—, oligopeptide-$C_1$-$C_6$-alkylene-C(O)—, oligopeptide-$C_1$-$C_6$-heteroalkylene-C(O)—, —$C_1$-$C_{40}$— alkylene (e.g., —$C_1$-$C_{20}$— alkylene), —$C_1$-$C_{40}$— heteroalkylene (e.g., —$C_1$-$C_{20}$— heteroalkyl), —$C_1$-$C_{40}$— alkenylene (e.g., —$C_2$-$C_{20}$— alkenylene), or —$C_1$-$C_{40}$-alkynylene (e.g., —$C_2$-$C_{20}$— alkynylene), wherein the oligopeptide is optionally substituted by one or more $R^{14}$;

Q is C(O), C(S), or $CH_2$;

each of $R^1$ and $R^2$ is independently hydrogen, halo, —CN, —$C_1$-$C_{20}$ alkyl (e.g., —$C_1$-$C_6$ alkyl), or $OR^7$;

each $R^3$ and $R^4$ is independently hydrogen, —$C_1$-$C_{20}$— alkyl (e.g., —$C_1$-$C_6$ alkyl), —$C_1$-$C_2$ heteroalkyl (e.g., —$C_1$-$C_6$ heteroalkyl), —OC(O)O$C_1$-$C_{20}$ alkyl (e.g., —$C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$;

$R^5$ is hydrogen or —$C_1$-$C_{20}$ alkyl (e.g., —$C_1$-$C_6$ alkyl);

$R^6$ is halo, —CN, —$C_1$-$C_{20}$ alkyl (e.g., —$C_1$-$C_6$ alkyl), —$OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$;

$R^7$ is hydrogen, —$C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$;

each $R^8$ is independently —$C_1$-$C_{20}$ alkyl (e.g., —$C_1$-$C_6$ alkyl), —$C_1$-$C_{20}$ heteroalkyl, —C(O)—, —$C_1$-$C_{20}$ alkyl, —OC(O)—$C_1$-$C_{20}$ alkyl (e.g., —$C_1$-$C_6$ alkyl), —C(O)O—$C_1$-$C_{20}$ alkyl (e.g., —$C_1$-$C_6$ alkyl), —OC(O)O—$C_1$-$C_{20}$ alkyl (e.g., —$C_1$-$C_6$ alkyl), —C(O)N($R^5$)—$C_1$-$C_{20}$ alkyl (e.g., —$C_1$-$C_6$ alkyl), —N($R^5$)C(O)—$C_1$-$C_{20}$ alkyl (e.g., —$C_1$-$C_6$ alkyl), —OC(O)N($R^5$)—$C_1$-$C_{20}$ alkyl (e.g., —$C_1$-$C_6$ alkyl), —O-aryl, —O-heteroaryl, —C(O)-aryl, —C(O)-heteroaryl, —OC(O)-aryl, —C(O)O-aryl, —OC(O)-heteroaryl, —C(O)O-heteroaryl, —C(O)O-aryl, —C(O)O-heteroaryl, —C(O)N($R^5$)-aryl, —C(O)N($R^5$)-heteroaryl, —N($R^5$)C(O)-aryl, —N($R^5$)$_2$C(O)-aryl, or —N($R^5$)C(O)-heteroaryl, —S(O)$_2$N($R^5$)-aryl, wherein each alkyl, heteroalkyl, aryl, and heteroaryl is optionally substituted by one or more $R^9$;

each $R^9$ is independently —$C_1$-$C_{20}$ alkyl, —O—$C_1$-$C_{20}$ alkyl, —$C_1$-$C_{20}$ heteroalkyl, halo, —CN, —OH, oxo, aryl, heteroaryl, —O-aryl, or —O-heteroaryl;

$Q^1$ is C(O), C(S), or $CH_2$; and each $R^{16}$ is independently, —$C_1$-$C_{20}$ alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), C(O)N($R^4$)$_2$ cycloalkyl, heterocyclyl, aryl, or heteroaryl.

In another aspect, the disclosure features a composition, comprising a vaccine, and a vaccine adjuvant comprising a compound of Formula (II),

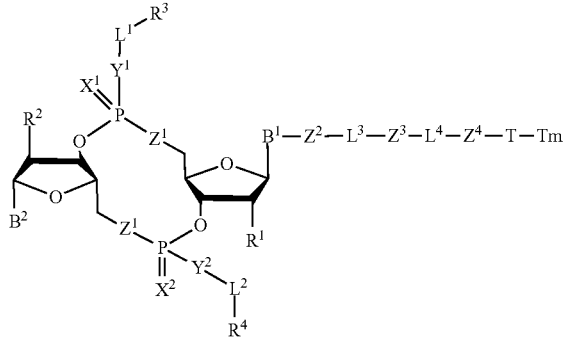

Formula (II)

or a pharmaceutically acceptable salt or stereoisomer thereof, wherein:

Tm is a targeting moiety;

each of $B^1$ and $B^2$ is independently a purinyl nucleobase or pyrimidinyl nucleobase;

each of $X^1$ and $X^2$ is independently O or S;

each of $Y^1$ and $Y^2$ is independently O, S, or N($R^5$);

each of $Z^1$ is independently O or S;

$Z^2$ is —O—, —N($R^5$)—, —S—, —C(O)—, —C(O)N($R^5$)—, —OC(O)N($R^5$)—, —N($R^5$)C(O)O—, -aryl-, -heteroaryl-, —S(O)—, —S(O)$_2$—, —S(O)N($R^5$)—, —S(O)$_2$N($R^5$)— or —N($R^5$)S(O)—;

$Z^3$ is absent, hydrogen, heterocyclyl, heterocyclyl-$C_1$-$C_{20}$-alkylene-$Q^1$, —OH, —N($R^5$)$_2$, SR$^5$, —CHO, —C(O)N(R$^5$)$_2$, —OC(O)N(R$^5$)$_2$, —N(R$^5$)C(O)OR$^5$, aryl, heteroaryl, —S(O)R$^5$, —S(O)$_2$R$^5$, —S(O)N(R$^5$)$_2$, —S(O)$_2$N(R$^5$)$_2$, —N(R$^5$)S(O)R$^5$, —OSi($C_1$-$C_4$ alkyl)$_3$, or —C(O)$C_2$-$C_6$ alkenyl (e.g., —$C_2$-$C_4$ alkenyl);

$Z^4$ is a self-immolative group or absent;

T is a absent or spacer group;

each $L^1$ and $L^2$ is absent, —$C_1$-$C_6$— alkylene (e.g., —$C_1$-$C_3$— alkylene) or —$C_1$-$C_6$-heteroalkylene, wherein each alkylene and heteroalkyl is optionally substituted with one or more $R^6$;

$L^3$ is oligiopeptide-C(O)—, oligiopeptide-aryl-$C_1$-$C_6$-alkylene-, oligiopeptide-aryl-$C_1$-$C_6$-alklyene-C(O)—, oligiopeptide-aryl-$C_1$-$C_6$-heteroalkylene, oligiopeptide-$C_1$-$C_6$-alkylene-C(O)—, oligiopeptide-$C_1$-$C_6$-heteroalkylene-C(O)—, —$C_1$-$C_{40}$-alkylene (e.g., —$C_1$-$C_{20}$— alkylene), —$C_1$-$C_{40}$— heteroalkylene (e.g., —$C_1$-$C_{20}$-heteroalkyl), —$C_1$-$C_{40}$— alkenylene (e.g., —$C_2$-$C_{20}$— alkenylene), or —$C_1$-$C_{40}$-alkynylene (e.g., —$C_2$-$C_{20}$— alkynylene), wherein the oligiopeptide is optionally substituted by one or more $R^{14}$;

$L^4$ is absent or a linker connecting $Z^3$ and $Z^4$;

$Q^1$ is C(O), C(S), or $CH_2$;

each of $R^1$ and $R^2$ is independently hydrogen, halo, —CN, —$C_1$-$C_{20}$ alkyl (e.g., $C_1$-$C_6$ alkyl), or —OR$^7$;

each $R^3$ and $R^4$ is independently hydrogen, —$C_1$-$C_{20}$— alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$;

$R^5$ is hydrogen or —$C_1$-$C_{20}$ alkyl (e.g., —$C_1$-$C_6$ alkyl);

$R^6$ is halo, —CN, —$C_1$-$C_{20}$ alkyl (e.g., —$C_1$-$C_6$ alkyl), —OR$^7$, oxo, cycloalkyl, heterocyclyl, aryl, or heteroaryl, wherein each alkyl, cycloalkyl, heterocyclyl, aryl, and heteroaryl is optionally substituted with one or more $R^8$;

$R^7$ is hydrogen, —$C_1$-$C_{20}$ alkyl (e.g., —$C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$;

each $R^8$ is independently —$C_1$-$C_{20}$ alkyl (e.g., —$C_1$-$C_6$ alkyl), —$C_1$-$C_{20}$ heteroalkyl, —C(O)—$C_1$-$C_{20}$ alkyl, —OC(O)—$C_1$-$C_{20}$ alkyl (e.g., —$C_1$-$C_6$ alkyl), —C(O)O—$C_1$-$C_{20}$ alkyl (e.g., —$C_1$-$C_6$ alkyl), —OC(O)O—$C_1$-$C_{20}$ alkyl (e.g., —$C_1$-$C_6$ alkyl), —C(O)N($R^5$)—$C_1$-$C_{20}$ alkyl (e.g., —$C_1$-$C_6$ alkyl), —N($R^5$)C(O)—$C_1$-$C_{20}$ alkyl (e.g., —$C_1$-$C_6$ alkyl), —OC(O)N($R^5$)—$C_1$-$C_{20}$ alkyl (e.g., —$C_1$-$C_6$ alkyl), —O-aryl, —O— heteroaryl, —C(O)-aryl, —C(O)-heteroaryl, —OC(O)-aryl, —C(O)O-aryl, —OC(O)— heteroaryl, —C(O)O-heteroaryl, —C(O)O-aryl, —C(O)O-heteroaryl, —C(O)N($R^5$)-aryl, —C(O)N($R^5$)-heteroaryl, —N($R^5$)C(O)-aryl, —N($R^5$)$_2$C(O)-aryl, or —N($R^5$)C(O)-heteroaryl, —S(O)$_2$N($R^5$)-aryl, wherein each alkyl, heteroalkyl, aryl, and heteroaryl is optionally substituted by one or more $R^9$;

each $R^9$ is independently —$C_1$-$C_{20}$ alkyl, —O—$C_1$-$C_{20}$ alkyl, —$C_1$-$C_{20}$ heteroalkyl, halo, —CN, —OH, oxo, aryl, heteroaryl, —O-aryl, or —O-heteroaryl; and each $R^{16}$ is independently, —$C_1$-$C_{20}$ alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), C(O)N($R^4$)$_2$ cycloalkyl, heterocyclyl, aryl, or heteroaryl.

In another aspect, the disclosure features a method of inducing the expression of a pattern recognition receptors (PRR) for immune-modulation in a subject, comprising administering to the subject a therapeutically effective amount of a compound of Formula (I), Formula (I)

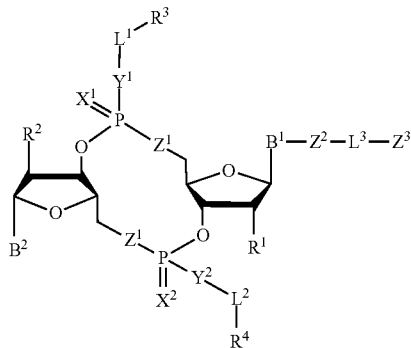

or a pharmaceutically acceptable salt or stereoisomer thereof,
wherein:
each of $B^1$ and $B^2$ is independently a purinyl nucleobase or pyrimidinyl nucleobase;
each of $X^1$ and $X^2$ is independently O or S;
each of $Y^1$ and $Y^2$ is independently O, S, or $N(R^5)$;
each of $Z^1$ is independently O or S;
$Z^2$ is —O—, —N($R^5$)—, —S—, —C(O)—, —C(O)N($R^5$)—, —OC(O)N($R^5$)—, —N($R^5$)C(O)O—, -aryl-, -heteroaryl-, —S(O)—, —S(O)$_2$—, —S(O)N($R^5$)—, —S(O)$_2$N($R^5$)— or —N($R^5$)S(O)—;
$Z^3$ is hydrogen, heterocyclyl, heterocyclyl-$C_1$-$C_{20}$-alkylene-$Q^1$, —OH, —N($R^5$)$_2$, $SR^5$, —CHO, —C(O)N($R^5$)$_2$, —OC(O)N($R^5$)$_2$, —N($R^5$)C(O)O$R^5$, aryl, heteroaryl, —S(O)$R^5$, —S(O)$_2R^5$, —S(O)N($R^5$)$_2$, —S(O)$_2$N($R^5$)$_2$, —N($R^5$)S(O)$R^5$, —OSi($C_1$-$C_4$ alkyl)$_3$, or —C(O)$C_2$-$C_6$ alkenyl (e.g., —$C_2$-$C_4$ alkenyl);
$L^1$ is —$C_1$-$C_6$— alkylene (e.g., $C_1$-$C_3$ alkylene) or —$C_1$-$C_6$— heteroalkylene (e.g., —$C_1$-$C_3$ heteroalkylene);
$L^2$ is absent, —$C_1$-$C_6$— alkylene (e.g., —$C_1$-$C_3$— alkylene) or —$C_1$-$C_6$— heteroalkylene, wherein each alkylene and hetero alkylene is optionally substituted with one or more $R^6$;
$L^3$ is oligopeptide-C(O)—, oligopeptide-aryl-$C_1$-$C_6$-alkylene-, oligopeptide-aryl-$C_1$-$C_6$-heteroalkylene, oligopeptide-aryl-$C_1$-$C_6$-alkylyene-C(O)—, oligopeptide-$C_1$-$C_6$-alkylene-C(O)—, oligopeptide-$C_1$-$C_6$-heteroalkylene-C(O)—, —$C_1$-$C_{40}$— alkylene (e.g., —$C_1$-$C_{20}$— alkylene), —$C_1$-$C_{40}$— heteroalkylene (e.g., —$C_1$-$C_{20}$— heteroalkyl), —$C_1$-$C_{40}$— alkenylene (e.g., —$C_2$-$C_{20}$— alkenylene), or —$C_1$-$C_{40}$— alkynylene (e.g., —$C_2$-$C_{20}$— alkynylene), wherein the oligopeptide is optionally substituted by one or more $R^{14}$;
Q is C(O), C(S), or $CH_2$;
each of $R^1$ and $R^2$ is independently hydrogen, halo, —CN, —$C_1$-$C_{20}$ alkyl (e.g., —$C_1$-$C_6$ alkyl), or $OR^7$;
each $R^3$ and $R^4$ is independently hydrogen, —$C_1$-$C_{20}$— alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$;
$R^5$ is hydrogen or —$C_1$-$C_{20}$ alkyl (e.g., —$C_1$-$C_6$ alkyl);
$R^6$ is halo, —CN, —$C_1$-$C_{20}$ alkyl (e.g., —$C_1$-$C_6$ alkyl), —$OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$;

$R^7$ is hydrogen, —$C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$;
each $R^8$ is independently —$C_1$-$C_{20}$ alkyl (e.g., —$C_1$-$C_6$ alkyl), —$C_1$-$C_{20}$ heteroalkyl, —C(O), —$C_1$-$C_{20}$ alkyl, —OC(O)—$C_1$-$C_{20}$ alkyl (e.g., —$C_1$-$C_6$ alkyl), —C(O)O—$C_1$-$C_{20}$ alkyl (e.g., —$C_1$-$C_6$ alkyl), —OC(O)O—$C_1$-$C_{20}$ alkyl (e.g., —$C_1$-$C_6$ alkyl), —C(O)N($R^5$)—$C_1$-$C_{20}$ alkyl (e.g., —$C_1$-$C_6$ alkyl), —N($R^5$)C(O)—$C_1$-$C_{20}$ alkyl (e.g., —$C_1$-$C_6$ alkyl), —OC(O)N($R^5$)—$C_1$-$C_{20}$ alkyl (e.g., —$C_1$-$C_6$ alkyl), —O-aryl, —O-heteroaryl, —C(O)-aryl, —C(O)-heteroaryl, —OC(O)-aryl, —C(O)O-aryl, —OC(O)-heteroaryl, —C(O)O-heteroaryl, —C(O)O-aryl, —C(O)O-heteroaryl, —C(O)N($R^5$)-aryl, —C(O)N($R^5$)-heteroaryl, —N($R^5$)C(O)-aryl, —N($R^5$)$_2$C(O)-aryl, or —N($R^5$)C(O)-heteroaryl, —S(O)$_2$N($R^5$)-aryl, wherein each alkyl, heteroalkyl, aryl, and heteroaryl is optionally substituted by one or more $R^9$;
each $R^9$ is independently —$C_1$-$C_{20}$ alkyl, —O—$C_1$-$C_{20}$ alkyl, —$C_1$-$C_{20}$ heteroalkyl, halo, —CN, —OH, oxo, aryl, heteroaryl, —O-aryl, or —O-heteroaryl;
$Q^1$ is C(O), C(S), or $CH_2$; and
each $R^{16}$ is independently, —$C_1$-$C_{20}$ alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), C(O)N($R^4$)$_2$ cycloalkyl, heterocyclyl, aryl, or heteroaryl.

In another aspect, the disclosure features a method of inducing the expression of a pattern recognition receptors (PRR) for immune-modulation in a subject, comprising administering to the subject a therapeutically effective amount of a compound of Formula (II), Formula (II)

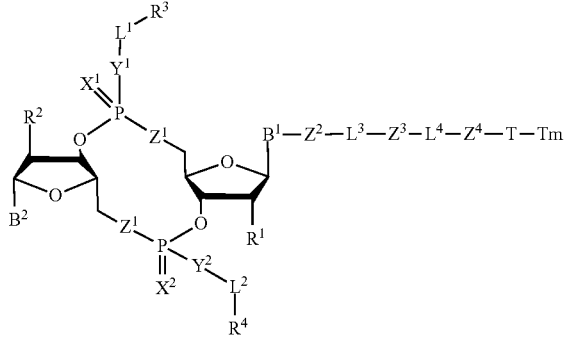

or a pharmaceutically acceptable salt or stereoisomer thereof,
wherein:
Tm is a targeting moiety;
each of $B^1$ and $B^2$ is independently a purinyl nucleobase or pyrimidinyl nucleobase;
each of $X^1$ and $X^2$ is independently O or S;
each of $Y^1$ and $Y^2$ is independently O, S, or $N(R^5)$;
each of $Z^1$ is independently O or S;
$Z^2$ is —O—, —N($R^5$)—, —S—, —C(O)—, —C(O)N($R^5$)—, —OC(O)N($R^5$)—, —N($R^5$)C(O)O—, -aryl-, -heteroaryl-, —S(O)—, —S(O)$_2$—, —S(O)N($R^5$)—, —S(O)$_2$N($R^5$)— or —N($R^5$)S(O)—;
$Z^3$ is absent, hydrogen, heterocyclyl, heterocyclyl-$C_1$-$C_{20}$-alkylene-$Q^1$, —OH, —N($R^5$)$_2$, $SR^5$, —CHO, —C(O)N($R^5$)$_2$, —OC(O)N($R^5$)$_2$, —N($R^5$)C(O)O$R^5$, aryl, heteroaryl, —S(O)$R^5$, —S(O)$_2R^5$, —S(O)N($R^5$)$_2$, —S(O)$_2$N ($R^5$)$_2$, —N($R^5$)S(O)$R^5$, —OSi($C_1$-$C_4$ alkyl)$_3$, or —C(O)$C_2$-$C_6$ alkenyl (e.g., —$C_2$-$C_4$ alkenyl);

$Z^4$ is a self-immolative group or absent;

T is a absent or spacer group;

each $L^1$ and $L^2$ is absent, —$C_1$-$C_6$— alkylene (e.g., —$C_1$-$C_3$— alkylene) or —$C_1$-$C_6$-heteroalkylene, wherein each alkylene and heteroalkyl is optionally substituted with one or more $R^6$;

$L^3$ is oligiopeptide-C(O)—, oligiopeptide-aryl-$C_1$-$C_6$-alkylene-, oligiopeptide-aryl-$C_1$-$C_6$-alklyene-C(O)—, oligiopeptide-aryl-$C_1$-$C_6$-heteroalkylene, oligiopeptide-$C_1$-$C_6$-alkylene-C(O)—, oligiopeptide-$C_1$-$C_6$-heteroalkylene-C(O)—, —$C_1$-$C_{40}$-alkylene (e.g., —$C_1$-$C_{20}$— alkylene), —$C_1$-$C_{40}$— heteroalkylene (e.g., —$C_1$-$C_{20}$-heteroalkyl), —$C_1$-$C_{40}$— alkenylene (e.g., —$C_2$-$C_{20}$— alkenylene), or —$C_1$-$C_{40}$-alkynylene (e.g., —$C_2$-$C_{20}$— alkynylene), wherein the oligopeptide is optionally substituted by one or more $R^{14}$;

$L^4$ is absent or a linker connecting $Z^3$ and $Z^4$;

$Q^1$ is C(O), C(S), or $CH_2$;

each of $R^1$ and $R^2$ is independently hydrogen, halo, —CN, —$C_1$-$C_{20}$ alkyl (e.g., $C_1$-$C_6$ alkyl), or —OR;

each $R^3$ and $R^4$ is independently hydrogen, —$C_1$-$C_{20}$— alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$;

$R^5$ is hydrogen or —$C_1$-$C_{20}$ alkyl (e.g., —$C_1$-$C_6$ alkyl);

$R^6$ is halo, —CN, —$C_1$-$C_{20}$ alkyl (e.g., —$C_1$-$C_6$ alkyl), —$OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$;

$R^7$ is hydrogen, —$C_1$-$C_{20}$ alkyl (e.g., —$C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$;

each $R^8$ is independently —$C_1$-$C_{20}$ alkyl (e.g., —$C_1$-$C_6$ alkyl), —$C_1$-$C_{20}$ heteroalkyl, —C(O)—$C_1$-$C_{20}$ alkyl, —OC(O)—$C_1$-$C_{20}$ alkyl (e.g., —$C_1$-$C_6$ alkyl), —C(O)O—$C_1$-$C_{20}$ alkyl (e.g., —$C_1$-$C_6$ alkyl), —OC(O)O—$C_1$-$C_{20}$ alkyl (e.g., —$C_1$-$C_6$ alkyl), —C(O)N($R^5$)—$C_1$-$C_{20}$ alkyl (e.g., —$C_1$-$C_6$ alkyl), —N($R^5$)C(O)—$C_1$-$C_{20}$ alkyl (e.g., —$C_1$-$C_6$ alkyl), —OC(O)N($R^5$)—$C_1$-$C_{20}$ alkyl (e.g., —$C_1$-$C_6$ alkyl), —O-aryl, —O— heteroaryl, —C(O)-aryl, —C(O)-heteroaryl, —OC(O)-aryl, —C(O)O-aryl, —OC(O)— heteroaryl, —C(O)O-heteroaryl, —C(O)O-aryl, —C(O)O-heteroaryl, —C(O)N($R^5$)-aryl, —C(O)N($R^5$)-heteroaryl, —N($R^5$)C(O)-aryl, —N($R^5$)$_2$C(O)-aryl, or —N($R^5$)C(O)-heteroaryl, —S(O)$_2$N($R^5$)-aryl, wherein each alkyl, heteroalkyl, aryl, and heteroaryl is optionally substituted by one or more $R^9$;

each $R^9$ is independently —$C_1$-$C_{20}$ alkyl, —O—$C_1$-$C_{20}$ alkyl, —$C_1$-$C_{20}$ heteroalkyl, halo, —CN, —OH, oxo, aryl, heteroaryl, —O-aryl, or —O-heteroaryl; and each $R^{16}$ is independently, —$C_1$-$C_{20}$ alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), C(O)N($R^4$)$_2$ cycloalkyl, heterocyclyl, aryl, or heteroaryl.

In another aspect, the disclosure features a method of inducing the expression of a pattern recognition receptor (PRR) for immunomodulation and inducing a therapeutic response in a subject having cancer, comprising administering to the subject a therapeutically effective amount of a compound of Formula (I),

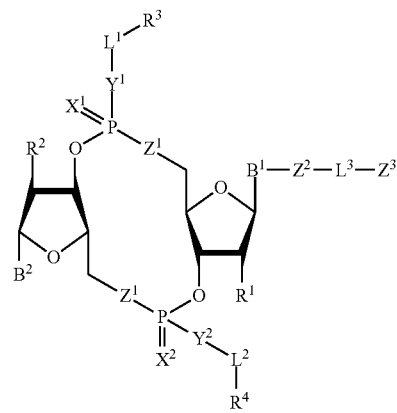

Formula (I)

or a pharmaceutically acceptable salt or stereoisomer thereof, wherein:

each of $B^1$ and $B^2$ is independently a purinyl nucleobase or pyrimidinyl nucleobase;

each of $X^1$ and $X^2$ is independently O or S;

each of $Y^1$ and $Y^2$ is independently O, S, or N($R^5$);

each of $Z^1$ is independently O or S;

$Z^2$ is —O—, —N($R^5$)—, —S—, —C(O)—, —C(O)N($R^5$)—, —OC(O)N($R^5$)—, —N($R^5$)C(O)O—, -aryl-, -heteroaryl-, —S(O)—, —S(O)$_2$—, —S(O)N($R^5$)—, —S(O)$_2$N($R^5$)— or —N($R^5$)S(O)—;

$Z^3$ is hydrogen, heterocyclyl, heterocyclyl-$C_1$-$C_{20}$-alkylene-$Q^1$, —OH, —N($R^5$)$_2$, $SR^5$, —CHO, —C(O)N($R^5$)$_2$, —OC(O)N($R^5$)$_2$, —N($R^5$)C(O)O$R^5$, aryl, heteroaryl, —S(O)$R^5$, —S(O)$_2R^5$, —S(O)N($R^5$)$_2$, —S(O)$_2$N($R^5$)$_2$, —N($R^5$)S(O)$R^5$, —OSi($C_1$-$C_4$ alkyl)$_3$, or —C(O)$C_2$-$C_6$ alkenyl (e.g., —$C_2$-$C_4$ alkenyl);

$L^1$ is —$C_1$-$C_6$— alkylene (e.g., $C_1$-$C_3$ alkylene) or —$C_1$-$C_6$— heteroalkylene (e.g., —$C_1$-$C_3$ heteroalkylene);

$L^2$ is absent, —$C_1$-$C_6$— alkylene (e.g., —$C_1$-$C_3$— alkylene) or —$C_1$-$C_6$— heteroalkylene, wherein each alkylene and hetero alkylene is optionally substituted with one or more $R^6$;

$L^3$ is oligiopeptide-C(O)—, oligiopeptide-aryl-$C_1$-$C_6$-alkylene-, oligiopeptide-aryl-$C_1$-$C_6$-heteroalkylene, oligiopeptide-aryl-$C_1$-$C_6$-alklyene-C(O)—, oligiopeptide-$C_1$-$C_6$-alkylene-C(O)—, oligiopeptide-$C_1$-$C_6$-heteroalkylene-C(O)—, —$C_1$-$C_{40}$— alkylene (e.g., —$C_1$-$C_{20}$— alkylene), —$C_1$-$C_{40}$— heteroalkylene (e.g., —$C_1$-$C_{20}$— heteroalkyl), —$C_1$-$C_{40}$— alkenylene (e.g., —$C_2$-$C_{20}$— alkenylene), or —$C_1$-$C_{40}$-alkynylene (e.g., —$C_2$-$C_{20}$— alkynylene), wherein the oligopeptide is optionally substituted by one or more $R^{14}$;

Q is C(O), C(S), or $CH_2$;

each of $R^1$ and $R^2$ is independently hydrogen, halo, —CN, —$C_1$-$C_{20}$ alkyl (e.g., —$C_1$-$C_6$ alkyl), or $OR^7$;

each $R^3$ and $R^4$ is independently hydrogen, —$C_1$-$C_{20}$— alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more R;

$R^5$ is hydrogen or —$C_1$-$C_{20}$ alkyl (e.g., —$C_1$-$C_6$ alkyl);

$R^6$ is halo, —CN, —$C_1$-$C_{20}$ alkyl (e.g., —$C_1$-$C_6$ alkyl), —$OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$;

$R^7$ is hydrogen, —$C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$;

each $R^8$ is independently —$C_1$-$C_{20}$ alkyl (e.g., —$C_1$-$C_6$ alkyl), —$C_1$-$C_{20}$ heteroalkyl, —C(O), —$C_1$-$C_{20}$ alkyl, —OC(O)—$C_1$-$C_{20}$ alkyl (e.g., —$C_1$-$C_6$ alkyl), —C(O)O—$C_1$-$C_{20}$ alkyl (e.g., —$C_1$-$C_6$ alkyl), —OC(O)O—$C_1$-$C_{20}$ alkyl (e.g., —$C_1$-$C_6$ alkyl), —C(O)N($R^5$)—$C_1$-$C_{20}$ alkyl (e.g., —$C_1$-$C_6$ alkyl), —N($R^5$)C(O)—$C_1$-$C_{20}$ alkyl (e.g., —$C_1$-$C_6$ alkyl), —OC(O)N($R^5$)—$C_1$-$C_{20}$ alkyl (e.g., —$C_1$-$C_6$ alkyl), —O-aryl, —O-heteroaryl, —C(O)-aryl, —C(O)-heteroaryl, —OC(O)-aryl, —C(O)O-aryl, —OC(O)-heteroaryl, —C(O)O-heteroaryl, —C(O)O-aryl, —C(O)O-heteroaryl, —C(O)N($R^5$)-aryl, —C(O)N($R^5$)-heteroaryl, —N($R^5$)C(O)-aryl, —N($R^5$)$_2$C(O)-aryl, or —N($R^5$)C(O)-heteroaryl, —S(O)$_2$N($R^5$)-aryl, wherein each alkyl, heteroalkyl, aryl, and heteroaryl is optionally substituted by one or more $R^9$;

each $R^9$ is independently —$C_1$-$C_{20}$ alkyl, —O—$C_1$-$C_{20}$ alkyl, —$C_1$-$C_{20}$ heteroalkyl, halo, —CN, —OH, oxo, aryl, heteroaryl, —O-aryl, or —O-heteroaryl;

$Q^1$ is C(O), C(S), or $CH_2$; and each $R^{16}$ is independently, —$C_1$-$C_{20}$ alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), C(O)N($R^4$)$_2$ cycloalkyl, heterocyclyl, aryl, or heteroaryl.

In another aspect, the disclosure features a method of inducing the expression of a pattern recognition receptor (PRR) for immunomodulation and inducing a therapeutic response in a subject having cancer, comprising administering to the subject a therapeutically effective amount of a compound of Formula (II), Formula (II)

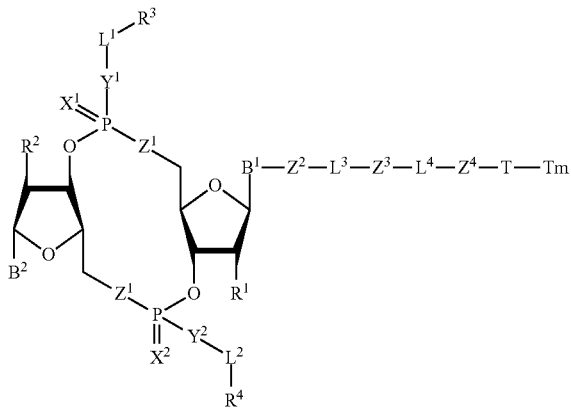

or a pharmaceutically acceptable salt or stereoisomer thereof,
wherein:
Tm is a targeting moiety;
each of $B^1$ and $B^2$ is independently a purinyl nucleobase or pyrimidinyl nucleobase;
each of $X^1$ and $X^2$ is independently O or S;
each of $Y^1$ and $Y^2$ is independently O, S, or N($R^5$);
each of $Z^1$ is independently O or S.
$Z^2$ is —O—, —N($R^5$)—, —S—, —C(O)—, —C(O)N($R^5$)—, —OC(O)N($R^5$)—, —N($R^5$)C(O)O—, -aryl-, -heteroaryl-, —S(O)—, —S(O)$_2$—, —S(O)N($R^5$)—, —S(O)$_2$N($R^5$)— or —N($R^5$)S(O)—;

$Z^3$ is absent, hydrogen, heterocyclyl, heterocyclyl-$C_1$-$C_{20}$-alkylene-$Q^1$, —OH, —N($R^5$)$_2$, $SR^5$, —CHO, —C(O)N($R^5$)$_2$, —OC(O)N($R^5$)$_2$, —N($R^5$)C(O)O$R^5$, aryl, heteroaryl, —S(O)$R^5$, —S(O)$_2R^5$, —S(O)N($R^5$)$_2$, —S(O)$_2$N($R^5$)$_2$, —N($R^5$)S(O)$R^5$, —OSi($C_1$-$C_4$ alkyl)$_3$, or —C(O)$C_2$-$C_6$ alkenyl (e.g., —$C_2$-$C_4$ alkenyl);

$Z^4$ is a self-immolative group or absent;

T is a absent or spacer group;

each $L^1$ and $L^2$ is absent, —$C_1$-$C_6$— alkylene (e.g., —$C_1$-$C_3$— alkylene) or —$C_1$-$C_6$-heteroalkylene, wherein each alkylene and heteroalkyl is optionally substituted with one or more $R^6$;

$L^3$ is oligopeptide-C(O)—, oligopeptide-aryl-$C_1$-$C_6$-alkylene-, oligopeptide-aryl-$C_1$-$C_6$-alklyene-C(O)—, oligopeptide-aryl-$C_1$-$C_6$-heteroalkylene, oligopeptide-$C_1$-$C_6$-alkylene-C(O)—, oligopeptide-$C_1$-$C_6$-heteroalkylene-C(O)—, —$C_1$-$C_{40}$-alkylene (e.g., —$C_1$-$C_{20}$— alkylene), —$C_1$-$C_{40}$— heteroalkylene (e.g., —$C_1$-$C_{20}$-heteroalkyl), —$C_1$-$C_{40}$— alkenylene (e.g., —$C_2$-$C_{20}$— alkenylene), or —$C_1$-$C_{40}$-alkynylene (e.g., —$C_2$-$C_{20}$— alkynylene), wherein the oligopeptide is optionally substituted by one or more $R^{14}$;

$L^4$ is absent or a linker connecting $Z^3$ and $Z^4$;

$Q^1$ is C(O), C(S), or $CH_2$;

each of $R^1$ and $R^2$ is independently hydrogen, halo, —CN, —$C_1$-$C_{20}$ alkyl (e.g., $C_1$-$C_6$ alkyl), or —$OR^7$;

each $R^3$ and $R^4$ is independently hydrogen, —$C_1$-$C_{20}$— alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$;

$R^5$ is hydrogen or —$C_1$-$C_{20}$ alkyl (e.g., —$C_1$-$C_6$ alkyl);

$R^6$ is halo, —CN, —$C_1$-$C_{20}$ alkyl (e.g., —$C_1$-$C_6$ alkyl), —$OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$;

$R^7$ is hydrogen, —$C_1$-$C_{20}$ alkyl (e.g., —$C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$;

each $R^8$ is independently —$C_1$-$C_{20}$ alkyl (e.g., —$C_1$-$C_6$ alkyl), —$C_1$-$C_{20}$ heteroalkyl, —C(O)—$C_1$-$C_{20}$ alkyl, —OC(O)—$C_1$-$C_{20}$ alkyl (e.g., —$C_1$-$C_6$ alkyl), —C(O)O—$C_1$-$C_{20}$ alkyl (e.g., —$C_1$-$C_6$ alkyl), —OC(O)O—$C_1$-$C_{20}$ alkyl (e.g., —$C_1$-$C_6$ alkyl), —C(O)N($R^5$)—$C_1$-$C_{20}$ alkyl (e.g., —$C_1$-$C_6$ alkyl), —N($R^5$)C(O)—$C_1$-$C_{20}$ alkyl (e.g., —$C_1$-$C_6$ alkyl), —OC(O)N($R^5$)—$C_1$-$C_{20}$ alkyl (e.g., —$C_1$-$C_6$ alkyl), —O-aryl, —O— heteroaryl, —C(O)-aryl, —C(O)-heteroaryl, —OC(O)-aryl, —C(O)O-aryl, —OC(O)— heteroaryl, —C(O)O-heteroaryl, —C(O)O-aryl, —C(O)O-heteroaryl, —C(O)N($R^5$)-aryl, —C(O)N($R^5$)-heteroaryl, —N($R^5$)C(O)-aryl, —N($R^5$)$_2$C(O)-aryl, or —N($R^5$)C(O)-heteroaryl, —S(O)$_2$N($R^5$)-aryl, wherein each alkyl, heteroalkyl, aryl, and heteroaryl is optionally substituted by one or more $R^9$;

each $R^9$ is independently —$C_1$-$C_{20}$ alkyl, —O—$C_1$-$C_{20}$ alkyl, —$C_1$-$C_{20}$ heteroalkyl, halo, —CN, —OH, oxo, aryl, heteroaryl, —O-aryl, or —O-heteroaryl; and each $R^{16}$ is independently, —$C_1$-$C_{20}$ alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), C(O)N($R^4$)$_2$ cycloalkyl, heterocyclyl, aryl, or heteroaryl.

In another aspect, the present disclosure features a method of inducing an immune response in a subject, comprising administering to the subject a therapeutically effective amount of a compound of Formula (I),

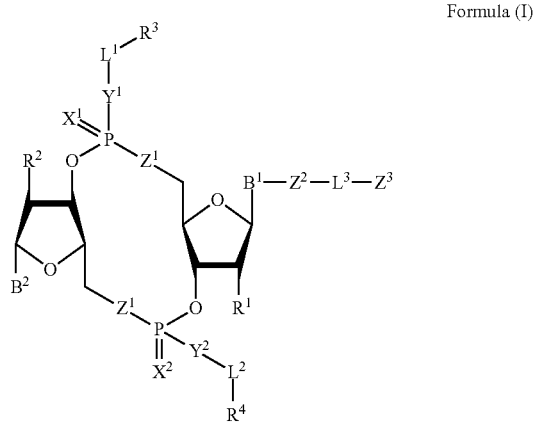

Formula (I)

or a pharmaceutically acceptable salt or stereoisomer thereof,
wherein:
each of $B^1$ and $B^2$ is independently a purinyl nucleobase or pyrimidinyl nucleobase;
each of $X^1$ and $X^2$ is independently O or S;
each of $Y^1$ and $Y^2$ is independently O, S, or $N(R^5)$;
each of $Z^1$ is independently O or S;
$Z^2$ is —O—, —$N(R^5)$—, —S—, —C(O)—, —C(O)N$(R^5)$—, —OC(O)N$(R^5)$—, —$N(R^5)$C(O)O—, -aryl-, -heteroaryl-, —S(O)—, —S(O)$_2$—, —S(O)N$(R^5)$—, —S(O)$_2$N$(R^5)$— or —N$(R^5)$S(O)—;
$Z^3$ is hydrogen, heterocyclyl, heterocyclyl-$C_1$-$C_{20}$-alkylene-$Q^1$, —OH, —$N(R^5)_2$, $SR^5$, —CHO, —C(O)N$(R^5)_2$, —OC(O)N$(R^5)_2$, —N$(R^5)$C(O)O$R^5$, aryl, heteroaryl, —S(O)$R^5$, —S(O)$_2R^5$, —S(O)N$(R^5)_2$, —S(O)$_2$N$(R^5)_2$, —N$(R^5)$S(O)$R^5$, —OSi($C_1$-$C_4$ alkyl)$_3$, or —C(O)$C_2$-$C_6$ alkenyl (e.g., —$C_2$-$C_4$ alkenyl);
$L^1$ is —$C_1$-$C_6$— alkylene (e.g., $C_1$-$C_3$ alkylene) or —$C_1$-$C_6$— heteroalkylene (e.g., —$C_1$-$C_3$ heteroalkylene);
$L^2$ is absent, —$C_1$-$C_6$— alkylene (e.g., —$C_1$-$C_3$— alkylene) or —$C_1$-$C_6$— heteroalkylene, wherein each alkylene and hetero alkylene is optionally substituted with one or more $R^6$;
$L^3$ is oligopeptide-C(O)—, oligopeptide-aryl-$C_1$-$C_6$-alkylene-, oligopeptide-aryl-$C_1$-$C_6$-heteroalkylene, oligopeptide-aryl-$C_1$-$C_6$-alkylene-C(O)—, oligopeptide-$C_1$-$C_6$-alkylene-C(O)—, oligopeptide-$C_1$-$C_6$-heteroalkylene-C(O)—, —$C_1$-$C_{40}$— alkylene (e.g., —$C_1$-$C_{20}$— alkylene), —$C_1$-$C_{40}$— heteroalkylene (e.g., —$C_1$-$C_{20}$— heteroalkyl), —$C_1$-$C_{40}$— alkenylene (e.g., —$C_2$-$C_{20}$— alkenylene), or —$C_1$-$C_{40}$-alkynylene (e.g., —$C_2$-$C_{20}$— alkynylene), wherein the oligopeptide is optionally substituted by one or more $R^{14}$;
Q is C(O), C(S), or CH$_2$;
each of $R^1$ and $R^2$ is independently hydrogen, halo, —CN, —$C_1$-$C_{20}$ alkyl (e.g., —$C_1$-$C_6$ alkyl), or $OR^7$;
each $R^3$ and $R^4$ is independently hydrogen, —$C_1$-$C_{20}$— alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$;
$R^5$ is hydrogen or —$C_1$-$C_{20}$ alkyl (e.g., —$C_1$-$C_6$ alkyl);
$R^6$ is halo, —CN, —$C_1$-$C_{20}$ alkyl (e.g., —$C_1$-$C_6$ alkyl), —$OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$;
$R^7$ is hydrogen, —$C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$;
each $R^8$ is independently —$C_1$-$C_{20}$ alkyl (e.g., —$C_1$-$C_6$ alkyl), —$C_1$-$C_{20}$ heteroalkyl, —C(O), —$C_1$-$C_{20}$ alkyl, —OC(O)—$C_1$-$C_{20}$ alkyl (e.g., —$C_1$-$C_6$ alkyl), —C(O)O—$C_1$-$C_{20}$ alkyl (e.g., —$C_1$-$C_6$ alkyl), —OC(O)O—$C_1$-$C_{20}$ alkyl (e.g., —$C_1$-$C_6$ alkyl), —C(O)N$(R^5)$—$C_1$-$C_{20}$ alkyl (e.g., —$C_1$-$C_6$ alkyl), —N$(R^5)$C(O)—$C_1$-$C_{20}$ alkyl (e.g., —$C_1$-$C_6$ alkyl), —OC(O)N$(R^5)$—$C_1$-$C_{20}$ alkyl (e.g., —$C_1$-$C_6$ alkyl), —O-aryl, —O-heteroaryl, —C(O)-aryl, —C(O)-heteroaryl, —OC(O)-aryl, —C(O)O-aryl, —OC(O)-heteroaryl, —C(O)O-heteroaryl, —C(O)O-aryl, —C(O)O-heteroaryl, —C(O)N$(R^5)$-aryl, —C(O)N$(R^5)$-heteroaryl, —N$(R^5)$C(O)-aryl, —N$(R^5)_2$C(O)-aryl, or —N$(R^5)$C(O)-heteroaryl, —S(O)$_2$N$(R^5)$-aryl, wherein each alkyl, heteroalkyl, aryl, and heteroaryl is optionally substituted by one or more $R^9$;
each $R^9$ is independently —$C_1$-$C_{20}$ alkyl, —O—$C_1$-$C_{20}$ alkyl, —$C_1$-$C_{20}$ heteroalkyl, halo, —CN, —OH, oxo, aryl, heteroaryl, —O-aryl, or —O-heteroaryl;
$Q^1$ is C(O), C(S), or CH$_2$; and
each $R^{16}$ is independently, —$C_1$-$C_{20}$ alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), C(O)N$(R^4)_2$ cycloalkyl, heterocyclyl, aryl, or heteroaryl.

In another aspect, the present disclosure features a method of inducing an immune response in a subject, comprising administering to the subject a therapeutically effective amount of a compound of Formula (II),

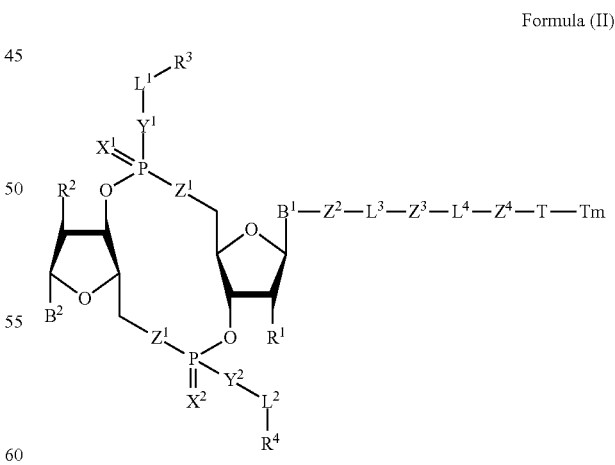

Formula (II)

or a pharmaceutically acceptable salt or stereoisomer thereof,
wherein:
Tm is a targeting moiety;
each of $B^1$ and $B^2$ is independently a purinyl nucleobase or pyrimidinyl nucleobase;

each of $X^1$ and $X^2$ is independently O or S;
each of $Y^1$ and $Y^2$ is independently O, S, or $N(R^5)$;
each of $Z^1$ is independently O or S;
$Z^2$ is —O—, —$N(R^5)$—, —S—, —C(O)—, —C(O)N($R^5$)—, —OC(O)N($R^5$)—, —$N(R^5)$C(O)O—, -aryl-, -heteroaryl-, —S(O)—, —S(O)$_2$—, —S(O)N($R^5$)—, —S(O)$_2$N($R^5$)— or —N($R^5$)S(O)—;
$Z^3$ is absent, hydrogen, heterocyclyl, heterocyclyl-$C_1$-$C_{20}$-alkylene-$Q^1$, —OH, —N($R^5$)$_2$, SR$^5$, —CHO, —C(O)N($R^5$)$_2$, —OC(O)N($R^5$)$_2$, —N($R^5$)C(O)OR$^5$, aryl, heteroaryl, —S(O)R$^5$, —S(O)$_2$R$^5$, —S(O)N($R^5$)$_2$, —S(O)$_2$N($R^5$)$_2$, —N(R')S(O)R$^5$, —OSi($C_1$-$C_4$ alkyl)$_3$, or —C(O)$C_2$-$C_6$ alkenyl (e.g., —$C_2$-$C_4$ alkenyl);
$Z^4$ is a self-immolative group or absent:
T is a absent or spacer group;
each $L^1$ and $L^2$ is absent, —$C_1$-$C_6$— alkylene (e.g., —$C_1$-$C_3$— alkylene) or —$C_1$-$C_6$-heteroalkylene, wherein each alkylene and heteroalkyl is optionally substituted with one or more $R^6$;
$L^3$ is oligiopeptide-C(O)—, oligiopeptide-aryl-$C_1$-$C_6$-alkylene-, oligiopeptide-aryl-$C_1$-$C_6$-alklyene-C(O)—, oligiopeptide-aryl-$C_1$-$C_6$-heteroalkylene, oligiopeptide-$C_1$-$C_6$-alkylene-C(O)—, oligiopeptide-$C_1$-$C_6$-heteroalkylene-C(O)—, —$C_1$-$C_{40}$-alkylene (e.g., —$C_1$-$C_{20}$— alkylene), —$C_1$-$C_{40}$— heteroalkylene (e.g., —$C_1$-$C_{20}$-heteroalkyl), —$C_1$-$C_{40}$— alkenylene (e.g., —$C_2$-$C_{20}$— alkenylene), or —$C_1$-$C_{40}$-alkynylene (e.g., —$C_2$-$C_{20}$— alkynylene), wherein the oligopeptide is optionally substituted by one or more $R^{14}$;
$L^4$ is absent or a linker connecting $Z^3$ and $Z^4$;
$Q^1$ is C(O), C(S), or CH$_2$;
each of $R^1$ and $R^2$ is independently hydrogen, halo, —CN, —$C_1$-$C_{20}$ alkyl (e.g., $C_1$-$C_6$ alkyl), or —OR$^7$;
each $R^3$ and $R^4$ is independently hydrogen, —$C_1$-$C_{20}$— alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$;
$R^5$ is hydrogen or —$C_1$-$C_{20}$ alkyl (e.g., —$C_1$-$C_6$ alkyl);
$R^6$ is halo, —CN, —$C_1$-$C_{20}$ alkyl (e.g., —$C_1$-$C_6$ alkyl), —OR$^7$, oxo, cycloalkyl, heterocyclyl, aryl, or heteroaryl, wherein each alkyl, cycloalkyl, heterocyclyl, aryl, and heteroaryl is optionally substituted with one or more $R^9$;
$R^7$ is hydrogen, —$C_1$-$C_{20}$ alkyl (e.g., —$C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$;
each $R^8$ is independently —$C_1$-$C_{20}$ alkyl (e.g., —$C_1$-$C_6$ alkyl), —$C_1$-$C_{20}$ heteroalkyl, —C(O)—$C_1$-$C_{20}$ alkyl, —OC(O)—$C_1$-$C_{20}$ alkyl (e.g., —$C_1$-$C_6$ alkyl), —C(O)O—$C_1$-$C_{20}$ alkyl (e.g., —$C_1$-$C_6$ alkyl), —OC(O)O—$C_1$-$C_{20}$ alkyl (e.g., —$C_1$-$C_6$ alkyl), —C(O)N($R^5$)—$C_1$-$C_{20}$ alkyl (e.g., —$C_1$-$C_6$ alkyl), —N($R^5$)C(O)—$C_1$-$C_{20}$ alkyl (e.g., —$C_1$-$C_6$ alkyl), —OC(O)N($R^5$)—$C_1$-$C_{20}$ alkyl (e.g., —$C_1$-$C_6$ alkyl), —O-aryl, —O— heteroaryl, —C(O)-aryl, —C(O)-heteroaryl, —OC(O)-aryl, —C(O)O-aryl, —OC(O)— heteroaryl, —C(O)O-heteroaryl, —C(O)O-aryl, —C(O)O-heteroaryl, —C(O)N($R^5$)-aryl, —C(O)N($R^5$)-heteroaryl, —N($R^5$)C(O)-aryl, —N($R^5$)$_2$C(O)-aryl, or —N($R^5$)C(O)-heteroaryl, —S(O)$_2$N($R^5$)-aryl, wherein each alkyl, heteroalkyl, aryl, and heteroaryl is optionally substituted by one or more $R^9$;
each $R^9$ is independently —$C_1$-$C_{20}$ alkyl, —O—$C_1$-$C_{20}$ alkyl, —$C_1$-$C_{20}$ heteroalkyl, halo, —CN, —OH, oxo, aryl, heteroaryl, —O-aryl, or —O-heteroaryl; and each $R^{16}$ is independently, —$C_1$-$C_{20}$ alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), C(O)N($R^4$)$_2$ cycloalkyl, heterocyclyl, aryl, or heteroaryl.

In some embodiments, the immune response comprises antitumoral immunity. In some embodiments, the immune response comprises induction of a PRR (e.g., STING, RIG-I, MDA5).

DETAILED DESCRIPTION OF THE DISCLOSURE

The present disclosure relates to methods of activating and/or inducing the expression of PRRs (e.g., STING) in a subject, in particular for the treatment of a microbial infection or a proliferative disease (e.g., cancer). In some embodiments, the method comprises administration of a compound of Formula (I) or pharmaceutically acceptable salt thereof. In some embodiments, the method comprises administration of a compound of Formula (II) or pharmaceutically acceptable salt thereof. It is to be noted that induction of any PRR with these compounds can stimulate interferon and/or NF-KB production which can induce the expression of a variety of PRRs which are inducible genes by feedback mechanism.

Definitions

As used herein, the articles "a" and "an" refer to one or to more than one (e.g., to at least one) of the grammatical object of the article.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

As used herein, the term "acquire" or "acquiring" as the terms are used herein, refer to obtaining possession of a physical entity (e.g., a sample, e.g., blood sample or liver biopsy specimen), or a value, e.g., a numerical value, by "directly acquiring" or "indirectly acquiring" the physical entity or value. "Directly acquiring" means performing a process (e.g., an analytical method) to obtain the physical entity or value. "Indirectly acquiring" refers to receiving the physical entity or value from another party or source (e.g., a third party laboratory that directly acquired the physical entity or value). Directly acquiring a value includes performing a process that includes a physical change in a sample or another substance, e.g., performing an analytical process which includes a physical change in a substance, e.g., a sample, performing an analytical method, e.g., a method as described herein, e.g., by sample analysis of bodily fluid, such as blood by, e.g., mass spectroscopy, e.g., LC-MS.

As used herein, the terms "induce" or "induction of" refer to the increase or enhancement of a function, e.g., the increase or enhancement of the expression of a pattern recognition receptor (e.g, STING). In some embodiments, "induction of PRR expression" refers to induction of transcription of PRR RNA, e.g., STING RNA (e.g., mRNA, e.g., an increase or enhancement of), or the translation of a PRR protein, e.g., the STING protein (e.g., an increase or enhancement of). In some embodiments, induction of PRR expression (e.g., STING expression) refers to the increase or enhancement of the concentration of a PRR RNA, e.g., or STING RNA (e.g., mRNA) or the STING protein, e.g., in a cell. In some embodiments, induction of PRR expression (e.g., STING expression) refers to the increase of the number of copies of PRR RNA, e.g., STING RNA (e.g., mRNA)

or PRR protein, e.g., the STING protein, e.g., in a cell. In some embodiments, to induce expression of a PRR (e.g., STING) may refer to the initiation of PRR RNA (e.g., STING RNA (e.g., mRNA)) or transcription or PRR protein (e.g., STING protein) translation. In some embodiments, to induce expression of a PRR (e.g., STING) may refer to an increase in the rate of PRR RNA (e.g., STING RNA (e.g., mRNA)) transcription or an increase in the rate of PRR protein (e.g., STING protein) expression.

As used herein, the terms "activate" or "activation" refer to the stimulation or triggering of a function, e.g., of a downstream pathway, e.g., a downstream signaling pathway. In some embodiments, activation of a pattern recognition receptor (PRR) (e.g., STING) refers to the stimulation of a specific protein or pathway, e.g., through interaction with a downstream signaling partner (e.g., IFN-β promoter stimulator 1 (IPS-1), IRF3, IRF7, NF-κB, interferons (e.g., IFN-α or IFN-β) and/or cytokines). In some embodiments, activation is distinct from the induction of expression of a PRR. In some embodiments, a PRR may be activated without resulting in an induction of PRR expression (e.g., expression of STING). In some embodiments, activation may include induction of expression of a PRR (e.g., STING). In some embodiments, activation of a PRR may trigger the induction of expression of a PRR (e.g., STING) by about 0.1%, about 0.5%, about 1%, about 5%, about 10%, about 15%, about 20%, about 25%, about 30%, about 40%, about 50%, about 60%, about 70%, about 80%, about 90%, about 95%, or more compared to a reference standard (e.g., basal expression levels of a PRR (e.g., STING)).

As used herein, an amount of a compound, conjugate, or substance effective to treat a disorder (e.g., a disorder described herein), "therapeutically effective amount," "effective amount" or "effective course" refers to an amount of the compound, substance, or composition which is effective, upon single or multiple dose administration(s) to a subject, in treating a subject, or in curing, alleviating, relieving or improving a subject with a disorder (e.g., a microbial infection) beyond that expected in the absence of such treatment.

As used herein, the terms "prevent" or "preventing" as used in the context of a disorder or disease, refer to administration of an agent to a subject, e.g., the administration of a compound of the present disclosure (e.g., compound of Formula (I)) to a subject, such that the onset of at least one symptom of the disorder or disease is delayed as compared to what would be seen in the absence of administration of said agent.

As used herein, the terms "reference treatment" or "reference standard" refer to a standardized level or standardized treatment that is used as basis for comparison. In some embodiments, the reference standard or reference treatment is an accepted, well known, or well characterized standard or treatment in the art. In some embodiments, the reference standard describes an outcome of a method described herein. In some embodiments, the reference standard describes a level of a marker (e.g., a level of induction of a PRR, e.g., STING) in a subject or a sample, e.g., prior to initiation of treatment, e.g., with a compound or composition described herein. In some embodiments, the reference standard describes a measure of the presence of, progression of, or severity of a disease or the symptoms thereof, e.g., prior to initiation of treatment, e.g., with a compound or composition described herein.

As used herein, the term "subject" is intended to include human and non-human animals. Exemplary human subjects include a human patient having a disorder, e.g., a disorder described herein, or a normal subject. The term "non-human animals" includes all vertebrates, e.g., non-mammals (such as chickens, amphibians, reptiles) and mammals, such as non-human primates, domesticated and/or agriculturally useful animals, e.g., sheep, dogs, cats, cows, pigs, etc. In exemplary embodiments of the disclosure, the subject is a woodchuck (e.g., an Eastern woodchuck (*Marmota monax*)).

As used herein, the terms "treat" or "treating" a subject having a disorder or disease refer to subjecting the subject to a regimen, e.g., the administration of a compound of Formula (I) or pharmaceutically acceptable salt thereof, or a composition comprising Formula (I) or pharmaceutically acceptable salt thereof, such that at least one symptom of the disorder or disease is cured, healed, alleviated, relieved, altered, remedied, ameliorated, or improved. Treating includes administering an amount effective to alleviate, relieve, alter, remedy, ameliorate, improve or affect the disorder or disease, or the symptoms of the disorder or disease. The treatment may inhibit deterioration or worsening of a symptom of a disorder or disease.

As used herein, the term "Cmd" refers to the word "compound" or "Compound", and all of the terms are used interchangeably.

Numerous ranges, e.g., ranges for the amount of a drug administered per day, are provided herein. In some embodiments, the range includes both endpoints. In other embodiments, the range excludes one or both endpoints. By way of example, the range can exclude the lower endpoint. Thus, in such an embodiment, a range of 250 to 400 mg/day, excluding the lower endpoint, would cover an amount greater than 250 that is less than or equal to 400 mg/day.

The term "alkyl," as used herein, refers to a monovalent saturated, straight- or branched-chain hydrocarbon such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Examples of alkyl groups include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, and the like.

The terms "alkenyl" and "alkynyl" are art-recognized and refer to unsaturated aliphatic groups analogous in length and possible substitution to the alkyls described above, but that contain at least one double or triple bond, respectively. Exemplary alkenyl groups include, but are not limited to, —CH=CH$_2$ and —CH$_2$CH=CH$_2$.

The term "alkylene" refers to the diradical of an alkyl group.

The terms "alkenylene" and "alkynylene" refer to the diradicals of an alkenyl and an alkynyl group, respectively.

The term "methylene unit" refers to a divalent —CH$_2$— group present in an alkyl, alkenyl, alkynyl, alkylene, alkenylene, or alkynylene moiety.

The term "carbocyclic ring system", as used herein, means a monocyclic, or fused, spiro-fused, and/or bridged bicyclic or polycyclic hydrocarbon ring system, wherein each ring is either completely saturated or contains one or more units of unsaturation, but where no ring is aromatic.

The term "carbocyclyl" refers to a radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

The term "aromatic ring system" is art-recognized and refers to a monocyclic, bicyclic or polycyclic hydrocarbon ring system, wherein at least one ring is aromatic.

The term "aryl" refers to a radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

The term "heteroalkyl" refers to an "alkyl" moiety wherein at least one of the carbone molecules has been replaced with a heteroatom such as O, S, or N.

The term "heteroaromatic ring system" is art-recognized and refers to monocyclic, bicyclic or polycyclic ring system wherein at least one ring is both aromatic and comprises a heteroatom; and wherein no other rings are heterocyclyl (as defined below). In certain instances, a ring which is aromatic and comprises a heteroatom contains 1, 2, 3, or 4 independently selected ring heteroatoms in such ring.

The term "heteroaryl" refers to a radical of a heteroaromatic ring system. Representative heteroaryl groups include ring systems where (i) each ring comprises a heteroatom and is aromatic, e.g., imidazolyl, oxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl. In certain embodiments, the heteroaryl is a monocyclic or bicyclic ring, wherein each of said rings contains 5 or 6 ring atoms where 1, 2, 3, or 4 of said ring atoms are a heteroatom independently selected from N, O, and S.

The term "heterocyclic ring system" refers to monocyclic, or fused, spiro-fused, and/or bridged bicyclic and polycyclic ring systems where at least one ring is saturated or partially unsaturated (but not aromatic) and comprises a heteroatom. A heterocyclic ring system can be attached to its pendant group at any heteroatom or carbon atom that results in a stable structure and any of the ring atoms can be optionally substituted.

The term "heterocyclyl" refers to a radical of a heterocyclic ring system. Representative heterocyclyls include ring systems in which (i) every ring is non-aromatic and at least one ring comprises a heteroatom, e.g., tetrahydrofuranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c]pyridine, and 1,2,3,4-tetrahydro-2,6-naphthyridine. In certain embodiments, the heterocyclyl is a monocyclic or bicyclic ring, wherein each of said rings contains 3-7 ring atoms where 1, 2, 3, or 4 of said ring atoms are a heteroatom independently selected from N, O, and S.

The term "saturated heterocyclyl" refers to a radical of heterocyclic ring system wherein every ring is saturated, e.g., tetrahydrofuran, tetrahydro-2H-pyran, pyrrolidine, piperidine and piperazine.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

The term "nucleobase" as used herein, is a nitrogen-containing biological compound found linked to a sugar within a nucleoside—the basic building blocks of deoxyribonucleic acid (DNA) and ribonucleic acid (RNA). The primary, or naturally occurring, nucleobases are cytosine (DNA and RNA), guanine (DNA and RNA), adenine (DNA and RNA), thymine (DNA) and uracil (RNA), abbreviated as C, G, A, T, and U, respectively. Because A, G, C, and T appear in the DNA, these molecules are called DNA-bases; A, G, C, and U are called RNA-bases. Adenine and guanine belong to the double-ringed class of molecules called purines (abbreviated as R). Cytosine, thymine, and uracil are all pyrimidines. Other nucleobases that do not function as normal parts of the genetic code are termed non-naturally occurring.

As described herein, compounds of the disclosure may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

As used herein, the definition of each expression, e.g., alkyl, m, n, etc., when it occurs more than once in any structure, is intended to be independent of its definition elsewhere in the same structure.

As described herein, compounds of the disclosure may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

The term "ADC" refers to an antibody drug conjugate.

As used herein, the term "Linker", "Linker Unit", or "link" means a chemical moiety comprising a covalent bond or a chain of atoms that covalently attaches two groups, e.g., an antibody to a drug moiety.

The term "monoclonal antibody" refers to a homogeneous antibody population involved in the highly specific recognition and binding of a single antigenic determinant or epitope. This is in contrast to polyclonal antibodies that typically include different antibodies directed against a variety of different antigenic determinants. The term "monoclonal antibody" includes 33 antibody fragments (such as Fab, Fab', F(ab')$_2$, Fd, Fv), single chain (scFv) mutants, fusion proteins including an antibody portion, and any other modified immunoglobulin molecule including an antigen recognition site as well as both intact and full-length monoclonal antibodies, but are not limited thereto. Additionally, "monoclonal antibody" refers to such antibodies made in any number of methods including but not limited to hybridoma, phage selection, recombinant expression, and transgenic animals.

The term "humanized antibody" refers to forms of non-human (e.g., murine) antibodies that are specific immunoglobulin chains, chimeric immunoglobulins, or fragments thereof that contain minimal non-human (e.g., murine) sequences. In general, humanized antibodies are human immunoglobulins in which residues from complementary determining region (CDR) are replaced by residues from CDR of a non-human species (e.g., mouse, rat, rabbit, and hamster) having the desired specificity, affinity, and capability (ref: Jones et al., 1986, Nature, 321:522-525; Riechmann et al., 1988, Nature, 332:323-327: Verhoeyen et al., 1988, Science, 239:1534-1536). In some instances, Fv framework region (FR) residues of a human immunoglobulin are replaced with the corresponding residues in an antibody from a non-human species having the desired specificity, affinity, and/or binding capability. The humanized 34 antibody may be further modified by the substitution of additional residues either in the Fv framework region and/or within the replaced non-human residues to refine and optimize antibody specificity, affinity, and/or binding capability. In general, the humanized antibody includes substantially all of at least one, and typically two or three, variable domains containing all or substantially all of the CDRs that correspond to the non-human immunoglobulin whereas all or substantially all of the framework regions (FRs) have those of a human immunoglobulin consensus sequence. The humanized antibody may also include at least a portion of an immunoglobulin constant region or domain (Fc), typically that of a human immunoglobulin. Examples of methods used to generate humanized antibodies are described in U.S. Pat. No. 5,225,539.

The term "human antibody" as used herein refers to an antibody produced by a human or an antibody having an amino acid sequence corresponding to an antibody produced by a human using any technique known in the art. This definition of the human antibody includes intact or full length antibodies, fragments thereof, and/or antibodies including at least one human heavy and/or light chain polypeptide such as, for example, an antibody including murine light chain and human heavy chain polypeptides.

The term "chimeric antibody" refers to an antibody wherein an amino acid sequence of an immunoglobulin molecule is derived from two or more species. In general, variable regions of both light and heavy chains correspond to variable regions of antibodies derived from one species of mammals (e.g., mouse, rat, rabbit, etc) with the desired specificity, affinity, and capability, while constant regions are homologous to the sequences in antibodies derived from another species (usually human) to avoid eliciting an immune response in that species.

The term "self-eliminating linker" or "self-immolative linker" refers to a temporary extender, spacer, or placeholder unit attaching two or more molecules together by chemical bonds that are cleaved under defined conditions to release the two molecules. In general, a self-eliminating or self-immolative linker may be linear or branched, and may link two or more of the same molecules together, or may link two or more different molecules together. A self-immolative moiety may be defined as a bifunctional chemical group which is capable of covalently linking together two spaced chemical moieties into a normally stable molecule, releasing one of said spaced chemical moieties from the molecule by means of enzymatic cleavage; and following said enzymatic cleavage, spontaneously cleaving from the remainder of the bifunctional chemical group to release the other of said spaced chemical moieties. In some embodiments, the self-immolative refers to a heterocyclic self-immolative moiety. Exemplary self-immolative linkers include His-Ala, p-aminobenzyloxycarbonyl (PABC), 2,4-bis(hydroxymethyl)aniline, —NH—(CH$_2$)$_4$—C(O)— and —NH—(CH$_2$)$_3$—C(O)—.

The term "cleaveable group" is refers to a moiety that is unstable in vivo. Preferably, the "cleaveable group" allows for activation of the marker or therapeutic agent by cleaving the marker or agent from the rest of the conjugate. Operatively defined, the linker is preferably cleaved in vivo by the biological environment. The cleavage may come from any process without limitation, e.g., enzymatic, reductive, pH, etc. Preferably, the cleaveable group is selected so that activation occurs at the desired site of action, which can be a site in or near the target cells (e.g., carcinoma cells) or tissues such as at the site of therapeutic action or marker activity. Such cleavage may be enzymatic and exemplary enzymatically cleaveable groups include natural amino acids or peptide sequences that end with a natural amino acid, and are attached at their carboxyl terminus to the linker. While the degree of cleavage rate enhancement is not critical to the invention, preferred examples of cleaveable linkers are those in which at least about 10% of the cleaveable groups are cleaved in the blood stream within 24 hours of administration, most preferably at least about 35%.

The term "spacer group" refers any chemical group designed to facilitate the attachment of the drug conjugates to an antibody, e.g., in order to overcome steric hinderance.

The term "targeting moiety" as used herein refers to a moiety (e.g., an antibody, a hormone, a hormone derivative, a folic acid, a folic acid derivative, a biotin, a small molecule, an oligopeptide, a sigma-2-ligand, or a sugar) that serves to target or direct the conjugate to a particular location (e.g., cell type, or diseased tissue) or interaction (e.g., a specific binding event).

Pattern Recognition Receptors

The disclosure presented herein features methods for the activation and induction of PRR expression (e.g., STING expression) in a subject, e.g., a subject with a microbial infection (e.g., a viral infection, bacterial infection, fungal infection, or parasitic infection) or a proliferative disease (e.g., cancer).

Pattern recognition receptors (PRRs) are a broad class of proteins which recognize pathogen-associated molecular patterns (PAMPs) conserved within pathogenic invaders. PAMPs are typically products of biosynthetic pathways that are essential to the survival and/or infectivity of the pathogen, e.g., lipopolysaccharides, glycoproteins, and nucleic acids. Recognition of PAMPs by their cognate PRRs activates signaling pathways that result in the production of immune defense factors such as pro-inflammatory and anti-inflammatory cytokines, type I interferons (IFN-α, IFN-3), and/or interferon stimulated genes (ISGs). It is well known that induction of innate immune signaling also results in the activation of T cell responses as well as the induction of adaptive immunity. These downstream immune effects are essential for clearance of the virus through apoptosis and killing of infected cells through cytotoxic T lymphocytes and other defense mechanisms. It is also well known that interferons act on ISRE (interferon response elements) that can trigger the production of ISGs, which play an important role in antiviral cellular defense.

The stimulator of interferon genes (STING) is a cytosolic microbial-derived DNA sensor that has been shown to be particularly sensitive to double-stranded DNA and cyclic dinucleotides (e.g., cyclic di-GMP) (Burdette, D. L. and Vance, R. E. (2013) *Nat Immunol* 14:19-26). Two molecules of STING form a homodimer mediated by an α-helix present in the C-terminal dimerization domain, and molecular binding studies have revealed that each STING dimer binds one molecule of microbial nucleic acids, e.g., DNA or a cyclic dinucleotide. Upon ligand binding, STING activates the innate immune response through interaction with RIG-I and IPS-1, resulting in interferon production (e.g., IFN-α and IFN-β) and other downstream signaling events. Since its discovery, STING has been shown to function as a critical sensor of viruses (e.g., adenovirus, herpes simplex virus, hepatitis B virus, vesicular stomatitis virus, hepatitis C virus), bacteria (e.g., *Listeria monocytogenes, Legionella pneumopholia, Mycobacterium tuberculosis*) and protozoa (*Plasmodium falciparum, Plasmodium berghei*). In addition, STING has been shown to play a major role in the innate immune response against tumor antigens, driving dendritic cell activation and subsequent T cell priming in several cancers (Woo, S. R. et al. *Trends in Immunol* (2015) 36:250-256).

Another class of PRRs includes RIG-I, which is the founding member of a family of PRRs termed RIG-I-like receptors (RLRs) that primarily detect RNA derived from foreign sources. It is a critical sensor of microbial infection (e.g., viral infection) in most cells and is constitutively expressed at low levels in the cytosol. After ligand binding, the expression of RIG-I is rapidly enhanced, leading to increased RIG-I concentrations in the cell (Jensen, S. and Thomsen, A. R. *J Virol* (2012) 86:2900-2910; Yoneyama M. et al. *Nat Immunol* (2004) 5:730-737). RIG-I is an ATP-dependent helicase containing a central DExD/H box ATPase domain and tandem N-terminal caspase-recruiting domains (CARDs) that mediate downstream signaling. The C-terminus of RIG-I comprises an ssRNA/dsRNA-binding domain that when unbound acts to silence CARD function at the N-terminus. Without wishing to be bound by theory, it is believed that upon recognition of target RNA structures, two N-terminal CARDs are exposed, allowing for interaction with the CARD of a downstream binding partner, IFN-β promoter stimulator 1 (IPS-1), also known as mitochondrial antiviral signaling molecule (MAVS) and CARDIF. This interaction in turn triggers further downstream signaling, such as induction of IRF3, IRF7, NF-κB, IFNs, and cytokine production that results in the initiation of the host immune response.

Other RLRs are homologous to RIG-I and function in a similar manner, including MDA5, LGP2, and RNase L. MDA5 is highly homologous to RIG-I, and has been shown to be crucial for triggering a cytokine response upon infection with picornaviruses (e.g., encephalomyocarditis virus (EMCV), Theiler's virus, and Mengo virus), Sendai virus, rabies virus, West Nile virus, rabies virus, rotavirus, murine hepatitis virus, and murine norovirus. LPG2 lacks a CARD domain found in RIG-I and MDA5, which is responsible for direct interaction with IPS-1 to initiate downstream signaling. As such, LPG2 is believed to behave as a modulator of the innate immune response in conjunction with other CARD-bearing RLRs such as RIG-I and MDA5.

Another class of PRRs encompasses the nucleotide-binding and oligomerization domain (NOD)-like receptors, or NLR family (Caruso, R. et al, *Immunity* (2014) 41:898-908), which includes the microbial sensor NOD2. NOD2 is composed of an N-terminal CARD, a centrally-located nucleotide-binding oligomerization domain, and a C-terminal leucine rich repeat domain that is responsible for binding microbial PAMPs, such as bacterial peptidoglycan fragments and microbial nucleic acids. Ligand binding activates NOD2 and is believed to drive interaction with the CARD-containing kinase RIPK2, which in turn activates a number of downstream proteins including NF-κB, MAPK, IRF7, and IRF3, the latter of which results in the induction of type 1 interferons. NOD2 is expressed in a diverse set of cell types, including macrophages, dendritic cells, paneth cells, epithelial cells (e.g., lung epithelial cells, intestinal epithelia), and osteoblasts. NOD2 has been established as a sensor of infection by variety of pathogenic invaders, such as protozoa (e.g., *Toxoplasma gondii* and *Plasmodium berghei*), bacteria (e.g., *Bacillus anthracis, Borrelia burgdorferi, Burkholderia pseudomallei, Helicobacter hepaticus, Legionella pneumophilia, Mycobacterium tuberculosis, Propionibacterium acne, Porphyromonas gingivahs, Salmonella enterica,* and *Streptococcus pneumonia*), and viruses (e.g., respiratory syncytial virus and murine norovirus-1) (Moreira, L. O. and Zamboni, D. S. *Front Immunol* (2012) 3:1-12). Recent work has shown that mutation of NOD2 may contribute to inflammatory diseases such as Crohn's disease, resulting in an aberrant inflammatory response upon stimulation.

Compounds

The present disclosure features compounds and methods for the induction of PRR expression (e.g., STING expression) in a subject (e.g., a subject with a microbial infection (e.g., a viral infection, bacterial infection, fungal infection, or parasitic infection) or a proliferative disease (e.g., cancer)), comprising administration of a compound of Formula (I) or a prodrug or pharmaceutically acceptable salt thereof.

In some embodiments, the present disclosure features a compound of Formula (I) in which the 3'-OH end of one nucleoside is joined to the 5'-OH of the second nucleoside through a linkage as shown. In some other embodiments, the 2'-OH end of one nucleoside may be joined to the 5'-OH of the second nucleoside through a linkage.

In some embodiments, the compound is a compound of Formula (I):

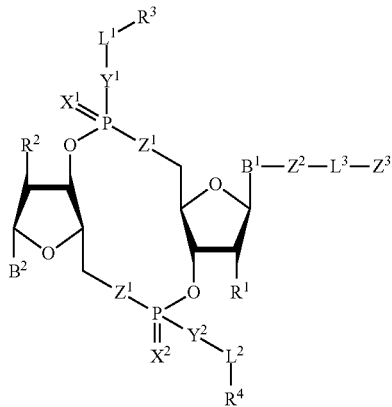

Formula (I)

or a pharmaceutically acceptable salt or stereoisomer thereof,
wherein:
each of $B^1$ and $B^2$ is independently a purinyl nucleobase or pyrimidinyl nucleobase;
each of $X^1$ and $X^2$ is independently O or S;
each of $Y^1$ and $Y^2$ is independently O, S, or $N(R^5)$;
each of $Z^1$ is independently O or S;
$Z^2$ is —O—, —$N(R^5)$—, —S—, —C(O)—, —C(O)N($R^5$)—, —OC(O)N($R^5$)—, —N($R^5$)C(O)O—, -aryl-, -heteroaryl-, —S(O)—, —S(O)$_2$—, —S(O)N($R^5$)—, —S(O)$_2$N($R^5$)— or —N($R^5$)S(O)—;
$Z^3$ is hydrogen, heterocyclyl, heterocyclyl-$C_1$-$C_{20}$-alkylene-$Q^1$, —OH, —N($R^5$)$_2$, $SR^5$, —CHO, —C(O)N($R^5$)$_2$, —OC(O)N($R^5$)$_2$, —N($R^5$)C(O)O$R^5$, aryl, heteroaryl, —S(O)$R^5$, —S(O)$_2R^5$, —S(O)N($R^5$)$_2$, —S(O)$_2$N($R^5$)$_2$, —N($R^5$)S(O)$R^5$, —OSi($C_1$-$C_4$ alkyl)$_3$, or —C(O)$C_2$-$C_6$ alkenyl (e.g., —$C_2$-$C_4$ alkenyl);
$L^1$ is —$C_1$-$C_6$— alkylene (e.g., $C_1$-$C_3$ alkylene) or —$C_1$-$C_6$— heteroalkylene (e.g., —$C_1$-$C_3$ heteroalkylene);
$L^2$ is absent, —$C_1$-$C_6$— alkylene (e.g., —$C_1$-$C_3$— alkylene) or —$C_1$-$C_6$— heteroalkylene, wherein each alkylene and hetero alkylene is optionally substituted with one or more $R^6$;
$L^3$ is oligopeptide-C(O)—, oligopeptide-aryl-$C_1$-$C_6$-alkylene-, oligopeptide-aryl-$C_1$-$C_6$-heteroalkylene, oligopeptide-aryl-$C_1$-$C_6$-alklyene-C(O)—, oligopeptide-$C_1$-$C_6$-alkylene-C(O)—, oligopeptide-$C_1$-$C_6$-heteroalkylene-C(O)—, —$C_1$-$C_{40}$— alkylene (e.g., —$C_1$-$C_{20}$— alkylene), —$C_1$-$C_{40}$— heteroalkylene (e.g., —$C_1$-$C_{20}$— heteroalkyl), —$C_1$-$C_{40}$— alkenylene (e.g., —$C_2$-$C_{20}$— alkenylene), or —$C_1$-$C_{40}$-alkynylene (e.g., —$C_2$-$C_{20}$— alkynylene), wherein the oligopeptide is optionally substituted by one or more $R^{14}$;
Q is C(O), C(S), or CH$_2$;
each of $R^1$ and $R^2$ is independently hydrogen, halo, —CN, —$C_1$-$C_{20}$ alkyl (e.g., —$C_1$-$C_6$ alkyl), or $OR^7$;
each $R^3$ and $R^4$ is independently hydrogen, —$C_1$-$C_{20}$— alkyl (e.g., —$C_1$-$C_6$ alkyl), —$C_1$-$C_2$ heteroalkyl (e.g., —$C_1$-$C_6$ heteroalkyl), —OC(O)O$C_1$-$C_{20}$ alkyl (e.g., —$C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$;

$R^5$ is hydrogen or —$C_1$-$C_{20}$ alkyl (e.g., —$C_1$-$C_6$ alkyl);
$R^6$ is halo, —CN, —$C_1$-$C_{20}$ alkyl (e.g., —$C_1$-$C_6$ alkyl), —$OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$;
$R^7$ is hydrogen, —$C_1$-$C_{20}$ alkyl (e.g., $C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$;
each $R^8$ is independently —$C_1$-$C_{20}$ alkyl (e.g., —$C_1$-$C_6$ alkyl), —$C_1$-$C_{20}$ heteroalkyl, —C(O), —$C_1$-$C_{20}$ alkyl, —OC(O)—$C_1$-$C_{20}$ alkyl (e.g., —$C_1$-$C_6$ alkyl), —C(O)O—$C_1$-$C_{20}$ alkyl (e.g., —$C_1$-$C_6$ alkyl), —OC(O)O—$C_1$-$C_{20}$ alkyl (e.g., —$C_1$-$C_6$ alkyl), —C(O)N($R^5$)—$C_1$-$C_{20}$ alkyl (e.g., —$C_1$-$C_6$ alkyl), —N($R^5$)C(O)—$C_1$-$C_{20}$ alkyl (e.g., —$C_1$-$C_6$ alkyl), —OC(O)N(R')—$C_1$-$C_{20}$ alkyl (e.g., —$C_1$-$C_6$ alkyl), —O-aryl, —O-heteroaryl, —C(O)-aryl, —C(O)-heteroaryl, —OC(O)-aryl, —C(O)O-aryl, —OC(O)-heteroaryl, —C(O)O-heteroaryl, —C(O)O-aryl, —C(O)O-heteroaryl, —C(O)N($R^5$)-aryl, —C(O)N($R^5$)-heteroaryl, —N($R^5$)C(O)-aryl, —N($R^5$)$_2$C(O)-aryl, or —N($R^5$)C(O)-heteroaryl, —S(O)$_2$N($R^5$)-aryl, wherein each alkyl, heteroalkyl, aryl, and heteroaryl is optionally substituted by one or more $R^9$;
each $R^9$ is independently —$C_1$-$C_{20}$ alkyl, —O—$C_1$-$C_{20}$ alkyl, —$C_1$-$C_{20}$ heteroalkyl, halo, —CN, —OH, oxo, aryl, heteroaryl, —O-aryl, or —O-heteroaryl;
$Q^1$ is C(O), C(S), or CH$_2$; and
each $R^{16}$ is independently, —$C_1$-$C_{20}$ alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), C(O)N($R^4$)$_2$ cycloalkyl, heterocyclyl, aryl, or heteroaryl.

In some embodiments, the compound is a compound of Formula (II):

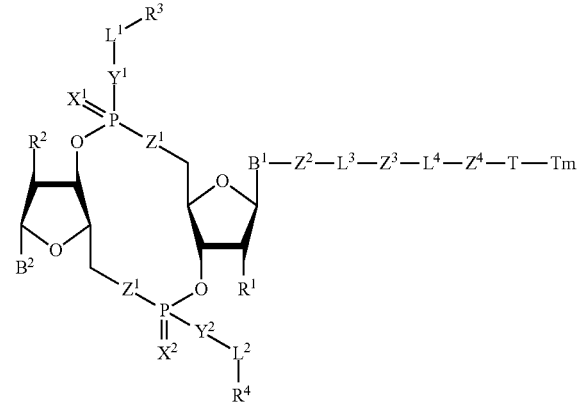

Formula (II)

or a pharmaceutically acceptable salt or stereoisomer thereof,
wherein:
Tm is a targeting moiety;
each of $B^1$ and $B^2$ is independently a purinyl nucleobase or pyrimidinyl nucleobase;
each of $X^1$ and $X^2$ is independently O or S;
each of $Y^1$ and $Y^2$ is independently O, S, or $N(R^5)$;
each of $Z^1$ is independently O or S;
$Z^2$ is —O—, —$N(R^5)$—, —S—, —C(O)—, —C(O)N($R^5$)—, —OC(O)N($R^5$)—, —N($R^5$)C(O)O—, -aryl-, -heteroaryl-, —S(O)—, —S(O)$_2$—, —S(O)N(R$^5$)—, —S(O)$_2$N(R$^5$)— or —N(R$^5$)S(O)—;

Z$^3$ is absent, hydrogen, heterocyclyl, heterocyclyl-C$_1$-C$_{20}$-alkylene-Q$^1$, —OH, —N(R$^5$)$_2$, SR$^5$, —CHO, —C(O)N(R$^5$)$_2$, —OC(O)N(R$^5$)$_2$, —N(R$^5$)C(O)OR$^5$, aryl, heteroaryl, —S(O)R$^5$, —S(O)$_2$R$^5$, —S(O)N(R$^5$)$_2$, —S(O)$_2$N(R$^5$)$_2$, —N(R$^5$)S(O)R$^5$, —OSi(C$_1$-C$_4$ alkyl)$_3$, or —C(O)C$_2$-C$_6$ alkenyl (e.g., —C$_2$-C$_4$ alkenyl);

Z$^4$ is a self-immolative group or absent;

T is a absent or spacer group;

each L$^1$ and L$^2$ is absent, —C$_1$-C$_6$— alkylene (e.g., —C$_1$-C$_3$— alkylene) or —C$_1$-C$_6$-heteroalkylene, wherein each alkylene and heteroalkyl is optionally substituted with one or more R$^6$;

L$^3$ is oligopeptide-C(O)—, oligopeptide-aryl-C$_1$-C$_6$-alkylene-, oligopeptide-aryl-C$_1$-C$_6$-alklyene-C(O)—, oligopeptide-aryl-C$_1$-C$_6$-heteroalkylene, oligopeptide-C$_1$-C$_6$-alkylene-C(O)—, oligopeptide-C$_1$-C$_6$-heteroalkylene-C(O)—, —C$_1$-C$_{40}$-alkylene (e.g., —C$_1$-C$_{20}$— alkylene), —C$_1$-C$_{40}$— heteroalkylene (e.g., —C$_1$-C$_{20}$-heteroalkyl), —C$_1$-C$_{40}$— alkenylene (e.g., —C$_2$-C$_{20}$— alkenylene), or —C$_1$-C$_{40}$-alkynylene (e.g., —C$_2$-C$_{20}$— alkynylene), wherein the oligopeptide is optionally substituted by one or more R$^{14}$;

L$^4$ is absent or a linker connecting Z$^3$ and Z$^4$;

Q$^1$ is C(O), C(S), or CH$_2$;

each of R$^1$ and R$^2$ is independently hydrogen, halo, —CN, —C$_1$-C$_{20}$ alkyl (e.g., C$_1$-C$_6$ alkyl), or —OR;

each R$^3$ and R$^4$ is independently hydrogen, —C$_1$-C$_{20}$— alkyl (e.g., —C$_1$-C$_6$ alkyl), —C$_1$-C$_{20}$ heteroalkyl (e.g., —C$_1$-C$_6$ heteroalkyl). —OC(O)OC$_1$-C$_{20}$ alkyl (e.g., —C$_1$-C$_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more R$^8$;

R$^5$ is hydrogen or —C$_1$-C$_{20}$ alkyl (e.g., —C$_1$-C$_6$ alkyl);

R$^6$ is halo, —CN, —C$_1$-C$_{20}$ alkyl (e.g., —C$_1$-C$_6$ alkyl), —OR$^7$, oxo, cycloalkyl, heterocyclyl, aryl, or heteroaryl, wherein each alkyl, cycloalkyl, heterocyclyl, aryl, and heteroaryl is optionally substituted with one or more R$^9$;

R$^7$ is hydrogen, —C$_1$-C$_{20}$ alkyl (e.g., —C$_1$-C$_6$ alkyl), cycloalkyl, heterocyclyl, aryl, or heteroaryl, wherein each alkyl, cycloalkyl, heterocyclyl, aryl, and heteroaryl is optionally substituted with one or more R$^9$;

each R$^8$ is independently —C$_1$-C$_{20}$ alkyl (e.g., —C$_1$-C$_6$ alkyl), —C$_1$-C$_{20}$ heteroalkyl, —C(O)—C$_1$-C$_{20}$ alkyl, —OC(O)—C$_1$-C$_{20}$ alkyl (e.g., —C$_1$-C$_6$ alkyl), —C(O)O—C$_1$-C$_{20}$ alkyl (e.g., —C$_1$-C$_6$ alkyl), —OC(O)O—C$_1$-C$_{20}$ alkyl (e.g., —C$_1$-C$_6$ alkyl), —C(O)N(R$^5$)—C$_1$-C$_2$ alkyl (e.g., —C$_1$-C$_6$ alkyl), —N(R$^5$)C(O)—C$_1$-C$_{20}$ alkyl (e.g., —C$_1$-C$_6$ alkyl), —OC(O)N(R$^5$)—C$_1$-C$_{20}$ alkyl (e.g., —C$_1$-C$_6$ alkyl), —O-aryl, —O— heteroaryl, —C(O)-aryl, —C(O)-heteroaryl, —OC(O)-aryl, —C(O)O-aryl, —OC(O)— heteroaryl, —C(O)O-heteroaryl, —C(O)O-aryl, —C(O)O-heteroaryl, —C(O)N(R$^5$)-aryl, —C(O)N(R$^5$)-heteroaryl, —N(R$^5$)C(O)-aryl, —N(R$^5$)$_2$C(O)-aryl, or —N(R$^5$)C(O)-heteroaryl, —S(O)$_2$N(R$^5$)-aryl, wherein each alkyl, heteroalkyl, aryl, and heteroaryl is optionally substituted by one or more R$^9$;

each R$^9$ is independently —C$_1$-C$_{20}$ alkyl, —O—C$_1$-C$_{20}$ alkyl, —C$_1$-C$_{20}$ heteroalkyl, halo, —CN, —OH, oxo, aryl, heteroaryl. —O-aryl, or —O-heteroaryl; and each R$^{16}$ is independently, —C$_1$-C$_{20}$ alkyl (e.g., —C$_1$-C$_6$ alkyl), —C$_1$-C$_{20}$ heteroalkyl (e.g., —C$_1$-C$_6$ heteroalkyl), —OC(O)OC$_1$-C$_{20}$ alkyl (e.g., —C$_1$-C$_6$ alkyl), C(O)N(R$^4$)$_2$ cycloalkyl, heterocyclyl, aryl, or heteroaryl.

In some embodiments, the compound is a compound of Formula (I'),

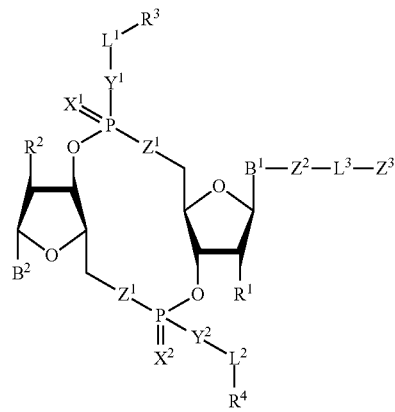

Formula (I')

or a pharmaceutically acceptable salt or stereoisomer thereof, wherein:

each of B$^1$ and B$^2$ is independently a purinyl nucleobase or pyrimidinyl nucleobase;

each of X$^1$ and X$^2$ is independently O or S;

each of Y$^1$ and Y$^2$ is independently O, S, or N(R$^5$);

each of Z$^1$ is independently O or S;

Z$^2$ is —O—, —N(R$^5$)—, —S—, —C(O)—, —C(O)N(R$^5$)—, —OC(O)N(R$^5$)—, —N(R$^5$)C(O)O—, -aryl-, -heteroaryl-, —S(O)—, —S(O)$_2$—, —S(O)N(R$^5$)—, —S(O)$_2$N(R$^5$)— or —N(R$^5$)S(O)—;

Z$^3$ is hydrogen, —OH, —N(R$^5$)$_2$, SR$^5$, —CHO, —C(O)N(R$^5$)$_2$, —OC(O)N(R$^5$)$_2$, —N(R$^5$)C(O)OR$^5$, aryl, heteroaryl, —S(O)R$^5$, —S(O)$_2$R$^5$, —S(O)N(R$^5$)$_2$, —S(O)$_2$N(R$^5$)$_2$, —N(R$^5$)S(O)R$^5$, —OSi(C$_1$-C$_4$ alkyl)$_3$, or —C(O)C$_2$-C$_6$ alkenyl (e.g., —C$_2$-C$_4$ alkenyl); L is —C$_1$-C$_6$— alkylene (e.g., C$_1$-C$_3$ alkylene) or —C$_1$-C$_6$— heteroalkylene (e.g., —C$_1$-C$_3$ heteroalkylene);

L$^2$ is absent, —C$_1$-C$_6$— alkylene (e.g., —C$_1$-C$_3$— alkylene) or —C$_1$-C$_6$— heteroalkylene, wherein each alkylene and hetero alkylene is optionally substituted with one or more R$^6$;

L$^3$ is —C$_1$-C$_{40}$— alkylene (e.g., —C$_1$-C$_{20}$— alkylene), —C$_1$-C$_{40}$— heteroalkylene (e.g., —C$_1$-C$_{20}$— heteroalkyl), —C$_1$-C$_{40}$— alkenylene (e.g., —C$_2$-C$_{20}$— alkenylene), or —C$_1$-C$_{40}$-alkynylene (e.g., —C$_2$-C$_{20}$— alkynylene);

each of R$^1$ and R$^2$ is independently hydrogen, halo, —CN, —C$_1$-C$_{20}$ alkyl (e.g., —C$_1$-C$_6$ alkyl), or OR$^7$;

each R$^3$ and R$^4$ is independently hydrogen, —C$_1$-C$_{20}$— alkyl (e.g., —C$_1$-C$_6$ alkyl), —C$_1$-C$_{20}$ heteroalkyl (e.g., —C$_1$-C$_6$ heteroalkyl), —OC(O)OC$_1$-C$_{20}$ alkyl (e.g., —C$_1$-C$_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more R$^8$;

R$^5$ is hydrogen or —C$_1$-C$_{20}$ alkyl (e.g., —C$_1$-C$_6$ alkyl);

R$^6$ is halo, —CN, —C$_1$-C$_{20}$ alkyl (e.g., —C$_1$-C$_6$ alkyl), —OR$^7$, oxo, cycloalkyl, heterocyclyl, aryl, or heteroaryl, wherein each alkyl, cycloalkyl, heterocyclyl, aryl, and heteroaryl is optionally substituted with one or more R$^9$;

R$^7$ is hydrogen, —C$_1$-C$_{20}$ alkyl (e.g., C$_1$-C$_6$ alkyl), cycloalkyl, heterocyclyl, aryl, or heteroaryl, wherein each alkyl, cycloalkyl, heterocyclyl, aryl, and heteroaryl is optionally substituted with one or more $R^9$;

each $R^8$ is independently —$C_1$-$C_{20}$ alkyl (e.g., —$C_1$-$C_6$ alkyl), —$C_1$-$C_{20}$ heteroalkyl, —C(O), —$C_1$-$C_{20}$ alkyl, —OC(O)—$C_1$-$C_{20}$ alkyl (e.g., —$C_1$-$C_6$ alkyl), —C(O)O—$C_1$-$C_{20}$ alkyl (e.g., —$C_1$-$C_6$ alkyl), —OC(O)O—$C_1$-$C_{20}$ alkyl (e.g., —$C_1$-$C_6$ alkyl), —C(O)N($R^5$)—$C_1$-$C_{20}$ alkyl (e.g., —$C_1$-$C_6$ alkyl), —N($R^5$)C(O)—$C_1$-$C_{20}$ alkyl (e.g., —$C_1$-$C_6$ alkyl), —OC(O)N($R^5$)—$C_1$-$C_{20}$ alkyl (e.g., —$C_1$-$C_6$ alkyl), —O-aryl, —O-heteroaryl, —C(O)-aryl, —C(O)-heteroaryl, —OC(O)-aryl, —C(O)O-aryl, —OC(O)-heteroaryl, —C(O)O-heteroaryl, —C(O)O-aryl, —C(O)O-heteroaryl, —C(O)N($R^5$)-aryl, —C(O)N($R^5$)-heteroaryl, —N($R^5$)C(O)-aryl, —N($R^5$)$_2$C(O)-aryl, or —N($R^5$)C(O)-heteroaryl, —S(O)$_2$N($R^5$)-aryl, wherein each alkyl, heteroalkyl, aryl, and heteroaryl is optionally substituted by one or more $R^9$; and each $R^9$ is independently —$C_1$-$C_{20}$ alkyl, —O—$C_1$-$C_{20}$ alkyl, —$C_1$-$C_{20}$ heteroalkyl, halo, —CN, —OH, oxo, aryl, heteroaryl, —O-aryl, or —O-heteroaryl.

In some embodiments, the compound is a compound of formula (I-e'), (I-f), (I-g'), (I-h'), (I-i') or (I-j'):

Formula (I-e')

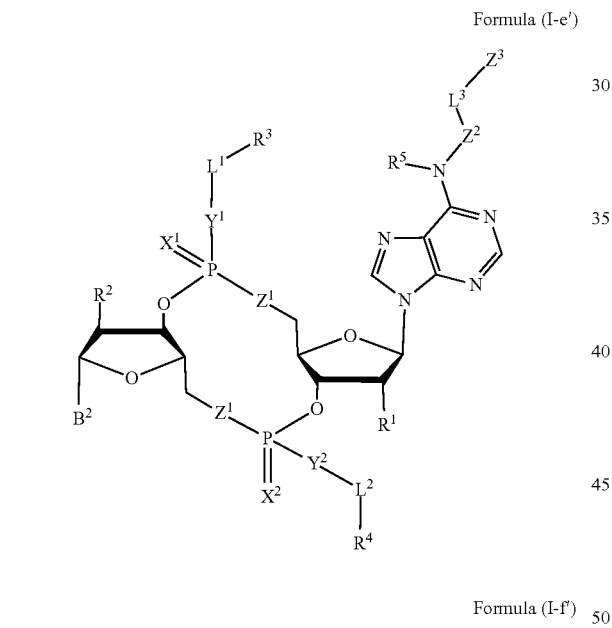

Formula (I-f')

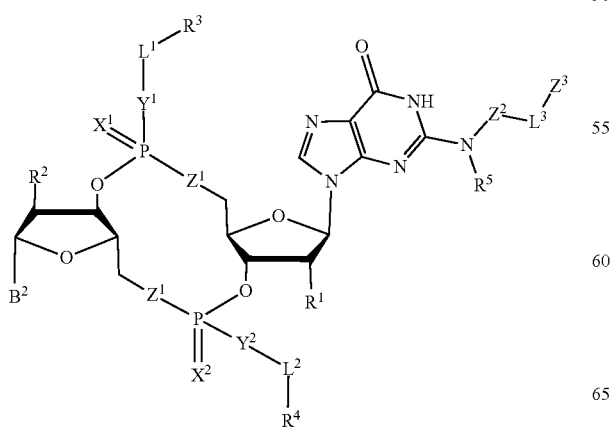

Formula (I-g')

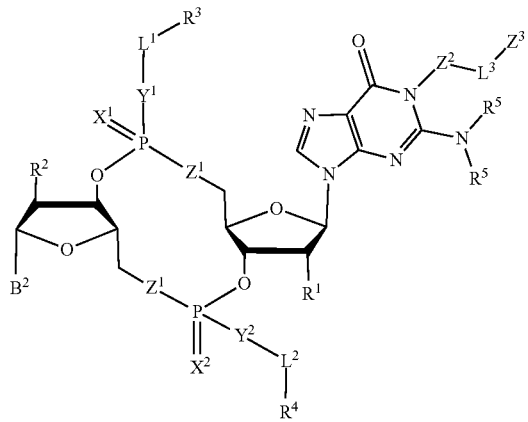

Formula (I-h')

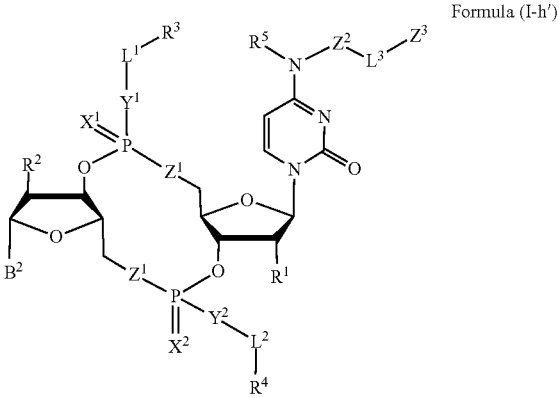

Formula (I-i')

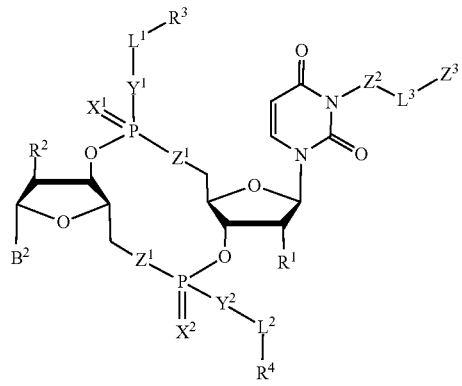

Formula (I-j')

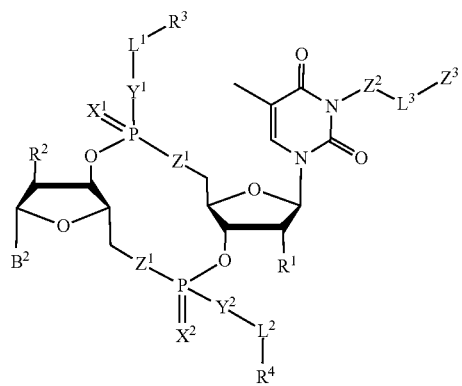

In some embodiments, the compound is a compound of Formula (II'),

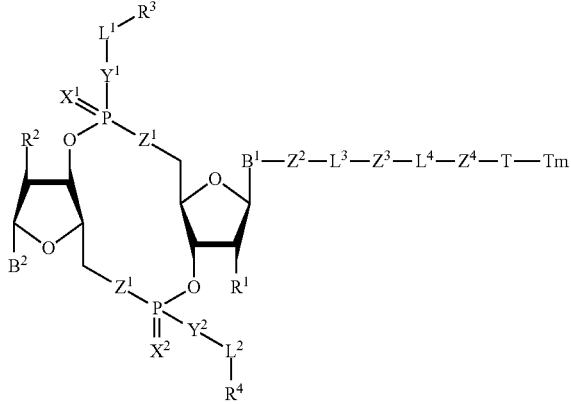

Formula (II')

or a pharmaceutically acceptable salt or stereoisomer thereof,
wherein:
Tm is a targeting moiety:
each of $B^1$ and $B^2$ is independently a purinyl nucleobase or pyrimidinyl nucleobase;
each of $X^1$ and $X^2$ is independently O or S;
each of $Y^1$ and $Y^2$ is independently O, S, or $N(R^5)$;
each of $Z^1$ is independently O or S;
$Z^2$ is —O—, —$N(R^5)$—, —S—, —C(O)—, —C(O)N($R^5$)—, —OC(O)N($R^5$)—, —N($R^5$)C(O)O—, -aryl-, -heteroaryl-, —S(O)—, —S(O)$_2$—, —S(O)N($R^5$)—, —S(O)$_2$N($R^5$)— or —N($R^5$)S(O)—;
$Z^3$ is absent, —O—, —N($R^5$)—, —S—, —C(O)—, —C(O)N($R^5$)—, —OC(O)N($R^5$)—, —N($R^5$)C(O)O—, -aryl-, -heteroaryl-, —S(O)—, —S(O)$_2$—, —S(O)N($R^5$)—, —S(O)$_2$N($R^5$)— or —N($R^5$)S(O)—;
$Z^4$ is a self-immolative group or absent;
T is a spacer group;
each $L^1$ and $L^2$ is absent, —$C_1$-$C_6$— alkylene (e.g., —$C_1$-$C_3$— alkylene) or —$C_1$-$C_6$-heteroalkylene, wherein each alkylene and heteroalkyl is optionally substituted with one or more $R^6$;
$L^3$ is —$C_1$-$C_{20}$— alkylene (e.g., $C_1$-$C_6$ alkylene), —$C_1$-$C_{20}$— hetero alkylene (e.g., —$C_1$-$C_6$-heteroalkylene), —$C_1$-$C_{20}$— alkenylene (e.g., —$C_2$-$C_6$— alkenylene), —$C_1$-$C_{20}$-alkynylene (e.g., —$C_2$-$C_6$— alkynylene);
$L^4$ is a linker connecting $Z^3$ and $Z^4$;
each of $R^1$ and $R^2$ is independently hydrogen, halo, —CN, —$C_1$-$C_{20}$ alkyl (e.g., $C_1$-$C_6$ alkyl), or —OR;
each $R^3$ and $R^4$ is independently hydrogen, —$C_1$-$C_{20}$— alkyl (e.g., —$C_1$-$C_6$ alkyl), —$C_1$-$C_{20}$ heteroalkyl (e.g., —$C_1$-$C_6$ heteroalkyl), —OC(O)O$C_1$-$C_{20}$ alkyl (e.g., —$C_1$-$C_6$ alkyl), cycloalkyl, heterocyclyl, aryl, or heteroaryl, wherein each alkyl, heteroalkyl, cycloalkyl, heterocyclyl, aryl, and heteroaryl is optionally substituted with one or more $R^8$;
$R^5$ is hydrogen or —$C_1$-$C_{20}$ alkyl (e.g., —$C_1$-$C_6$ alkyl);
$R^6$ is halo, —CN, —$C_1$-$C_{20}$ alkyl (e.g., —$C_1$-$C_6$ alkyl), —$OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$;
$R^7$ is hydrogen, —$C_1$-$C_{20}$ alkyl (e.g., —$C_1$-$C_6$ alkyl), cycloalkyl, heterocyclyl, aryl, or heteroaryl, wherein each alkyl, cycloalkyl, heterocyclyl, aryl, and heteroaryl is optionally substituted with one or more $R^9$;

each $R^8$ is independently —$C_1$-$C_{20}$ alkyl (e.g., —$C_1$-$C_6$ alkyl), —$C_1$-$C_{20}$ heteroalkyl, —C(O)—$C_1$-$C_{20}$ alkyl, —OC(O)—$C_1$-$C_{20}$ alkyl (e.g., —$C_1$-$C_6$ alkyl), —C(O)O—$C_1$-$C_{20}$ alkyl (e.g., —$C_1$-$C_6$ alkyl), —OC(O)O—$C_1$-$C_{20}$ alkyl (e.g., —$C_1$-$C_6$ alkyl), —C(O)N($R^5$)—$C_1$-$C_{20}$ alkyl (e.g., —$C_1$-$C_6$ alkyl), —N($R^5$)C(O)—$C_1$-$C_{20}$ alkyl (e.g., —$C_1$-$C_6$ alkyl), —OC(O)N($R^5$)—$C_1$-$C_{20}$ alkyl (e.g., —$C_1$-$C_6$ alkyl), —O-aryl, —O— heteroaryl, —C(O)-aryl, —C(O)-heteroaryl, —OC(O)-aryl, —C(O)O-aryl, —OC(O)— heteroaryl, —C(O)O-heteroaryl, —C(O)O-aryl, —C(O)O-heteroaryl, —C(O)N($R^5$)-aryl, —C(O)N($R^5$)-heteroaryl, —N($R^5$)C(O)-aryl, —N($R^5$)$_2$C(O)-aryl, or —N($R^5$)C(O)-heteroaryl, —S(O)$_2$N($R^5$)-aryl, wherein each alkyl, heteroalkyl, aryl, and heteroaryl is optionally substituted by one or more $R^9$; and
each $R^9$ is independently —$C_1$-$C_{20}$ alkyl, —O—$C_1$-$C_{20}$ alkyl, —$C_1$-$C_{20}$ heteroalkyl, halo, —CN, —OH, oxo, aryl, heteroaryl, —O-aryl, or —O-heteroaryl.

In some embodiments, wherein the compound is a compound of formula (II-e'), (II-f'), (II-g'), (II-h'), (II-i') or (II-j'):

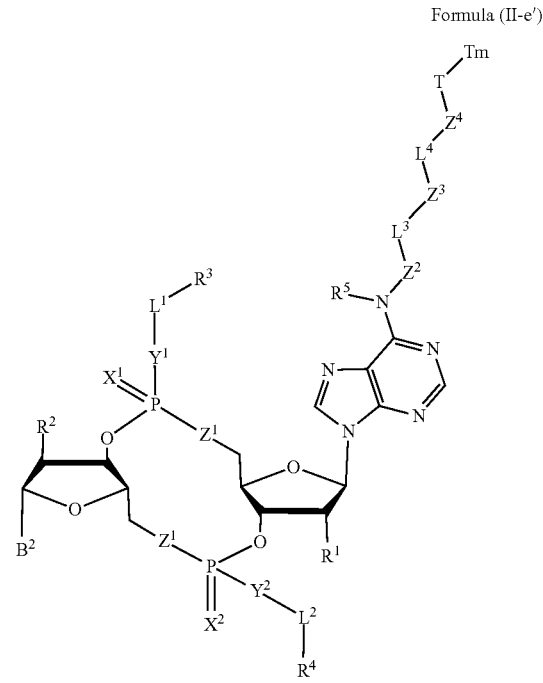

Formula (II-e')

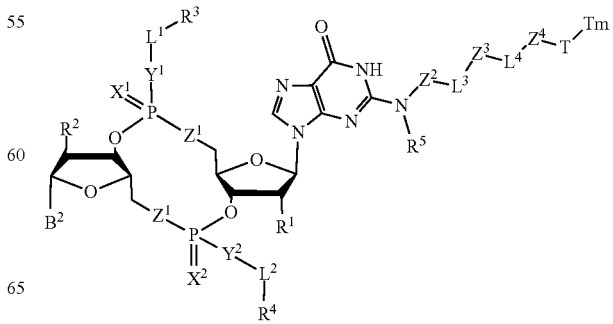

Formula (II-f')

-continued

Formula (II-g′)

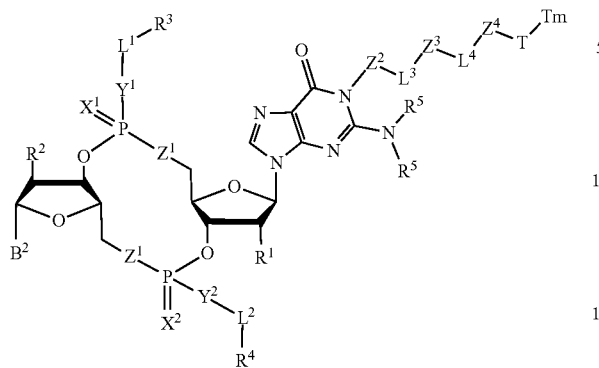

Formula (II-h′)

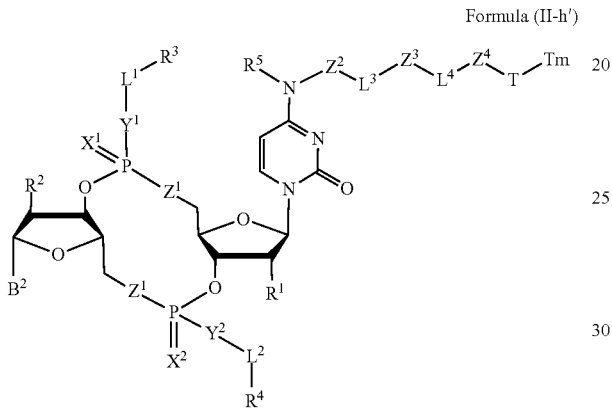

Formula (II-i′)

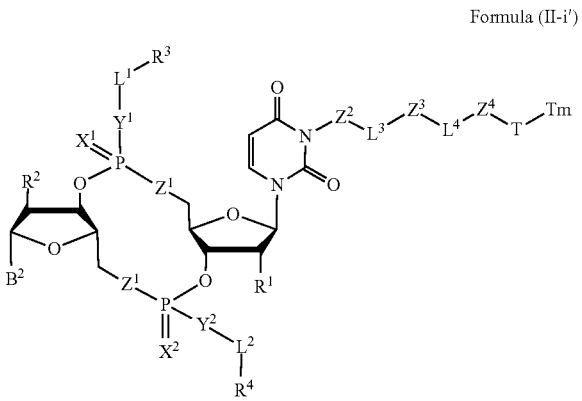

Formula (II-j′)

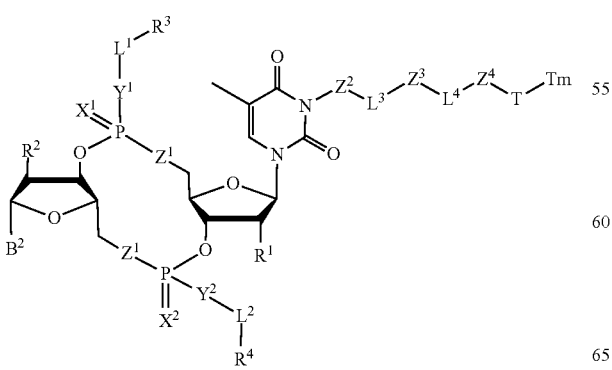

In some embodiments, the compound is a compound of Formula (II-k):

Formula (II-k)

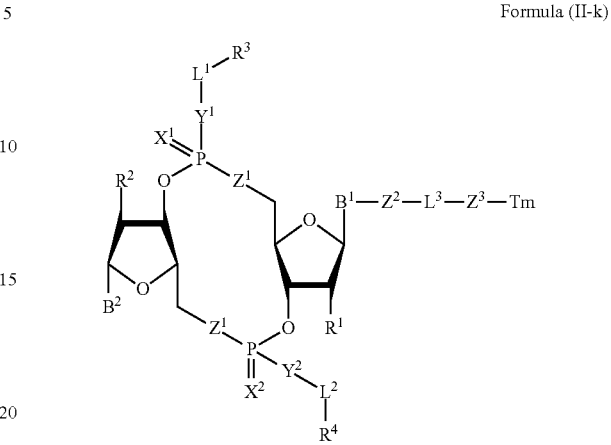

or a pharmaceutically acceptable salt or stereoisomer thereof.

In some embodiments, each of $B^1$ or $B^2$ is selected from a naturally occurring nucleobase or a modified nucleobase. In some embodiments, each of $B^1$ or $B^2$ is selected from adenosinyl, guanosinyl, cytosinyl, thyminyl, uracilyl, 5′-methylcytosinyl, 5′-fluorouracilyl, 5′-propynyluracilyl, and 7-deazaadenosinyl. In some embodiments, each of $B^1$ or $B^2$ is selected from:

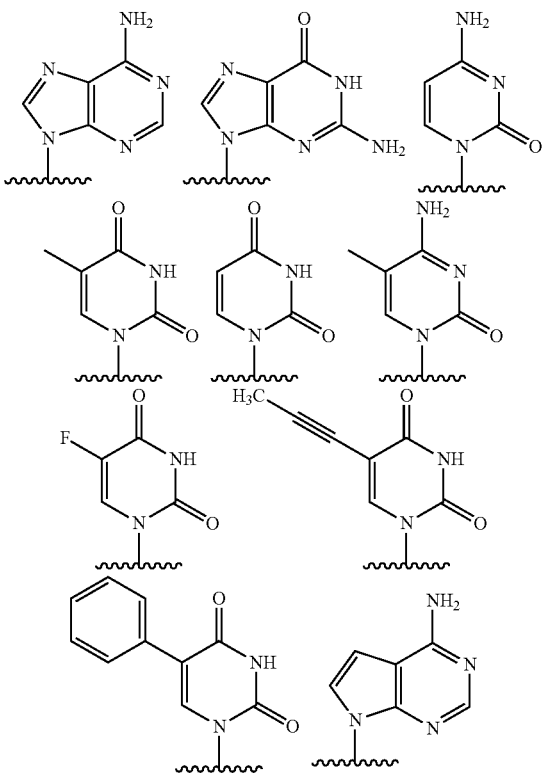

wherein " ~~~~ " indicates the linkage of the nucleobase to the ribose ring.

In some embodiments, one of $B^1$ or $B^2$ is selected from a naturally occurring nucleobase and the other of $B^1$ or $B^2$ is a modified nucleobase. In some embodiments, one of $B^1$ or $B^2$ is adenosinyl, guanosinyl, thyminyl, cytosinyl, or uracilyl, and the other of $B^1$ or $B^2$ is 5'-methylcytosinyl, 5'-fluorouracilyl, 5'-propynyluracilyl, or 7-deazaadenosinyl.

In some embodiments, one of $B^1$ or $B^2$ is selected from a naturally occurring nucleobase and the other of $B^1$ or $B^2$ is a modified nucleobase. In some embodiments, one of $B^1$ or $B^2$ is adenosinyl, guanosinyl, thyminyl, cytosinyl, or uracilyl, and the other of $B^1$ or $B^2$ is 5'-methylcytosinyl, 5'-fluorouracilyl, 5'-propynyluracilyl, or 7-deazaadenosinyl.

In some embodiments, $B^1$ is adenosinyl or guanosinyl. In some embodiments, $B^2$ is cytosinyl, thyminyl, or uracilyl. In some embodiments, $B^1$ is adenosinyl or guanosinyl and $B^2$ is cytosinyl, thyminyl, or uracilyl. In some embodiments, each of $B^1$ and $B^2$ is independently uracilyl. In some embodiments, each of $B^1$ and $B^2$ is independently adenosinyl.

In some embodiments, each of $R^1$ and $R^2$ is independently hydrogen, halo, or $OR^7$. In some embodiments, each of $R^1$ and $R^2$ is independently halo (e.g., fluoro). In some embodiments, each of $R^1$ and $R^2$ is not hydrogen or $OR^7$.

In some embodiments, $X^1$ is O. In some embodiments, $X^2$ is O. In some embodiments, each of $X^1$ and $X^2$ is independently O.

In some embodiments, $Y^1$ is O or S. In some embodiments, $Y^2$ is O or S. In some embodiments, each of $Y^1$ and $Y^2$ is independently O or S. In some embodiments, one of $Y^1$ or $Y^2$ is O and the other of $Y^1$ or $Y^2$ is S. In some embodiments, each of $Y^1$ or $Y^2$ is independently S. In some embodiments, each of $Y^1$ or $Y^2$ is independently O.

In some embodiments, $L^1$ is $C_1$-$C_6$ alkyl (e.g., $CH_2$). In some embodiments, $L^2$ is $C_1$-$C_6$ alkyl (e.g., $CH_2$). In some embodiments, each of $L^1$ and $L^2$ is independently $C_1$-$C_6$ alkyl (e.g., $CH_2$).

In some embodiments, $R^3$ is hydrogen, aryl, or heteroaryl, wherein aryl and heteroaryl is optionally substituted with 1-5 $R^8$. In some embodiments, $R^3$ is aryl or heteroaryl, each of which is optionally substituted with 1-5 $R^8$. In some embodiments, $R^3$ is phenyl substituted with 1 $R^8$.

In some embodiments, $R^4$ is independently hydrogen, aryl, or heteroaryl, wherein aryl and heteroaryl is optionally substituted with 1-5 $R^8$. In some embodiments, $R^4$ is aryl or heteroaryl, each of which is optionally substituted with 1-5 $R^8$. In some embodiments, $R^4$ is phenyl substituted with 1 $R^8$.

In some embodiments, each of $R^3$ and $R^4$ is independently hydrogen, aryl, or heteroaryl, wherein aryl and heteroaryl is optionally substituted with 1-5 $R^8$. In some embodiments, $R^3$ is aryl or heteroaryl, each of which is optionally substituted with 1-5 $R^8$, and $R^4$ is hydrogen. In some embodiments, $R^3$ is phenyl substituted with 1 $R^8$ and $R^4$ is hydrogen. In some embodiments, each of $R^3$ and $R^4$ is independently phenyl substituted with 1 $R^8$.

In some embodiments, each of $Y^1$ and $Y^2$ is O and each of $R^3$ and $R^4$ is independently hydrogen. In some embodiments, $Y^2$ is O and $R^4$ is hydrogen. In some embodiments, each of $Y^1$ and $Y^2$ is independently S and each of $R^3$ and $R^4$ is independently substituted with 1 $R^8$. In some embodiments, $Y^1$ is S and $R^3$ is substituted with 1 $R^8$.

In some embodiments, each $R^8$ is independently $C_1$-$C_{20}$ alkyl (e.g., $C_1$-$C_6$ alkyl), $C_1$-$C_{20}$ heteroalkyl, C(O)—$C_1$-$C_{20}$ alkyl, OC(O)—$C_1$-$C_{20}$ alkyl, OC(O)O—$C_1$-$C_{20}$ alkyl, OC(O)N($R^5$)—$C_1$-$C_{20}$ alkyl, O-aryl, C(O)-aryl, OC(O)-aryl, or C(O)N($R^5$)-aryl, wherein each alkyl, heteroalkyl, aryl, and heteroaryl is optionally substituted by one or more $R^9$.

In some embodiments, $R^8$ is OC(O)-aryl optionally substituted by 1-5 $R^9$ (e.g., 1 $R^9$). In some embodiments, $R^9$ is O—$C_1$-$C_{12}$ alkyl (e.g., O—$CH_2(CH_2)_8CH_3$). In some embodiments, $R^9$ is O—$C_1$-$C_{10}$ alkyl (e.g., O—$CH_2(CH_2)_6CH_3$). In some embodiments, $R^9$ is O—$C_1$-$C_8$ alkyl (e.g., O—$CH_2(CH_2)_6CH_3$). In some embodiments, $R^9$ is O—$C_1$-$C_6$ alkyl (e.g., O—$CH_2(CH_2)_4CH_3$).

In some embodiments, each of $L^1$ and $L^2$ is independently $C_1$-$C_6$ alkylene (e.g., $C_1$ alkylene).

In some embodiments, $L^3$ is —$C_1$-$C_{20}$— alkylene (e.g., —$C_1$-$C_{18}$— alkylene). In some embodiments, $L^3$ is —$C_1$-$C_{20}$— heteroalkylene (e.g., —$C_1$-$C_{18}$— heteroalkylene). In some embodiments, $L^3$ is an oligiopeptide-C(O)—, oligiopeptide-aryl-$C_1$-$C_6$-alkylene-, oligiopeptide-aryl-$C_1$-$C_6$-heteroalkylene, oligiopeptide-aryl-$C_1$-$C_6$-alklyene-C(O)—, oligiopeptide-$C_1$-$C_6$-alkylene-C(O)—, oligiopeptide-$C_1$-$C_6$-heteroalkylene-C(O)—. In some embodiments, the aryl is phenyl. In some embodiments, the oligiopeptide is a dipeptide. In some embodiments, the oligopeptide comprises 3 amino acid residues, 4 amino acid residues, 5 amino acid residues, 6 amino acid residues, 7 amino acid residues, 8 amino acid residues, 9 amino acid residues, or 10 amino acid residues. In some embodiments, the oligopeptide comprises 8 amino acid residues. In some embodiments, the oligopeptide comprises an amino acid selected from Tyr, Ser, Thr, Arg, Leu, Ile, Gly, Val, and Ala. In some embodiments, he oligopeptide comprises an amino acid selected from Phe, Tyr, Arg, Gly, Ser, and Leu. In some embodiments, $L^3$ is

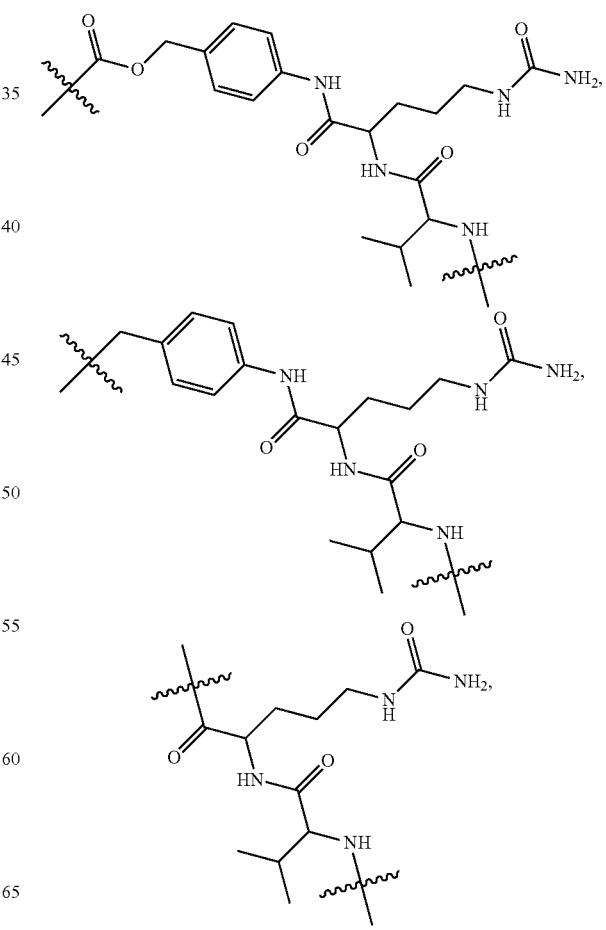

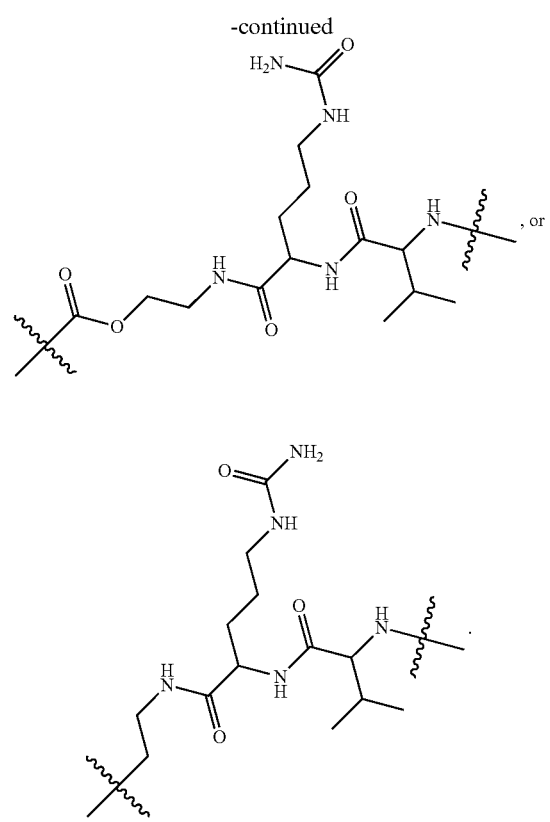
In other embodiments, $L^3$ is
In yet other embodiments, $L^3$ is selected from the group consisting of
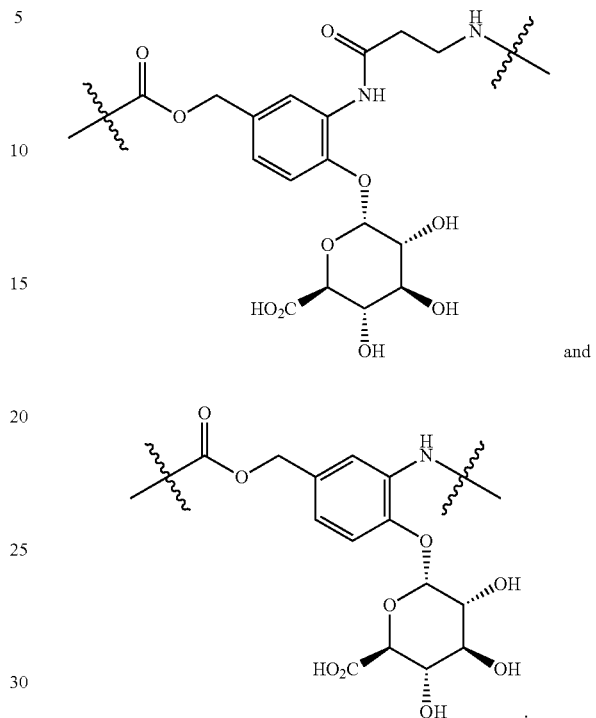
and
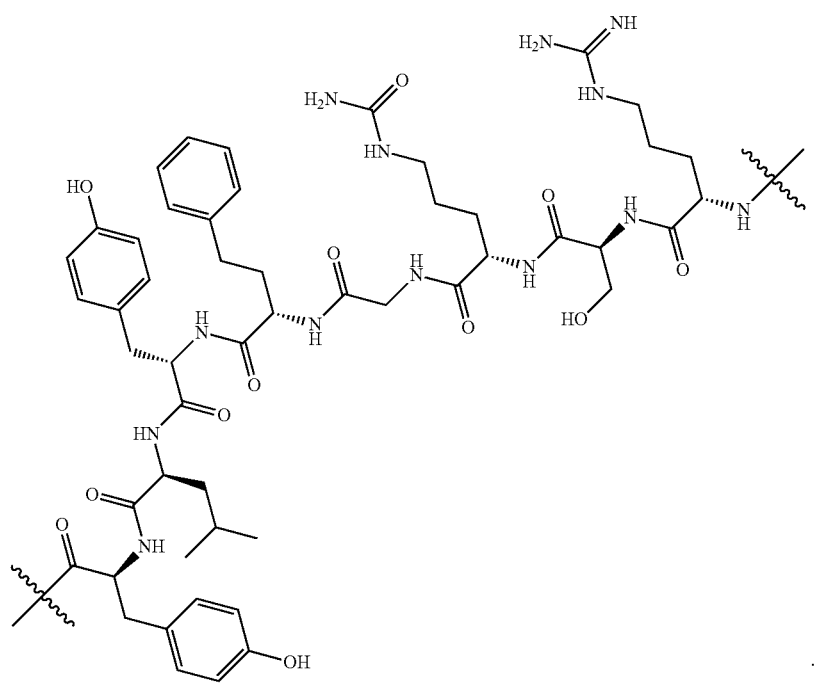 [SMILES: *N[C@@H](CCCNC(=N)N)C(=O)N[C@@H](CO)C(=O)N[C@@H](CCCNC(N)=O)C(=O)NCC(=O)N[C@@H](CCc1ccccc1)C(=O)N[C@@H](Cc1ccc(O)cc1)C(=O)N[C@@H](CC(C)C)C(=O)N[C@@H](Cc1ccc(O)cc1)C(*)=O]
.

In some embodiments, $L^3$ is

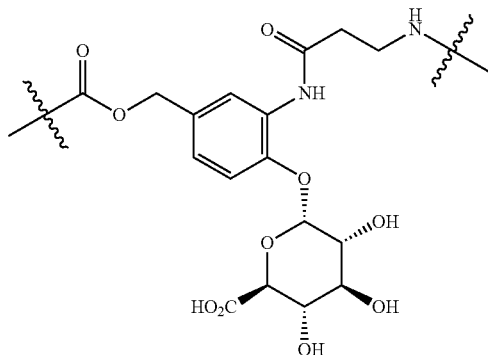

In some embodiments, the oligiopeptide is substituted by one or more instances of $R^{16}$. In some embodiments, $R^{16}$ is $C(O)NH_2$.

In some embodiments, $L^4$ is —$C_1$-$C_{40}$— alkylene (e.g., —$C_1$-$C_{20}$— alkylene), —$C_1$-$C_{40}$— heteroalkylene (e.g., —$C_1$-$C_{20}$— heteroalkyl), —$C_1$-$C_{40}$— alkenylene (e.g., —$C_2$-$C_{20}$-alkenylene), or —$C_1$-$C_{40}$— alkynylene (e.g., —$C_2$-$C_{20}$— alkynylene). In some embodiments, $L^4$ is an oligopeptide comprising of 1-40 amino acid residues. In some embodiments, $L^4$ further comprises one

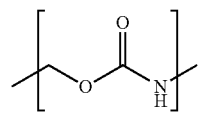

sub-units. In some embodiments, $L^4$ further comprises one

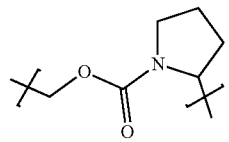

sub-unit. In some embodiments, $L^4$ further comprises one

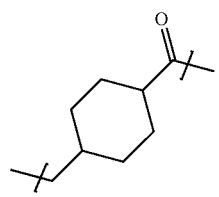

sub-unit. In some embodiments, $L^4$ further comprises one

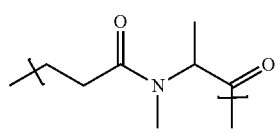

sub-unit. In some embodiments, $L^4$ is absent.

In some embodiments, each $Z^1$ is oxygen.

In some embodiments, $Z^3$ is —O—, —N($R^5$)— or -heteroaryl-. In some embodiments, $Z^3$ is

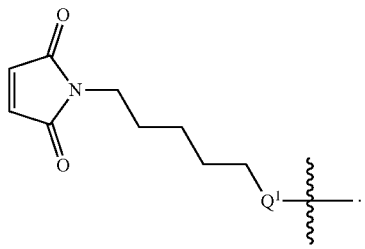

In some embodiments, $Z^3$ is

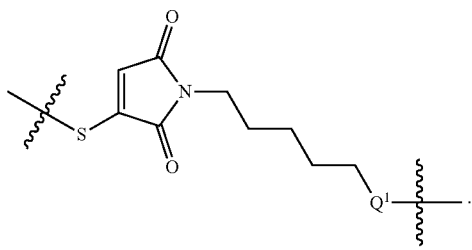

In some embodiments, $Q^1$ is C(O).

In some embodiments, $Z^4$ is

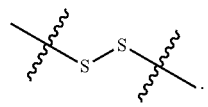 [SMILES: *SS*]

In some embodiments, $Z^4$ is

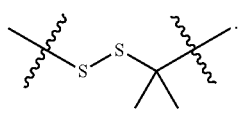 [SMILES: *SSC(*)(C)C]

In some embodiments, $Z^4$ is

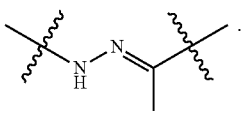 [SMILES: *N/N=C(/*)C]

In some embodiments, $Z^4$ is

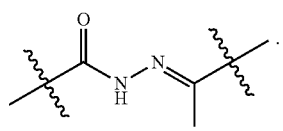 [SMILES: *C(=O)N/N=C(/*)C]

In some embodiments, $Z^4$ is

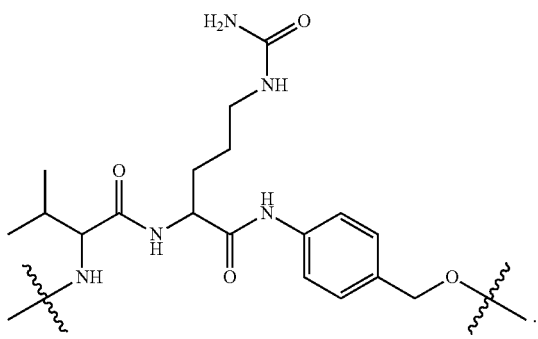 [SMILES: *NC(C(=O)NC(CCCNC(N)=O)C(=O)Nc1ccc(CO*)cc1)C(C)C]

In some embodiments, $Z^4$ is

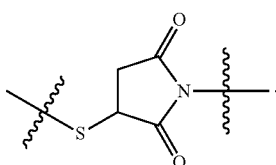

In some embodiments, $Z^4$ is

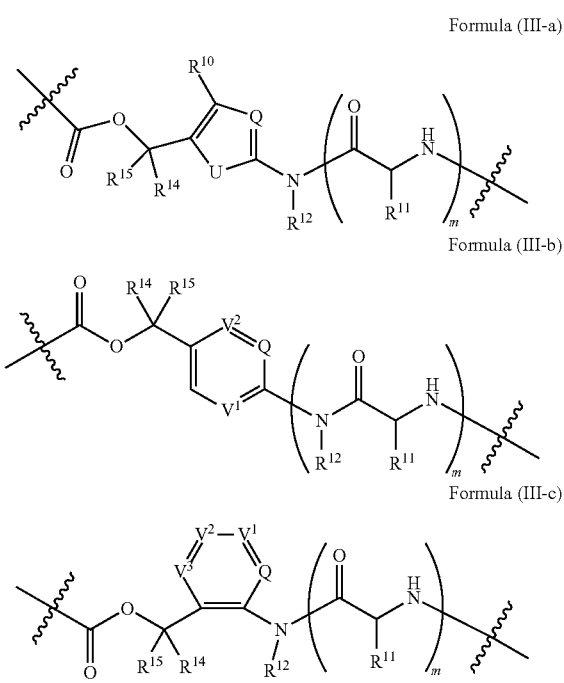

wherein:

U is O, S or $NR^{13}$;

Q is $CR^{13}$ or N;

each $V^1$, $V^2$ and $V^3$ are independently $CR^{17}$ or N provided that for formula (III-b) and (III-c) at least one of Q, $V^1$ and $V^2$ is N;

$R^{11}$ is the side chain of an amino acid and is optionally protected with a protecting group;

Each $R^{10}$, $R^{14}$, and $R^{15}$ are independently selected from hydrogen, halo, OH, —$N(R^{12})_2$, —$N(R^{12})_3$+, $C_1$-$C_8$ heteroalkyl, carboxylate, sulfate, sulfamate, sulfonate, —$SO_2R^5$, —$S(O)R^{12}$, —$SR^{12}$, —$SO_2N(R^{12})_2$, —$C(O)R^5$, —$CO_2R^{12}$, —$C(O)N(R^{12})_2$, —CN, —$N_3$, —$NO_2$, $C_1$-$C_8$ heteroalkyl, polyethyleneoxy, phosphonate, phosphate, $C_1$-$C_8$ alkyl, $C_2$-$C_8$, $C_2$-$C_8$ alkenyl, $C_2$-$C_8$ alkynl, $C_2$-$C_8$, aryl, and heterocycle; or when taken together, $R^{14}$ and $R^{15}$ form a carbonyl (=O), or spiro-carbocyclic ring comprising of 3 to 7 carbon atoms; and $R^{12}$ and $R^{13}$ are independently selected from hydrogen, $C_1$-$C_8$ alkyl, $C_2$-$C_8$ alkenyl, $C_2$-$C_8$ alkynyl, aryl, heterocycle, wherein each alkyl, alkenyl, alkynyl, aryl, and heterocycle are independently substituted with one or more substituents selected from halo, OH, —$N(R^{12})_2$, —$N(R^{12})^3$+, heteroalkyl, carboxylate, sulfate, sulfamate, sulfonate, 4-dialkylaminopyridinium, alkyl, —$SO_2R^{12}$, —$S(O)R^{12}$, —$SR^{12}$, —$SO_2N(R^{12})_2$, $C(O)R^{12}$, $CO_2R^{12}$, $C(O)N(R^{12})_2$, —CN, —$N_3$, —$NO_2$, $C_3$-$C_{12}$ carbocycle, aryl, heterocycle, polyethyleneoxy, phosphonate, and phosphate.

In some embodiments, Q is N; $V^1$ is CH, and $V^2$ is CH. In some embodiments, Q is CH; $V^1$ is CH and $V^2$ is N. In some embodiments, Q is N; $V^1$ is CH, and $V^2$ is N. In some embodiments, Q is N; and $V^1$ is N and $V^2$ is N. In some embodiments, Q is N; $V^1$ is N and $V^2$ is CH. In some embodiments, Q is N; and $V^1$, $V^2$ and $V^3$ are each CH. In some embodiments, Q is CH; and $V^1$, $V^2$ and $V^3$ are each CH.

In some embodiments, $Z^4$ is absent.

In some embodiments, T is —$C_1$-$C_{20}$— alkylene (e.g., —$C_1$-$C_6$— alkylene), —$C_1$-$C_{20}$-heteroalkylene (e.g., —$C_1$-$C_6$— heteroalkylene), —$C_1$-$C_{20}$— alkenylene (e.g., —$C_2$-$C_6$-alkenylene), —$C_1$-$C_{20}$— alkynylene (e.g., —$C_2$-$C_6$— alkynyl), -aryl- or -heteroaryl-. In some embodiments, T is absent.

In some embodiments, Tm is an antibody, a hormone, a hormone derivative, folic acid, a folic acid derivative, a biotin, a small molecule, an oligopeptide, a sigma-2-ligand, or a sugar.

In some embodiments, the antibody is selected from intact polyclonal antibodies, intact monoclonal antibodies, antibody fragments, single chain Fv (scFv) mutants, multispecific antibodies, bispecific antibodies, chimeric antibodies, humanized antibodies, human antibodies, fusion proteins including an antigen determination portion of an antibody, and other modified immunoglobulin molecules including an antigen recognition site.

In some embodiments, the antibody is selected from muromonab-CD3, abciximab, rituximab, daclizumab, palivizumab, infliximab, trastuzumab, etanercept, basiliximab, gemtuzumab ozogamicin, alemtuzumab, ibritumomab tiuxetan, adalimumab, alefacept, omalizumab, efalizumab, tositumomab-$I^{131}$, cetuximab, bevacizumab, natalizumab, ranibizumab, panitumumab, eculizumab, rilonacept, certolizumab pegol, romiplostim, belimumab, anti-CD20, tocilizumab, atlizumab, mepolizumab, pertuzumab, tremelimumab, ticilimumab, inotuzumab ozogamicin, aflibercept, catumaxomab, pregovomab, motavizumab, efumgumab, Aurograb®, raxibacumab, and veltuzumab. In some embodiments, the antibody is selected from an anti-CD22 antibody or an anti-CD79b antibody.

In some embodiments, the steroid is an estrogen, an androgen, a cholesterol or any derivative thereof. In some embodiments, the hormone is selected from estrogen, testosterone, dihydrotestosterone, ethisterone, and cholesterol.

In some embodiments, Tm is folic acid or any derivative thereof. In some embodiments, Tm is biotin. In some embodiments, Tm is a substituted benzodiazepine. In some embodiments, Tm is a glutamate-urea-lysine. In some embodiments, Tm is asparaginyl-glycinyl-aginine oligopeptide.

In some embodiments, Tm is an integrin ligand. In some embodiments, the integrin ligand is an RGD peptide. In some embodiments, the RGD peptide is an Arg-Gly-Asp oligopeptide.

In some embodiments, Tm is a sigma-2-ligand.

In some embodiments, Tm is a sugar. In some embodiments, the sugar is galactose. In some embodiments, the sugar is N-acetyl-galactosamine.

In some embodiments, the compound is selected from Table 1:

TABLE 1
| Number | Compound |
|---|---|
| 1 (Tm is a targetting moiety) | 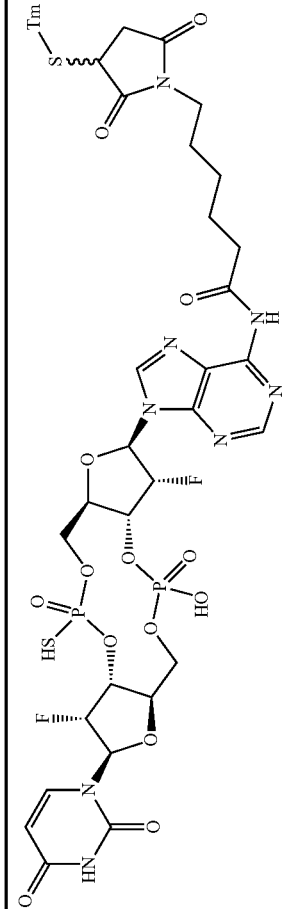 |
| 2 (Tm is a targetting moiety) | 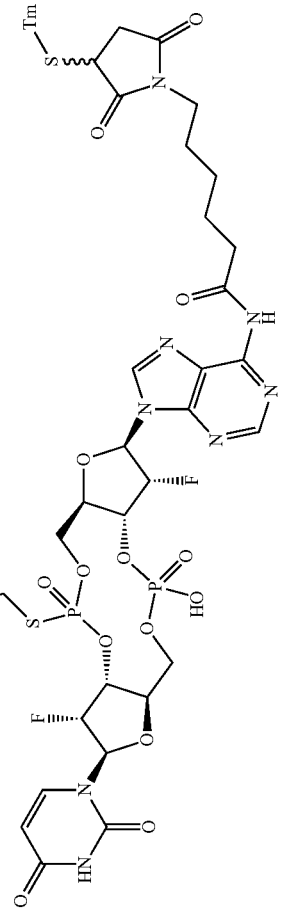 |

TABLE 1-continued
| Number | Compound |
|---|---|
| 3 (Tm is a targetting moiety) | 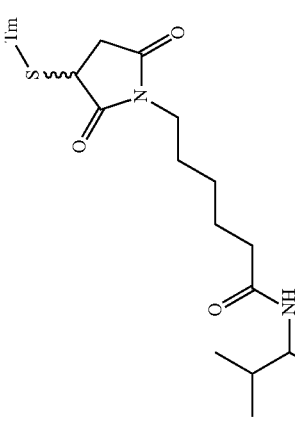 |

TABLE 1-continued
| Number | Compound |
|---|---|
| 4 (Tm is a targetting moiety) | 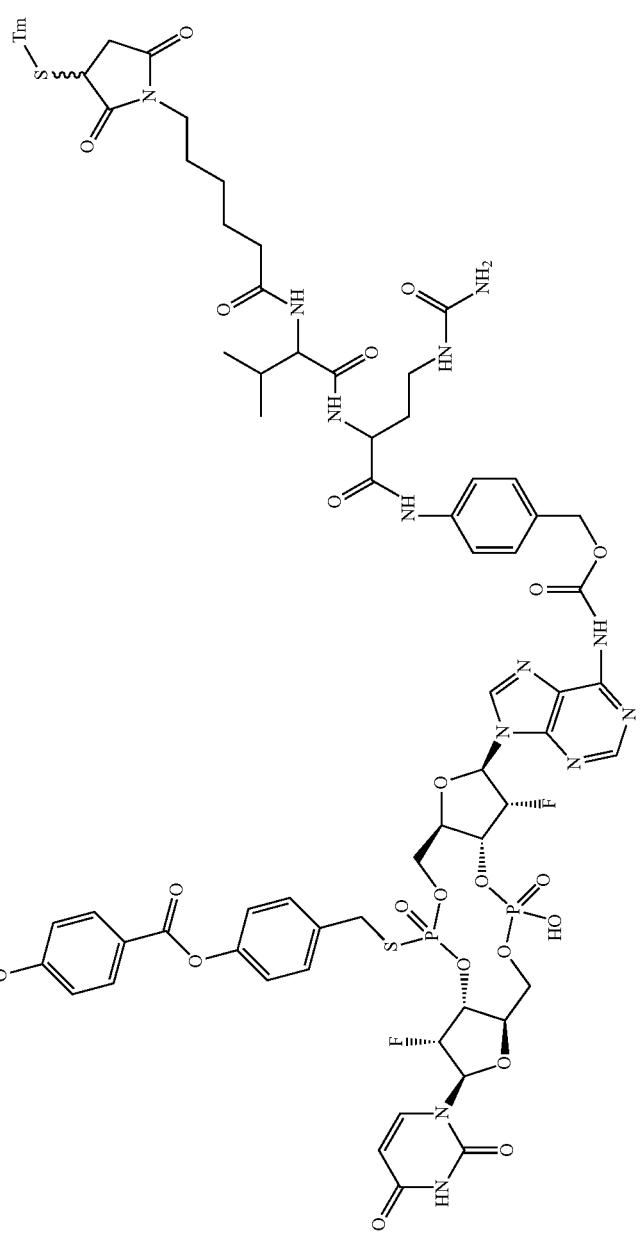 |
| 5 (Tm is a targetting moiety) | 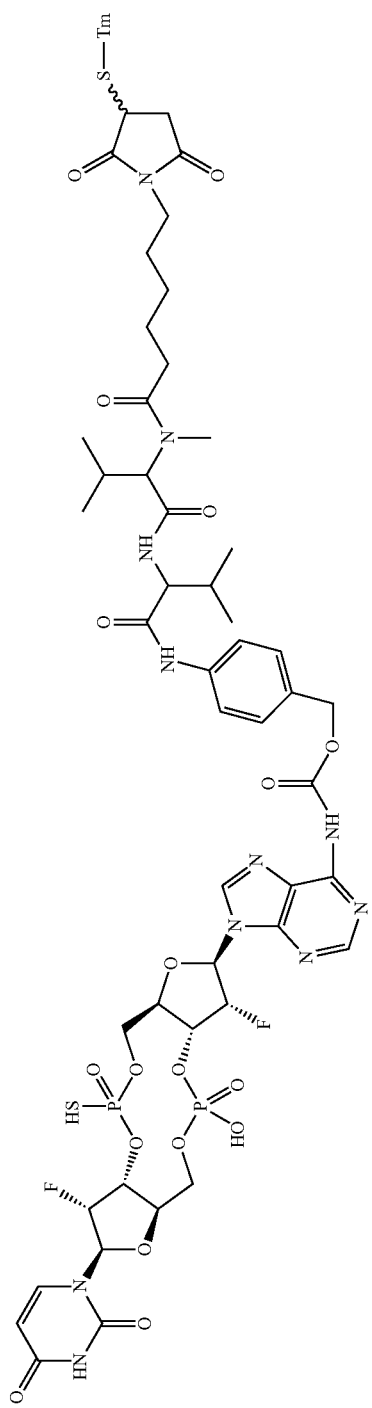 |

TABLE 1-continued
Compound
| Number | Compound |
|---|---|
| 6 (Tm is a targetting moiety) | 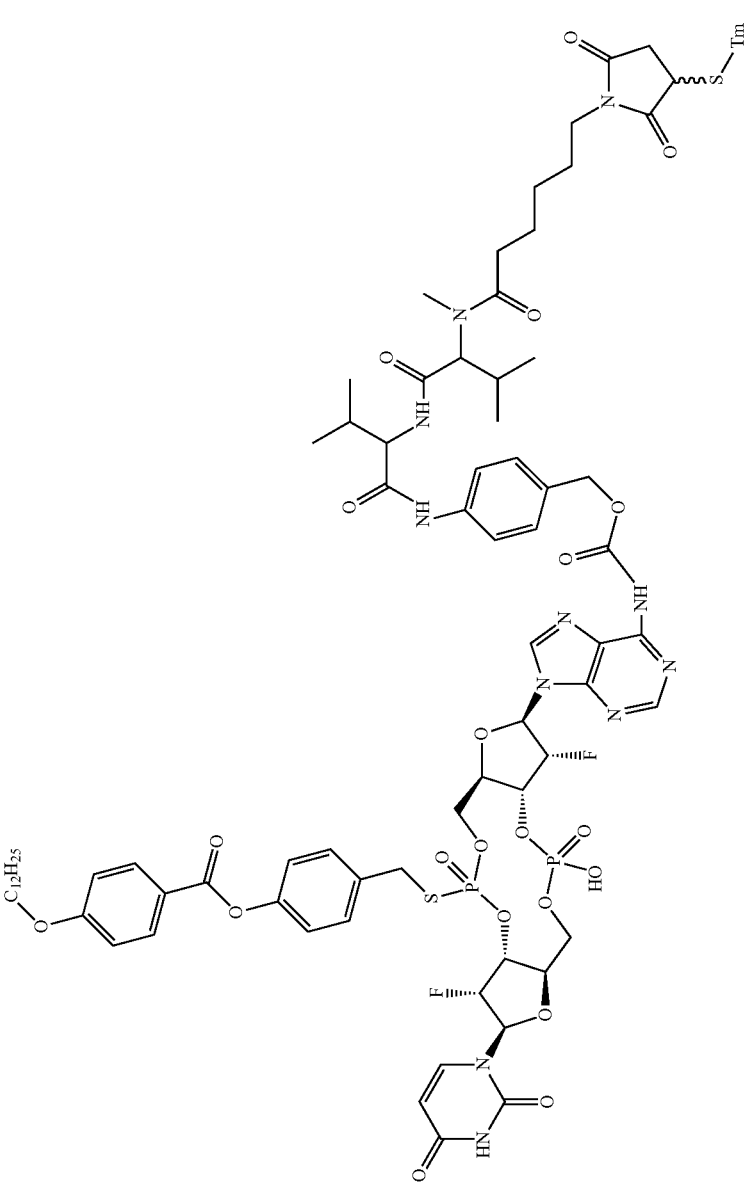 |

TABLE 1-continued

| Number | Compound |
|---|---|
| 7 | (structure) |

TABLE 1-continued
| Number | Compound |
|---|---|
| 8 | 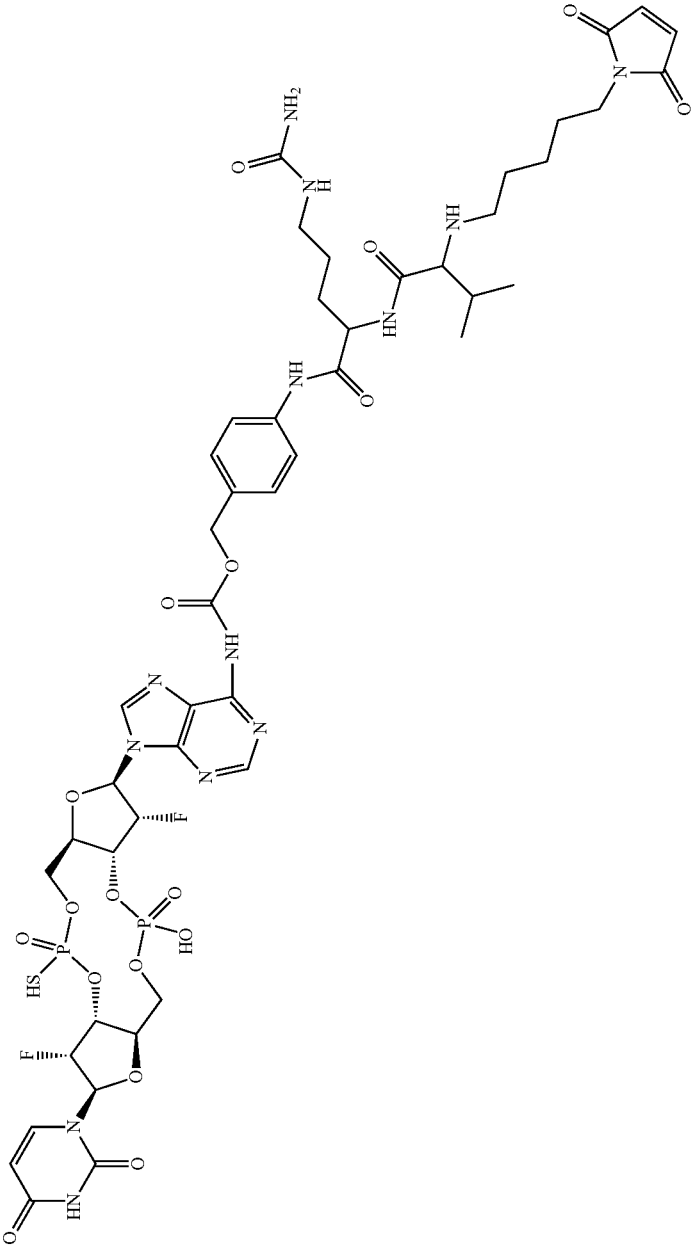 |

TABLE 1-continued
| Number | Compound |
|---|---|
| 9 (Tm is a targetting moiety) | 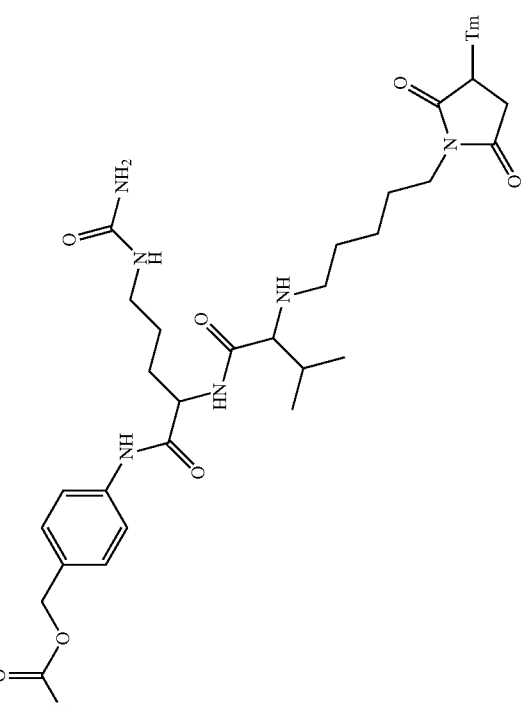 |
| 10 | 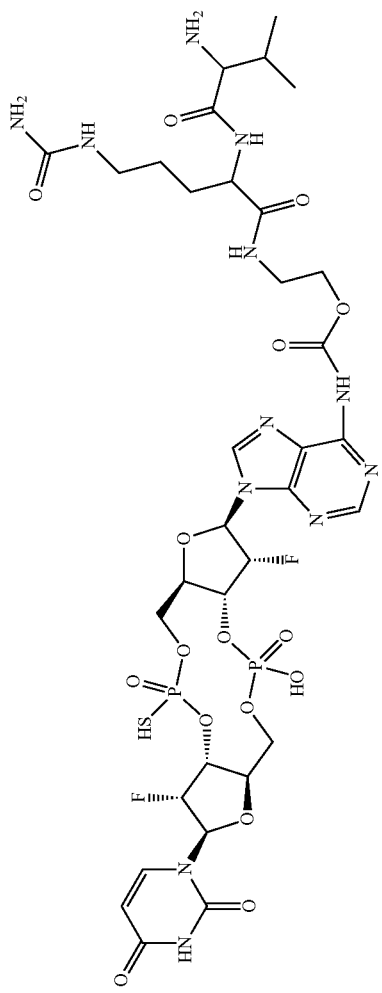 |

TABLE 1-continued
| Number | Compound |
|---|---|
| 11 | 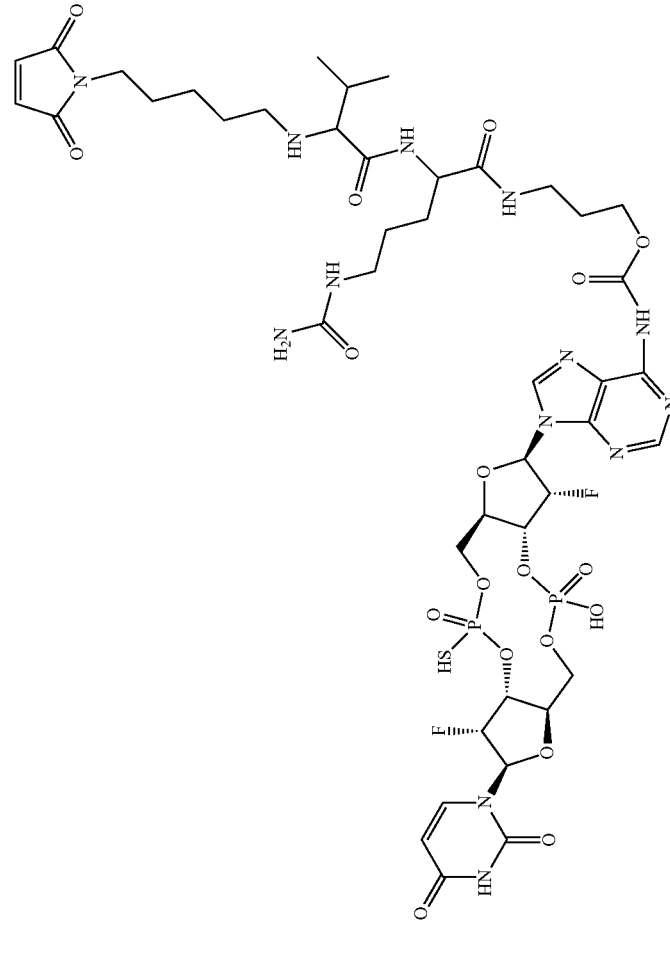 |

TABLE 1-continued
| Number | Compound |
|---|---|
| 12 | 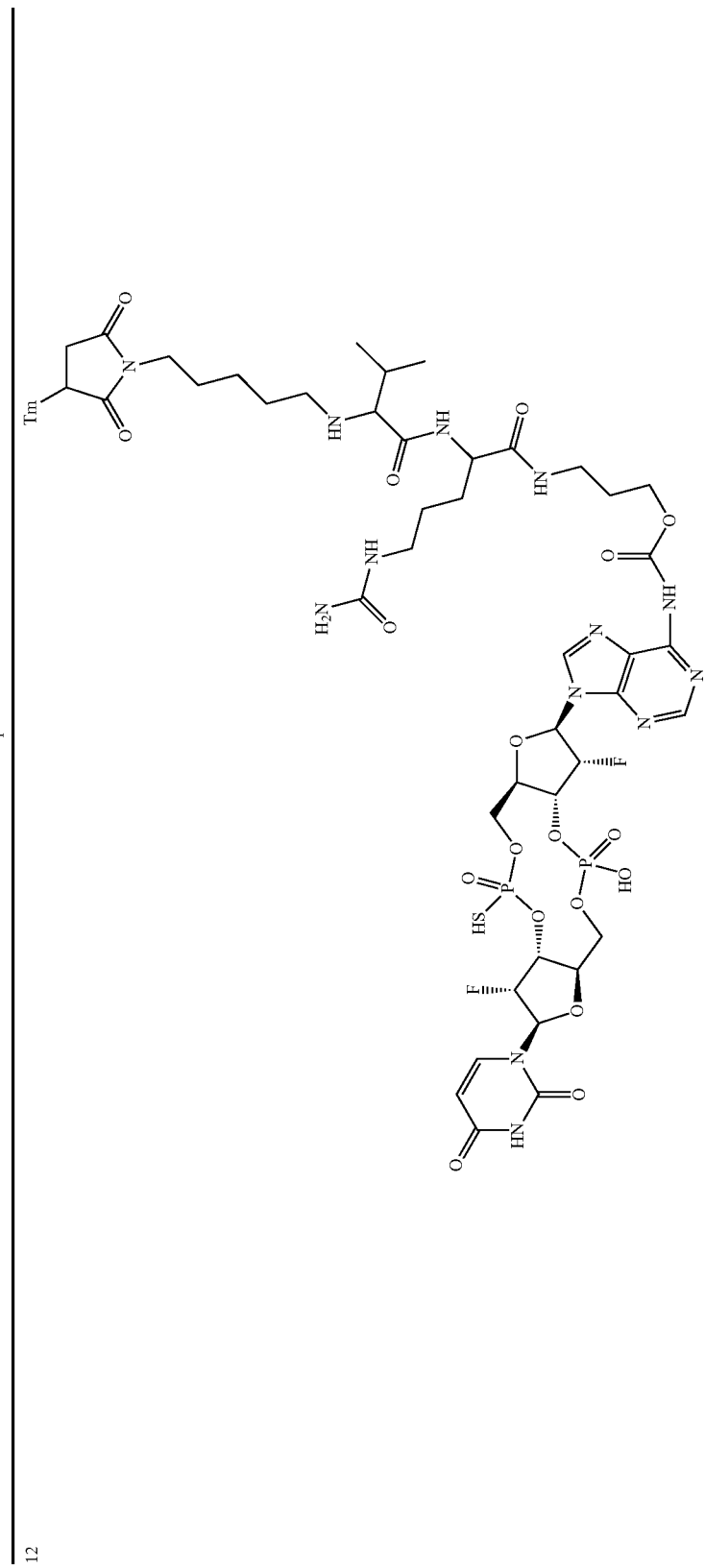 |

TABLE 1-continued

| Number | Compound |
|---|---|
| 13 | *(chemical structure)* |

TABLE 1-continued
| Number | Compound |
|---|---|
| 14 | 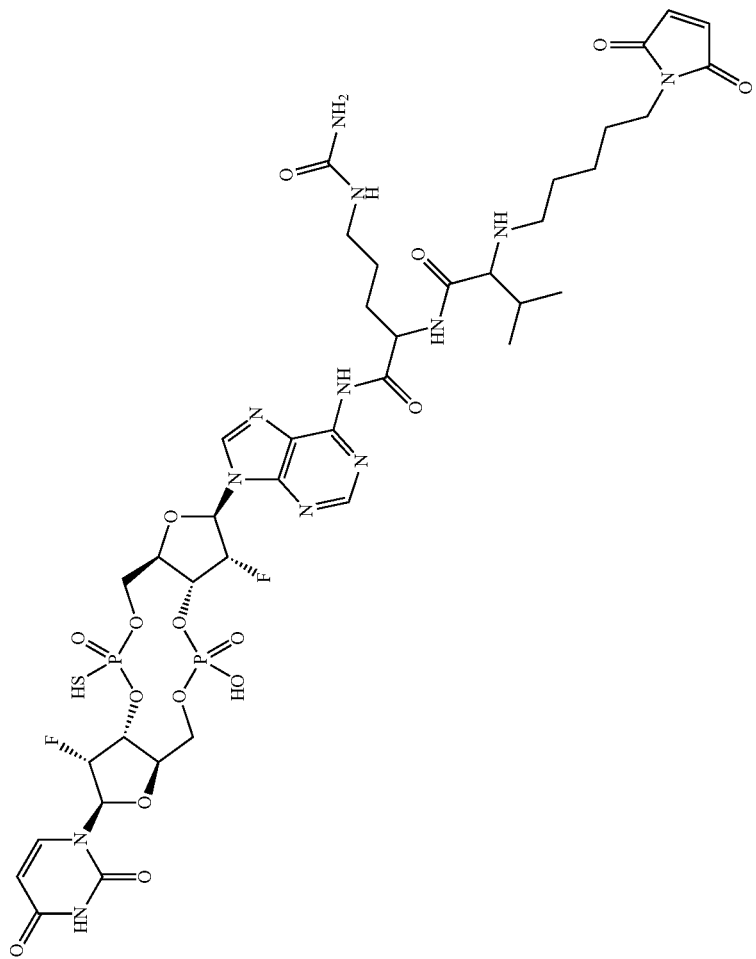 |

TABLE 1-continued
| Number | Compound |
|---|---|
| 15 | 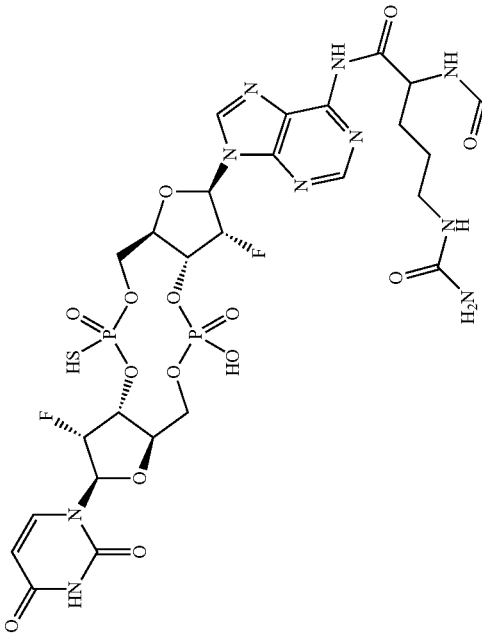 |

TABLE 1-continued

| Number | Compound |
|---|---|
| 16 | |
| 17 | |

TABLE 1-continued

| Number | Compound |
|---|---|
| 18 (Tm is a targetting moiety) | *[chemical structure]* |

TABLE 1-continued
| Number | Compound |
|---|---|
| 19 | 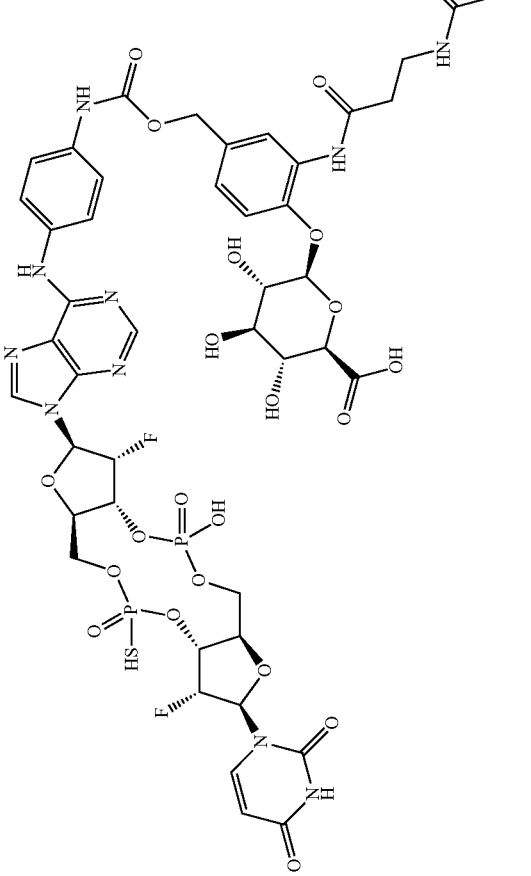 |

TABLE 1-continued
Compound
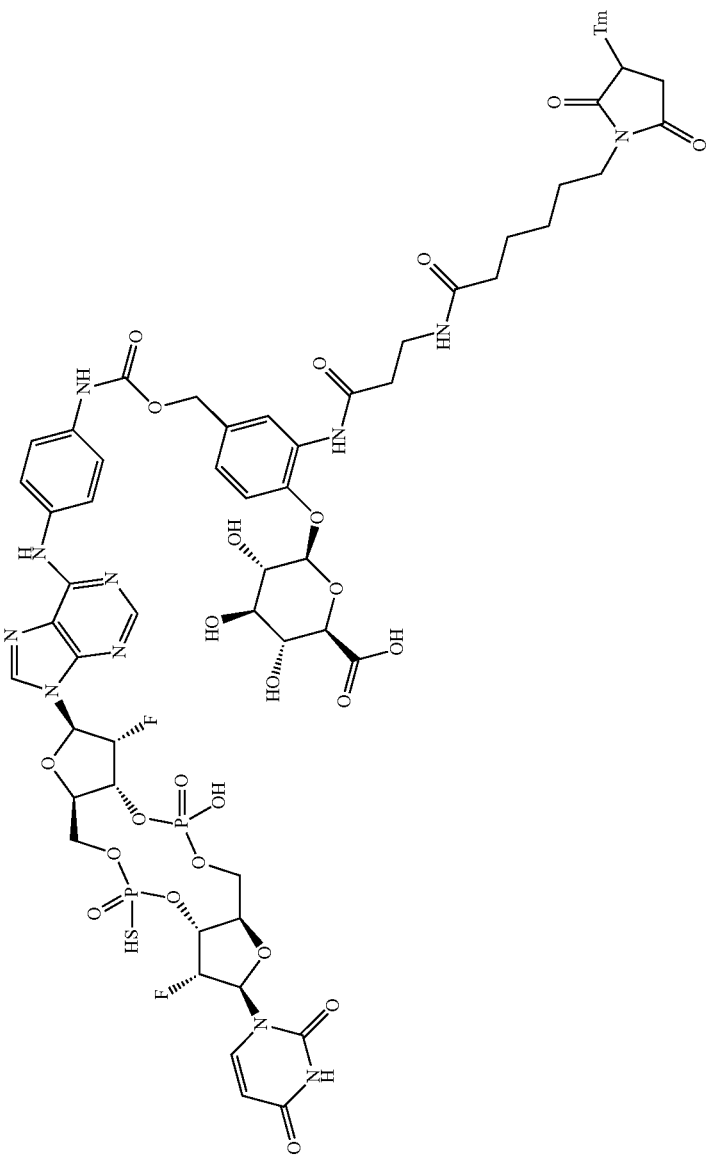
| Number |
|---|
| 20 (Tm is a targetting moiety) |

TABLE 1-continued
Number | Compound
--- | ---
21 | 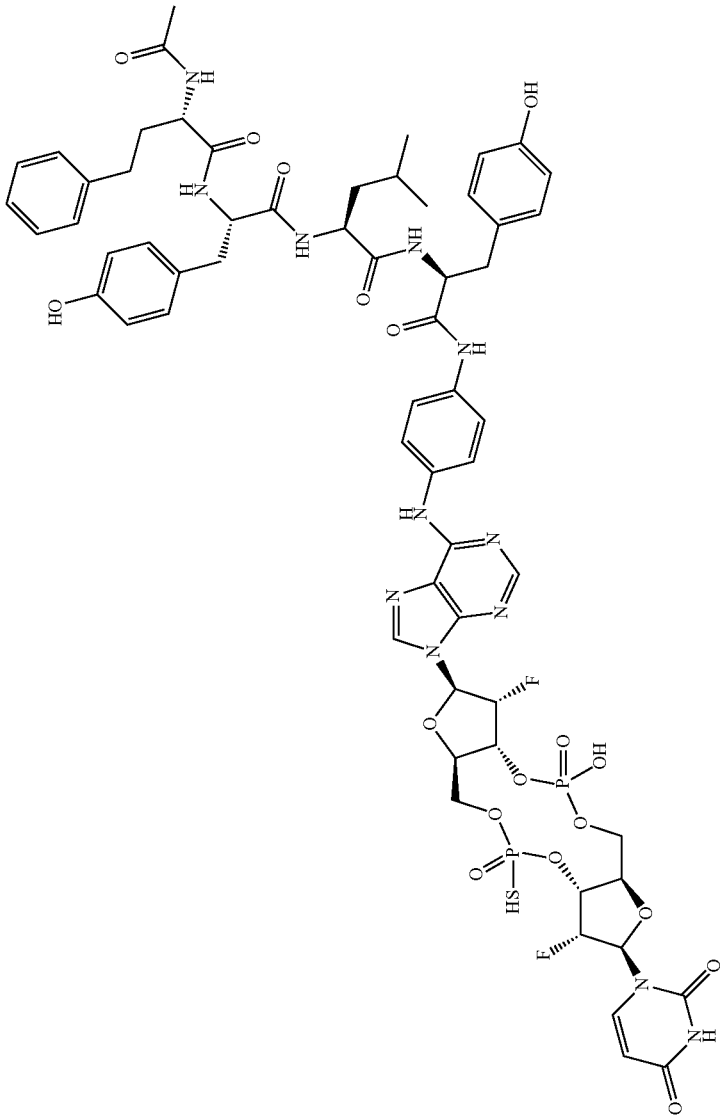 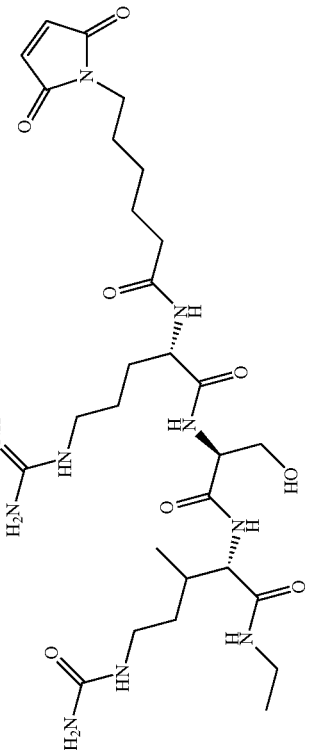

TABLE 1-continued
Compound
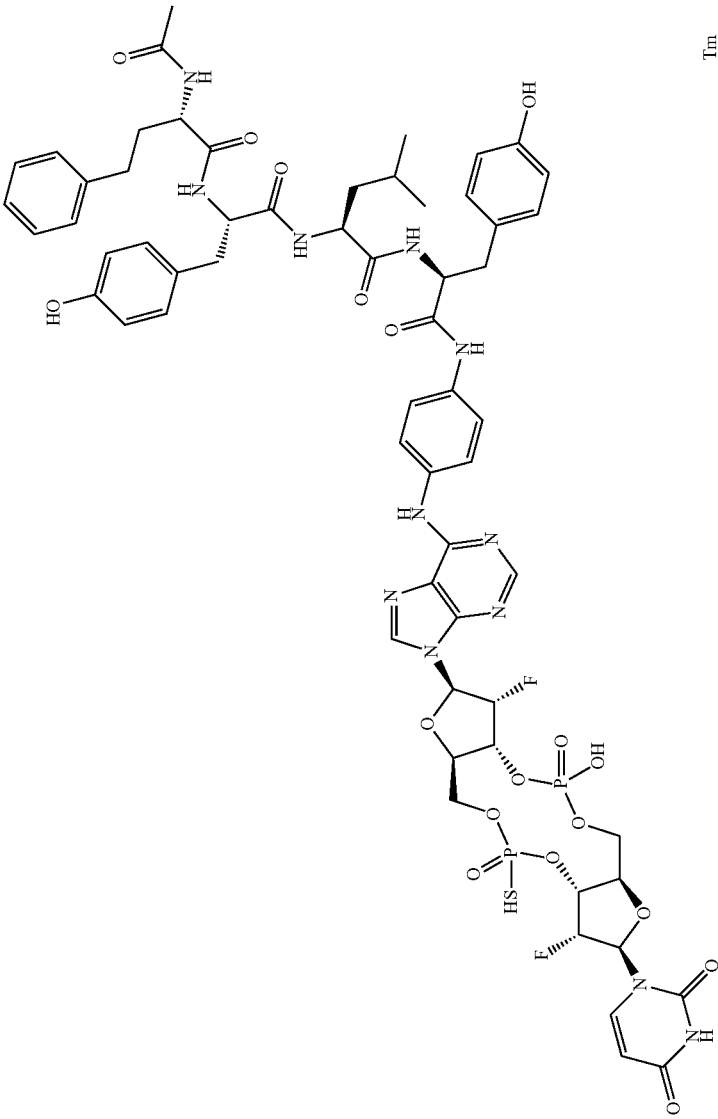
| Number |
|---|
| 22 (Tm is a targetting moiety) | or a pharmaceutically acceptable salt thereof; (herein Tm is a targeting moiety.

In an embodiment, a compound described herein is in the form of a pharmaceutically acceptable salt. Exemplary salts are described herein, such as ammonium salts. In some embodiments, the compound is a mono-salt. In some embodiments, the compound is a di-salt. In some embodiments, a compound described herein (e.g., a compound in Table 1) is not a salt (e.g., is a free acid or free base).

A compound of Formula (I) or Formula (II) is a small molecule nucleic acid hybrid (cyclic dinucleotide) compound that combines both antiviral and immune modulating activities. The latter activity mediates, for example, controlled apoptosis of virus-infected hepatocytes via stimulation of the innate immune response, similar to what is also achieved by IFN-α therapy in patients suffering from a viral infection.

Without wishing to be bound by theory, the mechanism of action of a compound of Formula (I) or Formula (II) entails its host immune stimulating activity which may induce endogenous IFNs via the activation of a PRR, e.g., RIG-I, NOD2, and STING. Activation may occur by binding of a compound of Formula (I) or Formula (II) to the nucleotide binding domain of a PRR (e.g., STING), as described previously, and may further result in the induction of PRR expression (e.g., STING expression).

The compounds provided herein may contain one or more asymmetric centers and thus occur as racemates and racemic mixtures, single enantiomers, individual diastereomers, and diastereomeric mixtures. All such isomeric forms of these compounds are expressly included within the scope. Unless otherwise indicated when a compound is named or depicted by a structure without specifying the stereochemistry and has one or more chiral centers, it is understood to represent all possible stereoisomers of the compound. The compounds provided herewith may also contain linkages (e.g., carbon-carbon bonds, phosphorus-oxygen bonds, or phosphorus-sulfur bonds) or substituents that can restrict bond rotation, e.g., restriction resulting from the presence of a ring or double bond.

In some embodiments, the method described herein comprises administration of a compound of Formula (I), or a pharmaceutically acceptable salt thereof. In some embodiments, the method described herein comprises administration of a compound of Formula (II), or a pharmaceutically acceptable salt thereof. In some embodiments, the compound of Formula (I) comprises an isomer (e.g., an Rp-isomer or Sp isomer) or a mixture of isomers (e.g., Rp-isomers or Sp isomers) of a compound of Formula (I In some embodiments, the compound of Formula (TT) comprises an isomer (e.g., an Rp-isomer or Sp isomer) or a mixture of isomers (e.g., Rp-isomers or Sp isomers) of a compound of Formula (II).

Methods of Use

The present disclosure relates to methods for inducing the expression of a PRR (e.g., STING) in a targeted manner utilising an ADC, in a subject through administration of a compound of Formula (I) Formula (II), or a pharmaceutically acceptable salt thereof. In some embodiments, the subject may be suffering from a condition described below, e.g., a viral infection (e.g., viral latency), a bacterial infection, a cancer (e.g., a proliferative disease).

Treatment of Viral Injections

Pattern recognition receptors such as STING, RIG-I, and NOD2, have been shown to be an important factor in host recognition of a large number of RNA viruses from a variety of different viral families. In some embodiments, the methods of inducing expression of PRRs (e.g., STING) disclosed herein comprise administering a therapeutically effective amount of a compound of Formula (I) or a pharmaceutically acceptable salt thereof to a subject infected with a microbial infection. In some embodiments, the microbial infection is a virus. In some embodiments, the virus is a RNA virus (e.g., a double-stranded RNA (dsRNA) virus, a single-stranded RNA (ssRNA) virus (e.g., a positive-strand (sense) ssRNA virus or a negative-strand (antisense) ssRNA virus), or a ssRNA retrovirus) or a DNA virus (e.g., a dsDNA virus, ssDNA virus, or a dsDNA retrovirus). In some embodiments, the virus may be a Group I, Group II, Group III, Group IV, Group V, Group VI, or Group VII class of virus, e.g., according to the Baltimore classification system.

In some embodiments, the virus is dsRNA virus, e.g., a Group III virus. In some embodiments, expression of a PRR (e.g., STING) is induced through host-produced or viral-derived RNA. In some embodiments, the virus is a dsRNA virus, and is a member of the Birnaviridae, Chrysoviridae, Cysloviridae, Endornaviridae, Hypoviridae, Megabirnaviridae, Partitiviridae, Picobirnaviridae, Reoviridae, or Totiviridae families, or other family of dsRNA virus. Exemplary dsRNA viruses and virus genera include, but are not limited to, Picobirnavirus, Rotavirus, Seadornavirus, Coltivirus, Orbivirus, and Orthoreovirus, or a subtype, species, or variant thereof.

In some embodiments, the virus is ssRNA virus, e.g., a positive-strand (sense) ssRNA virus, e.g., a Group IV virus. In some embodiments, expression of a PRR (e.g., STING) is induced through host-produced or viral-derived RNA. In some embodiments, the virus is a positive-strand (sense) ssRNA virus, and is a member of the Arteriviridae, Coronaviridae, Mesoniviridae, Roniviridae, Dicistroviridae, Iflaviridae, Marnaviridae, Piconaviridae, Secoviridae, Alphaflexiviridae, BetaJlexiviridae, GammaJlexiviridae, Tymoviridae, Alphatetraviridae, Alvernaviridae, Astroviridae, Barnaviridae, Bromoviridae, Caliciviridae, Carmotetraviridae, Closteroviridae, Flaviviridae, Leviviridae, Luteoviridae, Narnaviridae, Nodaviridae, Permutotetraviridae, Potyviridae, Togaviridae, or Virgaviridae families, or other family of positive-strand (sense) ssRNA virus. Exemplary positive-strand (sense) ssRNA viruses and virus genera include, but are not limited to, Yellow fever virus, West Nile virus, Hepatitis C virus, Dengue fever virus, Rubella virus, Ross River virus, Sindbis virus, Chikungya virus, Nonvalk virus, Japanese encephalitis virus, Tick-borne encephalitis virus, St. Louis encephalitis virus, Murray Valley encephalitis virus, Kyasanur Forest disease virus (e.g., Monkey disease virus), Western Equine encephalitis virus, Eastern Equine encephalitis virus, Venezuelan Equine encephalitis virus, Sapporo virus, Norovirus, Sapovirus, Calicivirus, Parechovirus, Hepatitis A virus, Rhinovirus (e.g., Rhinovirus A, Rhinovirus B, and Rhinovirus C), Enterovirus (e.g., Enterovirus A, Enterovirus B, Enterovirus C (e.g., poliovirus), Enterovirus D, Enterovirus E, Enterovirus F, Enterovirus G, or Enterovirus H), Apthovirus (e.g., Foot and mouth disease virus), Nidovirales (e.g., Cavally virus, Nam Dinh virus, Middle East respiratory syndrome coronavirus (MERS-CoV), Coronavirus HKU1, Coronavirus NL63, SARS-CoV, Coronavirus OC43, and Coronavirus 229E), Benyvirus, Blunevirus, Cilevirus, Hepevirus (e.g., Hepatitis E virus), Higrevirus, Idaeovirus, Negevirus, Ourmiavirus, Polemovirus, Sobemovirus, or Umbravirus, or a subtype, species, or variant thereof.

In some embodiments, the virus is a member of the genus Norovirus, or a subtype, species, or variant thereof. In some embodiments, the virus is the Norwalk virus, Hawaii virus, Snow Mountain virus, Mexico virus, Desert Shield virus, Southampton virus, Lordsdale virus, or Wilkinson virus, or a subtype or variant thereof. In some embodiments, the virus is a member of the genus Norovirus and can be classified as genogroup GI, genogroup GII, genogroup GIII, genogroup GIV, or genogroup GV.

In some embodiments, the virus is ssRNA virus, e.g., a negative-strand (antisense) ssRNA virus, e.g., a Group V virus. In some embodiments, expression of a PRR (e.g., STING) is induced through host-produced or viral-derived RNA. In some embodiments, the virus is a negative-strand (antisense) ssRNA virus, and is a member of the Bornaviridae, Piloviridae, Paramyxoviridae, Rhabdoviridae, Nyamzviridae, Arenaviridae, Bunyaviridae, Ophioviridae, or Orthomyxoviridae families, or other family of negative-strand (antisense) ssRNA virus. Exemplary negative-strand (antisense) ssRNA viruses and virus genera include, but are not limited to, Brona disease virus, Ebola virus, Marburg virus, Measles virus, Mumps virus, Nipah virus, Hendra virus, Respiratory syncytial virus, Influenza and Parainfluenza viruses, Metapneumovirus, Newcastle disease virus, Deltavirus (e.g., Hepatitis D virus), Dichohavirus, Emaravirus, Nyavirus, Tenuivirus, Varicosavirus, or a subtype, species, or variant thereof.

In some embodiments, the virus is an ssRNA retrovirus (ssRNA RT virus), e.g., a Group VI virus. In some embodiments, expression of a PRR (e.g., STING) is induced through host-produced or viral-derived RNA. In some embodiments, the virus is an ssRNA RT virus and is a member of the Metaviridae, Pseudoviridae, or Retrovzridae families, or other family of ssRNA RT virus. Exemplary ssRNA RT viruses and virus genera include, but are not limited to, Metavirus, Errantivirus, Alpharetrovirus (e.g., Avian leukosis virus, Rous sarcoma virus), Belaretrovirus (e.g., Mouse mammary tumor virus), Gammaretrovirus (e.g., Murine leukemia virus, Feline leukemia virus), Deltaretrovirus (e.g., human T-lymphotropic virus), Epsilonretrovirus (e.g., Walleye dermal sarcoma virus), Lentivirus (e.g., Human immunodeficiency virus 1 (HIV)), or a subtype, species, or variant thereof.

In some embodiments, the virus is a DNA virus, e.g., a dsDNA virus or an ssDNA virus. In some embodiments, the virus is a dsDNA virus, e.g., a Group I virus, and expression of a PRR (e.g., STING) is induced through host-produced or viral-derived RNA. In some embodiments, the virus is a dsDNA virus and is a member of the Myoviridae, Podovzridae, Siphoviridae, Alloherpesviridae, Herpesviridae, Malacoesviridae, Malacoherpesviridae, Lipothrixviridae, Rudiviridae, Adenoviridae, Ampullaviridae, Ascoviridae, Asfarviridae, Baculoviridae, Bicaudaviridae, Clavaviridae, Corticoviridae, Fuselloviridae, Globuloviridae, Guttaviridae, Hytrosaviridae, Iridoviridae, Marseilleviridae, Nimaviridae, Pandoraviridae, Papillomaviridae, Phycodnaviridae, Polydnaviruses, Polymaviridae, Poxviridae, Sphaerolipoviridae, Tectiviridae, or Turriviridae families, or other family of dsDNA virus. Exemplary dsDNA viruses and virus genera include, but are not limited to, Dinodnavirus, Nudivirus, smallpox, human herpes virus, Varicella Zoster virus, polyomavirus 6, polyomavirus 7, polyomavirus 9, polyomavirus 10, JC virus, BK virus, KI virus, WU virus, Merkel cell polyomavirus, Trichodysplasia spinulosa-associated polyomavirus, MX polyomavirus, Simian virus 40, or a subtype, species, or variant thereof.

In some embodiments, the virus is an ssDNA virus, e.g., a Group II virus, and expression of a PRR (e.g., STING) is induced through host-produced or viral-derived RNA. In some embodiments, the virus is an ssDNA virus and is a member of the Anelloviridae, Bacillariodnaviridiae, Bidnaviridae, Circoviridae, Geminiviridae, Inoviridae, Microviridae, Nanoviridae, Parvoviridae, or Spiraviridae families, or other family of ssDNA virus. Exemplary ssDNA viruses and virus genera include, but are not limited to, Torque teno virus, Torque teno midi virus, Torque teno mini virus, Gyrovirus, Circovirus, Parvovirus B19, Bocaparvovirus, Dependoparvovirus, Erythroparvovirus, Protoparvovirus, Tetraparvovirus, *Bombyx mori* densovirus type 2, lymphoidal parvo-like virus, Hepatopancreatic parvo-like virus, or a subtype, species, or variant thereof.

In some embodiments, the virus is a dsDNA reverse transcriptase (RT) virus, e.g., a Group VII virus, and expression of a PRR (e.g., STING) is induced through host-produced or viral-derived RNA. In some embodiments, the virus is a dsDNA RT virus and is a member of the Hepadnaviridae, or Caulimoviridae families, or other family of dsDNA RT virus. Exemplary dsDNA RT viruses and virus genera include, but are not limited to, Hepatitis B virus, or a subtype, species, or variant thereof.

In some embodiments, the virus (e.g., a virus described herein) is latent, e.g., within a cell. In some embodiments, the virus is an RNA virus (e.g., a double-stranded RNA (dsRNA) virus, a single-stranded RNA (ssRNA) virus (e.g., a positive-strand (sense) ssRNA virus or a negative-strand (antisense) ssRNA virus), or a ssRNA retrovirus) or a DNA virus (e.g., a dsDNA virus, ssDNA virus, or a dsDNA retrovirus) and is latent, e.g., within a cell. In some embodiments, the virus is a Group I, Group II, Group III, Group IV, Group V, Group VI, or Group VII class of virus, e.g., according to the Baltimore classification system, and is latent, e.g., within a cell.

In some embodiments, the virus is an RNA virus (e.g., an RNA virus described herein) and is latent, e.g., within a cell. In some embodiments, the virus is an ssRNA retrovirus (ssRNA RT virus), e.g., a Group VI virus, and is latent, e.g., within a cell. In some embodiments, the virus is the human immunodeficiency virus 1 (HIV)), or a subtype, species, or variant thereof, and is latent, e.g., within a cell.

In some embodiments, the methods of inducing expression of a PRR (e.g., STING) in a subject suffering from a viral infection disclosed herein result in an increase in PRR expression (e.g., STING expression). In some embodiments, expression of a PRR (e.g., STING) is induced by a factor of about 1.1, about 1.2, about 1.3, about 1.4, about 1.5, about 1.6, about 1.7, about 1.8, about 1.9, about 2, about 2.5, about 3, about 4, about 5, about 7.5, about 10, about 15, about 20, about 25, about 30, about 40, about 50, about 75, about 100, about 150, about 200, about 250, about 500, about 1000, about 1500, about 2500, about 5000, about 10,000, or more. In some embodiments, induction of expression of a PRR (e.g., STING) occurs within about 5 minutes of administration of a compound of Formula (I) or a pharmaceutically acceptable salt thereof. In some embodiments, induction of expression of a PRR (e.g., STING) occurs within about 10 minutes, about 15 minutes, about 20 minutes, about 25 minutes, about 30 minutes, about 45 minutes, about 1 hour, about 1.5 hours, about 2 hours, about 3 hours, about 4 hours, about 5 hours, about 6 hours, about 7 hours, about 8 hours, about 10 hours, about 12 hours or more following administration of a compound of Formula (I) or a pharmaceutically acceptable salt thereof to a subject.

Treatment of Bacterial Infections

Recent studies have shown that PRRs (e.g., STING) play a critical role in host recognition of bacterial infections stemming from a variety of species (Dixit, E. and Kagan, J. C. *Adv Immunol* (2013) 117:99-125). In some cases, bacteria may secrete nucleic acids during the exponential growth phase (e.g., *Listeria monocytogenes*; Abdullah, Z. et al, *EMBO J* (2012) 31:4153-4164), which in turn are detected by PRRs such as RIG-I and thus promote the induction of further PRR expression. In other cases, such as for *Legionella pneumophila*, bacterial DNA enters into the cytosol over the course of infection and is transcribed into an RNA ligand for RIG-I (Chiu, Y. H. et al, *Cell* (2009) 138:576-591), thus triggering downstream PRR-mediated signaling events. PRR expression (e.g., STING expression) may further be induced upon recognition of RNA released during phagocytotic uptake of bacteria. Additionally, bacterial cell wall components such as peptidoglycans (e.g., muramyl dipeptide, i.e., MDP) may serve as ligands for activation and induction of PRRs, namely NOD2, and bacterial-derived nucleic acids such as cyclic dinucleotides (e.g., cyclic di-GMP) may bind to and activate PRRs, in particular STING. In some embodiments, the expression of one or more PRRs may be induced through other means not explicitly recited herein.

In some embodiments, the methods of inducing expression of a PRR (e.g., STING) disclosed herein comprise administering a therapeutically effective amount of a compound of Formula (I) or a pharmaceutically acceptable salt thereof to a subject infected with a microbial infection, e.g., a bacterial infection.

In some embodiments, the methods of inducing expression of a PRR (e.g., STING) disclosed herein comprise administering a therapeutically effective amount of a compound of Formula (II) or a pharmaceutically acceptable salt thereof to a subject infected with a microbial infection, e.g., a bacterial infection. In some embodiments, the bacterium is a Gram-negative bacterium or a Gram-positive bacterium. Exemplary bacteria include, but are not limited to, *Listeria* (e.g., *Listeria monocytogenes*), *Francisella* (e.g., *Francisella tularensis*), Mycobacteria (e.g., *Mycobacleria tuberculosis*), *Brucella* (e.g., *Brucella abortis*), *Streptococcus* (e.g., group B *Streptococcus*), *Legionella* (e.g., *Legionella pneumophila*), *Escherichia* (e.g., *Escherichia coli*), *Pseudomonas* (e.g., *Psuedomonas aeruginosa*), *Salmonella* (e.g., *Salmonella tphi*), *Shigella* (e.g., *Shigella flexneri*), *Campylobacter* (e.g., *Campylobacter jejuni*), *Clostridium* (e.g., *Clostrodium botulinum*), *Enterococcus* (e.g., *Enterococcus faecalis*), *Vibrio* (e.g., *Vibrio cholera*), *Yersinia* (e.g., *Yersinia pestis*), *Staphylococcus* (e.g., *Staphylococcus aureus*), or other genera, species, subtypes, or variants thereof.

In some embodiments, the methods of inducing expression of a PRR (e.g., STING) in a subject suffering from a bacterial infection disclosed herein result in an increase in PRR expression (e.g., STING expression). In some embodiments, expression of a PRR (e.g., STING) is induced by a factor of about 1.1, about 1.2, about 1.3, about 1.4, about 1.5, about 1.6, about 1.7, about 1.8, about 1.9, about 2, about 2.5, about 3, about 4, about 5, about 7.5, about 10, about 15, about 20, about 25, about 30, about 40, about 50, about 75, about 100, about 150, about 200, about 250, about 500, about 1000, about 1500, about 2500, about 5000, about 10,000, or more. In some embodiments, induction of expression of a PRR (e.g., STING) occurs within about 5 minutes of administration of a compound of Formula (I) or a pharmaceutically acceptable salt thereof. In some embodiments, induction of expression of a PRR (e.g., STING) occurs within about 10 minutes, about 15 minutes, about 20 minutes, about 25 minutes, about 30 minutes, about 45 minutes, about 1 hour, about 1.5 hours, about 2 hours, about 3 hours, about 4 hours, about 5 hours, about 6 hours, about 7 hours, about 8 hours, about 10 hours, about 12 hours or more following administration of a compound of Formula (I) or a pharmaceutically acceptable salt thereof.

Treatment of Cancer

It has been reported that many patients with advanced solid tumors show a spontaneous T cell-inflamed tumor microenvironment, which is predictive of prognosis and clinical response to immunotherapies. Recent findings suggest the STING pathway of cytosolic DNA sensing is an important innate immune sensing mechanism driving type I IFN production in the tumor context. Knowledge of this pathway is guiding the further development of novel immunotherapeutic strategies.

It has been reported that in early-stage colorectal cancer, the presence of activated CD8+ T cells within the tumor microenvironment significant positive prognostic outcome. Patients with other solid tumor histology also appear to have a spontaneous T cell infiltrate that may have similar positive prognostic value. These include breast cancer, renal cell carcinoma, melanoma, ovarian cancer, and gastrointestinal tumors. It is believed that T cell infiltrate includes tumor antigen-specific T cells that have been activated spontaneously in response to the growing tumor, perhaps through immune surveillance mechanisms. This attempted host immune response, even if it does not eliminate the tumor completely, is thought to delay tumor progression and thus yield improved clinical outcome. Furthermore, the innate immune mechanisms can lead to adaptive T cell response against tumor antigens even in the absence of exogenous infection. In this regard, human cancer gene expression profiling studies reveal an association between a type I IFN signature, T cell infiltration, and clinical outcome. Thus, innate immune sensing pathways that trigger type I IFN production might represent crucial intermediate mechanistic step. In gene expression profiling of melanoma, two major subsets of tumor microenvironment has been found that represent either the presence or absence of a transcriptional profile indicative of T cell infiltrate. In fact, CD8+ T cells, macrophages, as well as of some B cells and plasma cells in these lesions in melanoma metastases is similar to the phenotype described in early-stage colon cancer and other tumors in which activated T cells have been associated with favorable prognosis. CD8+ T cells were required for the up-regulation of all immune factors within the tumor microenvironment. Studies indicate that IFN production is necessary for optimal T cell priming against tumor antigens. There are many PRRs that trigger IFN-β production by host DCs in response to a growing tumor in vivo including STING. STING is an adapter protein that is activated by cyclic dinucleotides generated by cyclic GMP-AMP synthase (cGAS), which in turn is directly activated by cytosolic DNA. In the presence of these cyclic dinucleotides and/or DNA, STING is translocated from the endoplasmic reticulum to various perinuclear components; for example, palmitoylation of STING at the Golgi has been shown to be essential for STING activation (Mukai, K. et al (2016) *Nat Commun* doi:10.1038/ncomms11932).

Activated STING forms aggregates, activates TBK1, which in turn phosphorylates interferon regulatory factor 3 (IRF3) that directly contributes to type I IFN gene transcription. This pathway has been implicated in the sensing of DNA viruses, and also in selected autoimmune models. Moreover, activating mutations of STING have recently been identified in human patients with a vasculitis/pulmonary inflammation syndrome that is characterized by increased type I IFN production. Mechanistic studies using mouse transplantable tumor models revealed that STING-knockout mice, and IRF3-knockout mice showed defective spontaneous T cell priming against tumor antigens in vivo, and rejection of immunogenic tumors was ablated. Similarly, tumor-derived DNA was found within the cytosol of a major population of tumor-infiltrating DCs, and this was associated with STING pathway activation and IFN-β production. Therefore, the host STING pathway appears to be an important innate immune sensing pathway that detects the presence of a tumor and to drive DC activation and subsequent T cell priming against tumor-associated antigens in vivo. A functional role for the STING pathway in vivo has also been reported in other mouse-tumor systems. An inducible glioma model was shown to result in induction of a type I IFN gene signature as part of the host response. This induction was substantially reduced in STING-knockout mice, and tumors grew more aggressively, leading to shorter mouse survival. Exogenous delivery of cyclic dinucleotides as STING agonists exerted a therapeutic effect in vivo. A crucial role for host type I IFNs and the host STING pathway was also confirmed in the B16.OVA and EL4.OVA models in response to cryo-ablation. Interestingly, the mechanisms involved paralleled what was observed in the Bm12 mouse model of lupus because host STING was also required for maximal production of anti-DNA antibodies. Thus, the antitumor immune response triggered in part by tumor DNA has overlap with the mechanisms involved in autoimmunity driven by extracellular DNA. A role for STING also has been explored in an inducible colon cancer model. It seems likely that the ability of a cancer in an individual patient to support STING pathway activation is linked to the spontaneous generation of a T cell-inflamed tumor microenvironment. Because this phenotype is associated with improved prognosis of early-stage cancer patients, and also with clinical response to immunotherapies in the metastatic setting, failed STING activation may therefore represent an early functional block, and thus itself may have prognostic/predictive value as a biomarker. Second, strategies that activate or mimic the output of the host STING pathway should have immunotherapeutic potential in the clinic. In as much as non-T cell-inflamed tumors appear to lack evidence of a type I IFN transcriptional signature, strategies to promote robust innate signaling via APCs in the tumor microenvironment might facilitate improved cross-priming of tumor antigen-specific CD8+ T cells, and also augment chemokine production for subsequent oncolytic activity.

Recognition of nucleic acid ligands by a PRRs such as cGAS, RIG-I and/STING stimulates the production of type I interferons (e.g., IFN-α or IFN-β), thus triggering a series of downstream signaling events that may lead to apoptosis in susceptible cells. In recent years, a connection between the induction of PRR expression and a number of cancers has been discovered. For example, RIG-I expression has been shown to be significantly downregulated in hepatocellular carcinoma, and patients exhibiting low RIG-I expression in tumors had shorter survival and poorer responses to IFN-α therapy (Hou, J. et al, *Cancer Cell* (2014) 25:49-63). As such, it has been suggested that the level of RIG-I expression may be useful as a biomarker for prediction of prognosis and response to immunotherapy. In other cases, induction of RIG-I expression has been shown to induce immunogenic cell death of pancreatic cancer cells, prostate cancer cells, breast cancer cells, skin cancer cells, and lung cancer cells (Duewell, P. et al, *Cell Death Differ* (2014) 21:1825-1837; Besch, R. et al, *J Clin Invest* (2009) 119: 2399-2411; Kaneda, Y. *Oncoimmunology* (2013) 2:e23566; Li, X. Y. et al, *Mol Cell Oncol* (2014) 1:e968016), highlighting a new approach in immune-mediated cancer treatment.

STING is recognized as the key adapter protein in the cGAS-STING-IFN cascade, although it is also reported to be a sensor for DNA. A role for STING in the stimulation of innate immunity in response to cancer has also been identified. Recent studies have revealed the presence of tumor-derived DNA in the cytosol of certain antigen-presenting cells, such as tumor-infiltrating dendritic cells, likely generated through tumor cell stress or cell death. This tumor-derived DNA is known to activate cGAS which causes the production of cyclic nucleotides that have been shown to activate STING, resulting in production of associated type 1 interferons (Woo, S. R. et al, *Immunity* (2014) 41:830-842). Stimulation of STING and resulting downstream signaling pathways also likely contributes to effector T cell recruitment into the inflamed tumor microenvironment (Woo, S. R. *Trends in Immunol* (2015) 36:250-256). STING activation in the tumor microenvironment can induce adaptive immune response leading to anti-tumor activity. Hence, in those tumors that are STING-deficient, the described herein can still have anti-tumor activity through activation of antigen-presenting cells and dendritic cells, (APCs and DCs) and induction of adaptive immune response.

Antibody Drug Conjugates

Antibody drug conjugates (ADCs) are an important class of biopharmaceutical drugs, which are designed to act as a targeted therapy for the treatment of subjects with various disease states (Ducry, L. *Bioconjugate Chemistry* (2010) 21:5-13). ADCs are comprised of a small molecule covalently linked to an antibody. The covalent linkage comprises a point of attachment to the small molecule, a biocompatible linker unit, and a self-immolative group attached to the antibody. In some aspects, there is an optional biocompatible spacer group between the self-immolative group and the antibody.

Cancer and Antibody Drug Conjugates

In the field of cancer chemotherapeutics, ADCs combine the specificity of antibodies with the potent anti-tumor effects of cytotoxic drugs. In recent literature. ADCs have emerged as powerful methods for the targeted treatment of cancer. Two ADC products, brentuximab vedotin (Adcetris®) and trastuzumab emtansine (Kadcyla®), have received FDA approval and there are more than 40 ADC candidates in clinical trials for the treatment of various cancers (Yejin. K. *J Pharm. Investigation*. (2016) 46:341-349).

Anti-Microbial Antibody Drug Conjugates

Recently, the field of ADC development has extended to the treatment of microbial infections. The increase of bacterial resistance to traditional antibiotics has reached alarming levels, thus necessitating a strong need to develop new antimicrobial agents. These new antimicrobials need to possess novel modes of action and/or different cellular targets compared with the existing antibiotics in order to overcome microbial resistance. As a result, new classes of compounds designed to avoid resistance mechanisms are undergoing preclinical and clinical evaluation. In both traditional and newly developed antibiotics, the target selectivity lies in the drug itself, in its ability to affect a mechanism that is unique to microbial life. As a result, a number of potent agents have been excluded from use as therapeutics, as they affect both the pathogen and the host cells. Such compounds could be reconsidered for clinical as antimicrobials if they were incorporated into part of a targeted delivery platform where the drug selectivity is replaced by target-selectivity borne by the targeting moiety. With a large number of antibodies and antibody-drug conjugates already approved or near approval as cancer therapeutics, targeted therapy is becoming increasingly attractive for other, non-chemotherapeutic uses (Yacoby, B; *Infect Discord Drug Targets* 2007 7(3):221-9).

The combination of the PRR modulators described herein and the target specificity of ADCs represents an attractive and powerful new approach to the treatment of diseases such, but not limited to, cancer, microbial and viral infections when compared to existing methods of treatment.

In some embodiments, the methods of inducing expression of a PRR (e.g., a PRR described herein) comprise administering a therapeutically effective amount of a compound of Formula (I) or a pharmaceutically acceptable salt thereof to a subject suffering from cancer.

In some embodiments, the methods of inducing expression of a PRR (e.g., a PRR described herein) comprise administering a therapeutically effective amount of a compound of Formula (II) or a pharmaceutically acceptable salt thereof to a subject suffering from cancer.

In some embodiments, the methods of inducing expression of STING disclosed herein comprise administering a therapeutically effective amount of a compound of Formula (I) or a pharmaceutically acceptable salt thereof to a subject suffering from cancer.

In some embodiments, the methods of inducing expression of STING disclosed herein comprise administering a therapeutically effective amount of a compound of Formula (IT) or a pharmaceutically acceptable salt thereof to a subject suffering from cancer.

In some embodiments, the methods of inducing expression of RIG-I disclosed herein comprise administering a therapeutically effective amount of a compound of Formula (I) or a pharmaceutically acceptable salt thereof to a subject suffering from cancer.

In some embodiments, the methods of inducing expression of RIG-I disclosed herein comprise administering a therapeutically effective amount of a compound of Formula (II) or a pharmaceutically acceptable salt thereof to a subject suffering from cancer.

In some embodiments, the methods of inducing expression of NOD2 disclosed herein comprise administering a therapeutically effective amount of a compound of Formula (I) or a pharmaceutically acceptable salt thereof to a subject suffering from cancer.

In some embodiments, the methods of inducing expression of NOD2 disclosed herein comprise administering a therapeutically effective amount of a compound of Formula (II) or a pharmaceutically acceptable salt thereof to a subject suffering from cancer.

In some embodiments, the cancer is selected from a cancer of the breast, bone, brain, cervix, colon, gastrointestinal tract, eye, gall bladder, lymph nodes, blood, lung, liver, skin, mouth, prostate, ovary, penis, pancreas, uterus, testicles, stomach, thymus, thyroid, or other part of the body. In some embodiments, the cancer comprises a solid tumor (e.g., a carcinoma, a sarcoma, or a lymphoma). In some embodiments, the cancer is a hepatocellular carcinoma or other cancer of the liver. In some embodiments, the cancer is a leukemia or other cancer of the blood. In some embodiments, the cancer comprises breast cancer, renal cell carcinoma, colon cancer, melanoma, ovarian cancer, head and neck squamous cell carcinoma, pancreatic cancer, prostate cancer, lung cancer, brain cancer, thyroid cancer, renal cancer, testis cancer, stomach cancer, urothelial cancer, skin cancer, cervical cancer, endometrial cancer, liver cancer, lung cancer, lymphoma or gastrointestinal stromal cancer and solid tumors. In some embodiments, the cancer cells (e.g., tumor cells) comprise specific cancer-associated antigens that induce a T-cell-mediated anti-tumor response.

In some embodiments, the methods of inducing expression of a PRR (e.g., STING, RIG-I, MDA5, LGP2) in a subject suffering from a cancer disclosed herein result in an increase in PRR expression (e.g., STING expression). In some embodiments, expression of a PRR (e.g., STING) is induced by a factor of about 1.1, about 1.2, about 1.3, about 1.4, about 1.5, about 1.6, about 1.7, about 1.8, about 1.9, about 2, about 2.5, about 3, about 4, about 5, about 7.5, about 10, about 15, about 20, about 25, about 30, about 40, about 50, about 75, about 100, about 150, about 200, about 250, about 500, about 1000, about 1500, about 2500, about 5000, about 10,000, or more.

In some embodiments, induction of expression of a PRR (e.g., STING) occurs within about 5 minutes of administration of a compound of Formula (I) or a pharmaceutically acceptable salt thereof.

In some embodiments, induction of expression of a PRR (e.g., STING) occurs within about 5 minutes of administration of a compound of Formula (II) or a pharmaceutically acceptable salt thereof.

In some embodiments, induction of expression of a PRR (e.g., STING) occurs within about 5 minutes of administration of a compound of Formula (I) or a pharmaceutically acceptable salt thereof.

In some embodiments, induction of expression of a PRR (e.g., STING) occurs within about 5 minutes of administration of a compound of Formula (II) or a pharmaceutically acceptable salt thereof.

In some embodiments, induction of expression of a PRR (e.g., STING) occurs within about 10 minutes, about 15 minutes, about 20 minutes, about 25 minutes, about 30 minutes, about 45 minutes, about 1 hour, about 1.5 hours, about 2 hours, about 3 hours, about 4 hours, about 5 hours, about 6 hours, about 7 hours, about 8 hours, about 10 hours, about 12 hours or more following administration of a compound of Formula (I) or a pharmaceutically acceptable salt thereof.

In some embodiments, induction of expression of a PRR (e.g., STING) occurs within about 10 minutes, about 15 minutes, about 20 minutes, about 25 minutes, about 30 minutes, about 45 minutes, about 1 hour, about 1.5 hours, about 2 hours, about 3 hours, about 4 hours, about 5 hours, about 6 hours, about 7 hours, about 8 hours, about 10 hours, about 12 hours or more following administration of a compound of Formula (II) or a pharmaceutically acceptable salt thereof.

It is recognized that activation of STING by compounds may lead to induction of expression of other PRRs such as RIG-I, MDA5, NOD2 etc. which may further amplify IFN production in the tumor microenvironment and prime T-cells for enhanced anti-tumor activity.

In some embodiments, the methods of inducing expression of a PRR (e.g., STING) in a subject suffering from a cancer disclosed herein result in an increase in PRR expression (e.g., STING expression). In some embodiments, expression of a PRR (e.g., STING) is induced by a factor of about 1.1, about 1.2, about 1.3, about 1.4, about 1.5, about 1.6, about 1.7, about 1.8, about 1.9, about 2, about 2.5, about 3, about 4, about 5, about 7.5, about 10, about 15, about 20, about 25, about 30, about 40, about 50, about 75, about 100, about 150, about 200, about 250, about 500, about 1000, about 1500, about 2500, about 5000, about 10,000, or more.

In some embodiments, induction of expression of a PRR (e.g., STING) occurs within about 5 minutes of administration of a compound of Formula (I) or a pharmaceutically acceptable salt or stereoisomer thereof.

In some embodiments, induction of expression of a PRR (e.g., STING) occurs within about 5 minutes of administration of a compound of Formula (II) or a pharmaceutically acceptable salt or stereoisomer thereof.

In some embodiments, induction of expression of a PRR (e.g., STING) occurs within about 10 minutes, about 15 minutes, about 20 minutes, about 25 minutes, about 30 minutes, about 45 minutes, about 1 hour, about 1.5 hours, about 2 hours, about 3 hours, about 4 hours, about 5 hours, about 6 hours, about 7 hours, about 8 hours, about 10 hours, about 12 hours or more following administration of a compound of Formula (I) or a pharmaceutically acceptable salt thereof.

In some embodiments, induction of expression of a PRR (e.g., STING) occurs within about 10 minutes, about 15 minutes, about 20 minutes, about 25 minutes, about 30 minutes, about 45 minutes, about 1 hour, about 1.5 hours, about 2 hours, about 3 hours, about 4 hours, about 5 hours, about 6 hours, about 7 hours, about 8 hours, about 10 hours, about 12 hours or more following administration of a compound of Formula (II) or a pharmaceutically acceptable salt thereof.

Pharmaceutical Compositions

The present disclosure features methods for inducing the expression of a PRR (e.g., STING) in a subject, the methods comprising administering a compound of Formula (I), or Formula (II) or a pharmaceutically acceptable salt thereof.

While it is possible for the compound of the present disclosure (e.g., a compound of Formula (I)) to be administered alone, it is preferable to administer said compound as a pharmaceutical composition or formulation, where the compounds are combined with one or more pharmaceutically acceptable diluents, excipients or carriers. The compounds according to the disclosure may be formulated for administration in any convenient way for use in human or veterinary medicine. In certain embodiments, the compounds included in the pharmaceutical preparation may be active itself, or may be a prodrug, e.g., capable of being converted to an active compound in a physiological setting. Regardless of the route of administration selected, the compounds of the present disclosure, which may be used in a suitable hydrated form, and/or the pharmaceutical compositions of the present disclosure, are formulated into a pharmaceutically acceptable dosage form such as described below or by other conventional methods known to those of skill in the art.

The amount and concentration of compounds of the present disclosure (e.g., a compound of Formula (I) or Formula (II)) in the pharmaceutical compositions, as well as the quantity of the pharmaceutical composition administered to a subject, can be selected based on clinically relevant factors, such as medically relevant characteristics of the subject (e.g., age, weight, gender, other medical conditions, and the like), the solubility of compounds in the pharmaceutical compositions, the potency and activity of the compounds, and the manner of administration of the pharmaceutical compositions. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

Thus, another aspect of the present disclosure provides pharmaceutically acceptable compositions comprising a therapeutically effective amount or prophylactically effective amount of a compound described herein (e.g., a compound of Formula (I) or Formula (II)), formulated together with one or more pharmaceutically acceptable carriers (additives) and/or diluents. As described in detail below, the pharmaceutical compositions of the present disclosure may be specially formulated for administration in solid or liquid form, including those adapted for oral, intratumoral, parenteral administration, for example, by subcutaneous, intramuscular, intraperitoneal, or intravenous injection as, for example, a sterile solution or suspension. However, in certain embodiments the subject compounds may be simply dissolved or suspended in sterile water. In certain embodiments, the pharmaceutical preparation is non-pyrogenic, i.e., does not elevate the body temperature of a patient.

The phrases "systemic administration," "administered systemically," "peripheral administration" and "administered peripherally" as used herein mean the administration of the compound other than directly into the central nervous system, such that it enters the patient's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, stabilizing agent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include, but are not limited to: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) ascorbic acid; (17) pyrogen-free water; (18) isotonic saline; (19) Ringer's solution; (20) ethyl alcohol; (21) phosphate buffer solutions; (22) cyclodextrins such as Captisol®; and (23) other non-toxic compatible substances such as antioxidants and antimicrobial agents employed in pharmaceutical formulations.

As set out above, certain embodiments of the compounds described herein may contain a basic functional group, such as an amine, and are thus capable of forming pharmaceutically acceptable salts with pharmaceutically acceptable acids. The term "pharmaceutically acceptable salts" in this respect, refers to the relatively non-toxic, inorganic and organic acid addition salts of compounds of the present disclosure. These salts can be prepared in situ during the final isolation and purification of the compounds of the disclosure, or by separately reacting a purified compound of the disclosure in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, for example, Berge et al. (1977) "Pharmaceutical Salts", *J. Pharm. Sci.* 66:1-19).

In other cases, the compounds of the present disclosure may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of the compound of the present disclosure (e.g., a compound of Formula (I) or Formula (II)). These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The pharmaceutically acceptable carriers, as well as wetting agents, emulsifiers, lubricants, coloring agents, release agents, coating agents, sweetening, flavoring agents, perfuming agents, preservatives, antioxidants, and other additional components may be present in an amount between about 0.001% and 99% of the composition described herein. For example, said pharmaceutically acceptable carriers, as well as wetting agents, emulsifiers, lubricants, coloring agents, release agents, coating agents, sweetening, flavoring agents, perfuming agents, preservatives, antioxidants, and other additional components may be present from about 0.005%, about 0.01%, about 0.05%, about 0.1%, about 0.25%, about 0.5%, about 0.75%, about 1%, about 1.5%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 85%, about 90%, about 95%, or about 99% of the composition described herein.

Pharmaceutical compositions of the present disclosure may be in a form suitable for oral administration, e.g., a liquid or solid oral dosage form. In some embodiments, the liquid dosage form comprises a suspension, a solution, a linctus, an emulsion, a drink, an elixir, or a syrup. In some embodiments, the solid dosage form comprises a capsule, tablet, powder, dragée, or powder. The pharmaceutical composition may be in unit dosage forms suitable for single administration of precise dosages. Pharmaceutical compositions may comprise, in addition to the compound described herein (e.g., a compound of Formula (I) or Formula (II)) or a pharmaceutically acceptable salt thereof, a pharmaceutically acceptable carrier, and may optionally further comprise one or more pharmaceutically acceptable excipients, such as, for example, stabilizers (e.g., a binder, e.g., polymer, e.g., a precipitation inhibitor, diluents, binders, and lubricants.

In some embodiments, the composition described herein comprises a liquid dosage form for oral administration, e.g., a solution or suspension. In other embodiments, the composition described herein comprises a solid dosage form for oral administration capable of being directly compressed into a tablet. In addition, said tablet may include other medicinal or pharmaceutical agents, carriers, and or adjuvants. Exemplary pharmaceutical compositions include compressed tablets (e.g., directly compressed tablets), e.g., comprising a compound of the present disclosure (e.g., a compound of Formula (I) or Formula (II)) or a pharmaceutically acceptable salt thereof.

Formulations of the present disclosure include those suitable for parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about 99 percent of active ingredient, preferably from about 5 percent to about 70 percent, most preferably from about 10 percent to about 30 percent. Pharmaceutical compositions of this disclosure suitable for parenteral administration comprise compounds of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a compound of the present disclosure (e.g., a compound of Formula (I) or Formula (II)), it may be desirable to slow the absorption of the drug from subcutaneous, intraperitoneal, or intramuscular injection. This may be accomplished by the use of a liquid suspension of crystalline or amorphous material having poor water solubility. The rate of absorption of the drug then depends upon its rate of dissolution, which, in turn, may depend upon crystal size and cystalline form. Alternatively, delayed absorption of a parenterally administered form of the compound of the present disclosure is accomplished by dissolving or suspending compound in an oil vehicle.

In some embodiments, it may be advantageous to administer the compound of the present disclosure (e.g., a compound of Formula (I) or Formula (II)) in a sustained fashion. It will be appreciated that any formulation that provides a sustained absorption profile may be used. In certain embodiments, sustained absorption may be achieved by combining a compound of the present disclosure with other pharmaceutically acceptable ingredients, diluents, or carriers that slow its release properties into systemic circulation.

Routes of Administration

The compounds and compositions used in the methods described herein may be administered to a subject in a variety of forms depending on the selected route of administration, as will be understood by those skilled in the art. Exemplary routes of administration of the compositions used in the methods described herein include topical, enteral, or parenteral applications. Topical applications include but are not limited to epicutaneous, inhalation, enema, eye drops, ear drops, and applications through mucous membranes in the body. Enteral applications include oral administration, rectal administration, vaginal administration, and gastric feeding tubes. Parenteral administration includes intravenous, intraarterial, intracapsular, intraorbital, intracardiac, intradermal, transtracheal, subcuticular, intraarticular, subcapsular, subarachnoid, intraspinal, epidural, intrastemal, intraperitoneal, subcutaneous, intramuscular, transepithelial, nasal, intrapulmonary, intrathecal, rectal, and topical modes of administration. Parenteral administration may be by continuous infusion over a selected period of time.

In certain embodiments of the disclosure, a composition described herein comprising a compound of Formula (I) is administered orally.

In certain embodiments of the disclosure, a composition described herein comprising a compound of Formula (II) is administered orally.

In other embodiments of the disclosure, a composition described herein comprising a compound of Formula (I) is administered parenterally (e.g., intraperitoneally).

In other embodiments of the disclosure, a composition described herein comprising a compound of Formula (II) is administered parenterally (e.g., intraperitoneally).

It is recognized that for treatment of solid tumors, direct injection of the compounds into the tumor may also be carried out (e.g., intratumoral administration). In other embodiments of the disclosure, a composition described herein comprising a compound of Formula (I) is administered parenterally (e.g., intraperitoneally). In other embodiments of the disclosure, a composition described herein comprising a compound of Formula (II) is administered parenterally (e.g., intraperitoneally). It is recognized that for treatment of solid tumors, direct injection of the compounds into the tumor may also be carried out (e.g., intratumoral administration).

For intravenous, intraperitoneal, or intrathecal delivery or direct injection (e.g., intratumoral), the composition must be sterile and fluid to the extent that the composition is deliverable by syringe. In addition to water, the carrier can be an isotonic buffered saline solution, ethanol, polyol (for example, glycerol, propylene glycol, and liquid polyethylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

The choice of the route of administration will depend on whether a local or systemic effect is to be achieved. For example, for local effects, the composition can be formulated for topical administration and applied directly where its action is desired. For systemic, long term effects, the composition can be formulated for enteral administration and given via the digestive tract. For systemic, immediate and/or short term effects, the composition can be formulated for parenteral administration and given by routes other than through the digestive tract.

Dosages

The compositions of the present disclosure are formulated into acceptable dosage forms by conventional methods known to those of skill in the art. Actual dosage levels of the active ingredients in the compositions of the present disclosure (e.g., a compound of Formula (I)) may be varied so as to obtain an amount of the active ingredient which is effective to achieve the desired therapeutic response for a particular subject, composition, and mode of administration, without being toxic to the subject. The selected dosage level will depend upon a variety of pharmacokinetic factors including the activity of the particular compositions of the present disclosure employed, the route of administration, the time of administration, the rate of absorption of the particular agent being employed, the duration of the treatment, other drugs, substances, and/or materials used in combination with the particular compositions employed, the age, sex, weight, condition, general health and prior medical history of the subject being treated, and like factors well known in the medical arts. A physician or veterinarian having ordinary skill in the art can readily determine and prescribe the effective amount of the composition required. For example, the physician or veterinarian can start doses of the substances of the disclosure employed in the composition at levels lower than that required in order to achieve the desired therapeutic effect and gradually increase the dosage until the desired effect is achieved. In general, a suitable daily dose of a composition of the disclosure will be that amount of the substance which is the lowest dose effective to produce a therapeutic effect. Such an effective dose will generally depend upon the factors described above. Preferably, the effective daily dose of a therapeutic composition may be administered as two, three, four, five, six or more sub-doses administered separately at appropriate intervals throughout the day, optionally, in unit dosage forms.

Preferred therapeutic dosage levels are between about 0.1 mg/kg to about 1000 mg/kg (e.g., about 0.2 mg/kg, 0.5 mg/kg, 1.0 mg/kg, 1.5 mg/kg, 2 mg/kg, 3 mg/kg, 4 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, 600 mg/kg, 700 mg/kg, 800 mg/kg, 900 mg/kg, or 1000 mg/kg) of the composition per day administered (e.g., orally or intraperitoneally) to a subject afflicted with the disorders described herein (e.g., HBV infection). Preferred prophylactic dosage levels are between about 0.1 mg/kg to about 1000 mg/kg (e.g., about 0.2 mg/kg, 0.5 mg/kg, 1.0 mg/kg, 1.5 mg/kg, 2 mg/kg, 3 mg/kg, 4 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, 600 mg/kg, 700 mg/kg, 800 mg/kg, 900 mg/kg, or 1000 mg/kg) of the composition per day administered (e.g., orally or intraperitoneally) to a subject. The dose may also be titrated (e.g., the dose may be escalated gradually until signs of toxicity appear, such as headache, diarrhea, or nausea).

The frequency of treatment may also vary. The subject can be treated one or more times per day (e.g., once, twice, three, four or more times) or every so-many hours (e.g., about every 2, 4, 6, 8, 12, or 24 hours). The composition can be administered 1 or 2 times per 24 hours. The time course of treatment may be of varying duration, e.g., for two, three, four, five, six, seven, eight, nine, ten, or more days, two weeks, 1 month, 2 months, 4 months, 6 months, 8 months, 10 months, or more than one year. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

Patient Selection and Monitoring

The methods of the present disclosure described herein entail administration of a compound of Formula (I), Formula (II) or a pharmaceutically acceptable salt thereof to a subject to activate the PRR for IFNs, ISGs and cytokines production or additionally induce the expression of PRRs (e.g., RIG-I, STING). In some embodiments, the subject is suffering from or is diagnosed with a condition, e.g., a proliferative disease, e.g., cancer. Accordingly, a patient and/or subject can be selected for treatment using a compound of Formula (I), Formula (II) or a pharmaceutically acceptable salt thereof by first evaluating the patient and/or subject to determine whether the subject is infected with a proliferative disease, e.g., cancer. A subject can be evaluated as infected with a proliferative disease (e.g., cancer) using methods known in the art. The subject can also be monitored, for example, subsequent to administration of a compound described herein (e.g., a compound of Formula (I), Formula (II) or a pharmaceutically acceptable salt thereof.

In some embodiments, the subject is a mammal. In some embodiments, the subject is a human. In some embodiments, the subject is an adult. In some embodiments, the subject has a proliferative disease, e.g., cancer. In some embodiments, the subject has a cancer of the of the breast, bone, brain, cervix, colon, gastrointestinal tract, eye, gall bladder, lymph nodes, blood, lung, liver, skin, mouth, prostate, ovary, penis, pancreas, uterus, testicles, stomach, thymus, thyroid, or other part of the body. In some embodiments, the subject has a cancer comprising a solid tumor (e.g., a carcinoma, a sarcoma, or a lymphoma). In some embodiments, the subject has a hepatocellular carcinoma or other cancer of the liver. In some embodiments, the subject has a leukemia or other cancer of the blood. In some embodiments, the subject has a breast cancer, renal cell carcinoma, colon cancer, melanoma, ovarian cancer, head and neck squamous cell carcinoma, pancreatic cancer, prostate cancer, lung cancer, brain cancer, or gastrointestinal stromal cancer. In some embodiments, the subject has cancer cells (e.g., tumor cells) comprising specific cancer-associated antigens that induce a T-cell response.

In some embodiments, the subject is treatment naïve. In some embodiments, the subject has been previously treated for a proliferative disease (e.g., a cancer). In some embodiments, the subject has relapsed.

Combination Therapies

A compound described herein may be used in combination with other known therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments, of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A compound described herein and the at least one additional therapeutic agent can be administered simultaneously, in the same or in separate compositions, or sequentially. For sequential administration, the compound described herein can be administered first, and the additional agent can be administered second, or the order of administration can be reversed.

In some embodiments, the combination of a compound of Formula (I) or a pharmaceutically acceptable salt thereof and the additional agent has a synergistic or additive effect.

In some embodiments, the combination of a compound of Formula (II) or a pharmaceutically acceptable salt thereof and the additional agent has a synergistic or additive effect.

In some embodiments, the term "additive" refers to an outcome wherein when two agents are used in combination, the combination of the agents acts in a manner equal to but not greater than the sum of the individual activity of each agent. In some embodiments, the terms "synergy" or "synergistic" refer to an outcome wherein when two agents are used in combination, the combination of the agents acts so as to require a lower concentration of each individual agent than the concentration required to be efficacious in the absence of the other agent. In some embodiments, a synergistic effect results in a reduced in a reduced minimum inhibitory concentration of one or both agents, such that the effect is greater than the sum of the effects. A synergistic effect is greater than an additive effect. In some embodiments, the agents in the composition herein may exhibit a synergistic effect, wherein the activity at a particular concentration is greater than at least about 1.25, 1.5, 1.75, 2, 2.5, 3, 4, 5, 10, 12, 15, 20, 25, 50, or 100 times the activity of either agent alone.

For example, any of the methods described herein may further comprise the administration of a therapeutically effective amount of an additional agent. Exemplary additional pharmaceutical agents include, but are not limited to, anti-proliferative agents, anti-cancer agents, anti-diabetic agents, anti-inflammatory agents, immunosuppressant agents, and a pain-relieving agent Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In some embodiments, the additional agent is an anti-cancer agent, e.g., an alkylating agent (e.g., cyclophosphamide).

In an embodiment, the additional agent is an immunooncology agent, for example, an agent that activate the immune system, e.g., making it able to recognize cancer cells and destroy them. Exemplary immonooncology compounds are compounds that inhibit the immune checkpoint blockade pathway. In an embodiment, the compound is an antibody such as a PD-1 or PD-L1 antibody or a co-stimulatory antibody. In some embodiments, the compound is an anti-CTLA4 antibody. In another embodiment, the agent is a cell based agent such as CAR-t therapy.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Abbreviations used in the following examples and elsewhere herein are:
3H-BD Iyer-Beaucage reagent
Ac Acetyl
DCA dichloroacetic acid
DCC N,N'-dicyclohexylcarbodiimide
DCM dichloromethane
DMAP 4-dimethylaminopyridine
DMT Dimethoxytrityl
EtOAc Ethyl acetate
ETT 5-(ethylthio)-1H-tetrazole
h hours
IPA isopropyl alcohol
LCMS liquid chromatography-mass spectrometry
MeOH methanol
MSNT 1-Mesitylene-2-sulfonyl-3-nitro-1,2,4-triazole
PTSA p-Toluenesulfonic acid
Py Pyridine
r.t. room temperature
TBHP Tert-butyl hydroperoxide
TEA Triethylamine
THF tetrahydrofuran
TLC thin-layer chromatography Example 1. Synthesis of Exemplary Compounds of the Disclosure Procedure for Synthesis of Cyclic Dinucleotide Prodrugs 9 and 4, and Cyclic Thio-Diphosphates

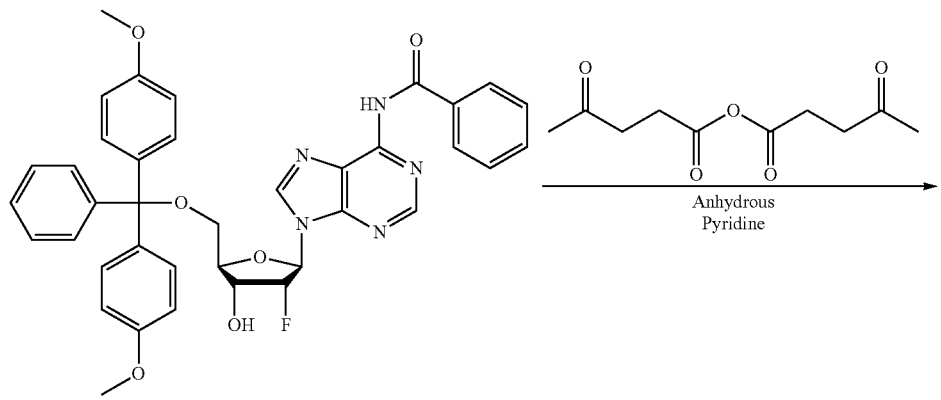

115 116
-continued
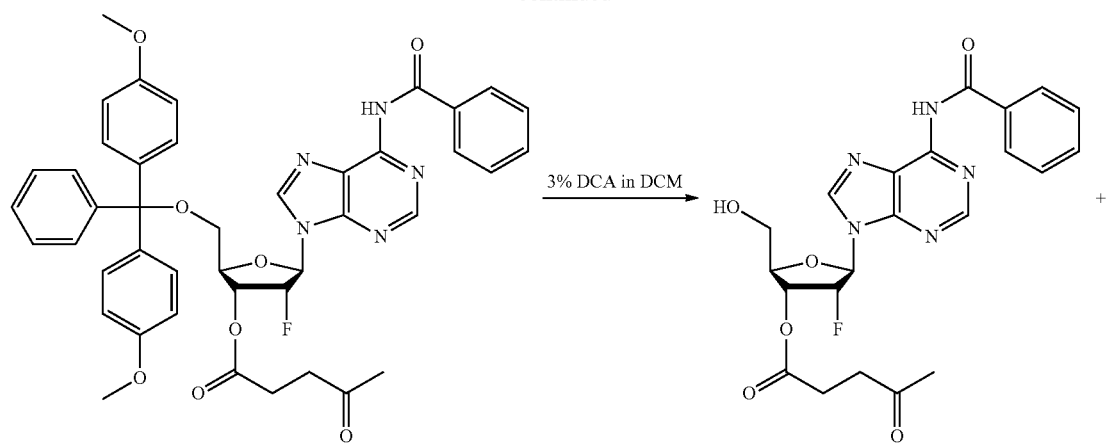
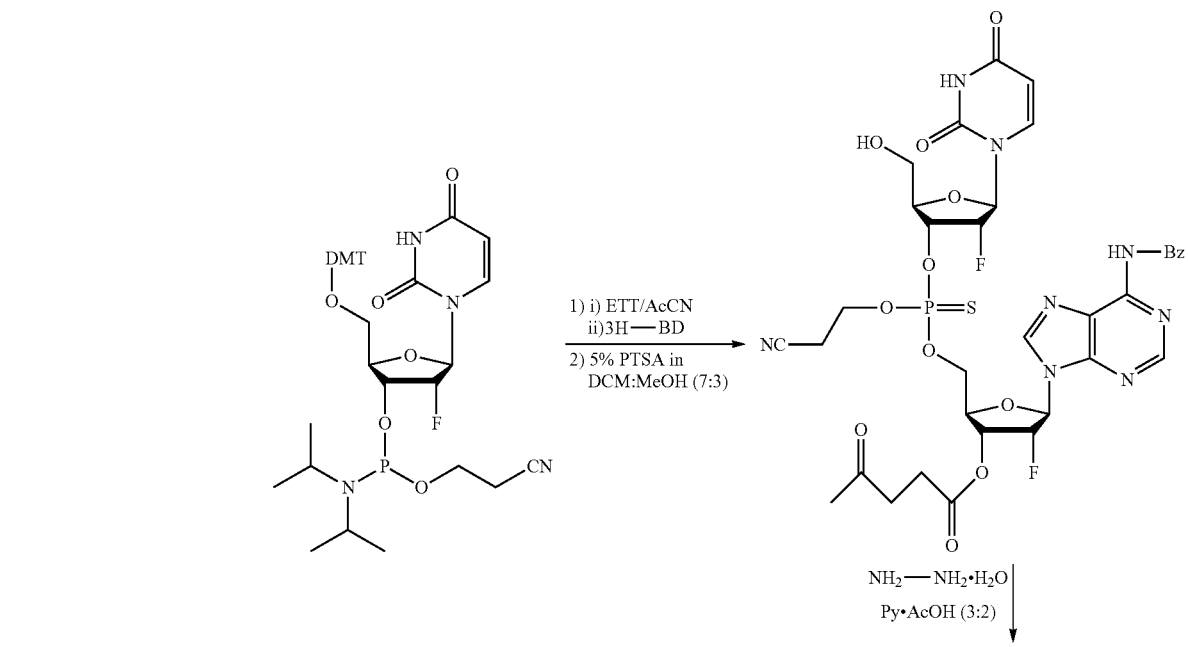
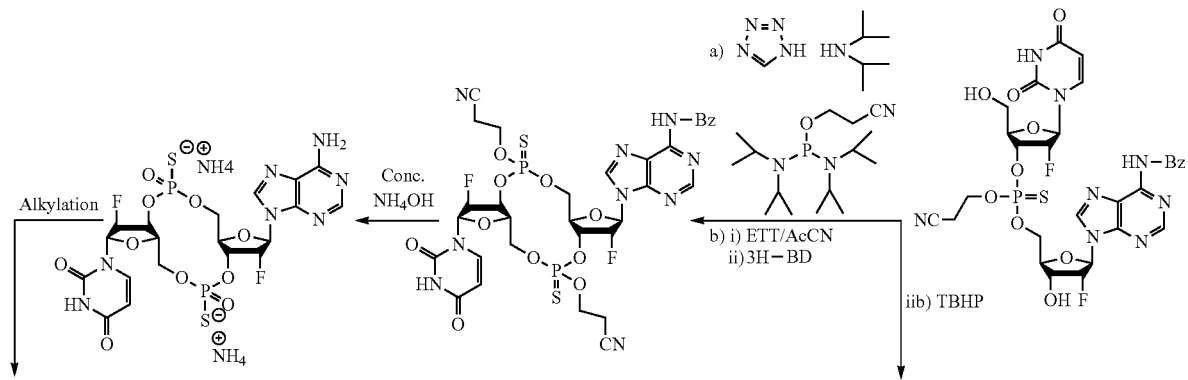

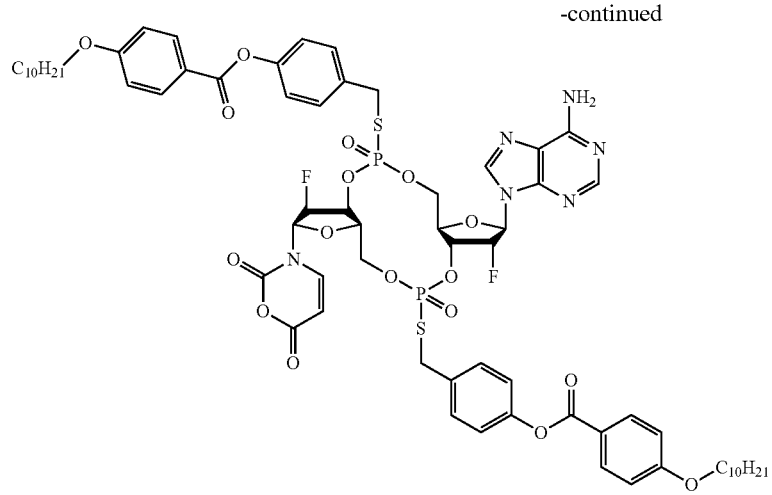

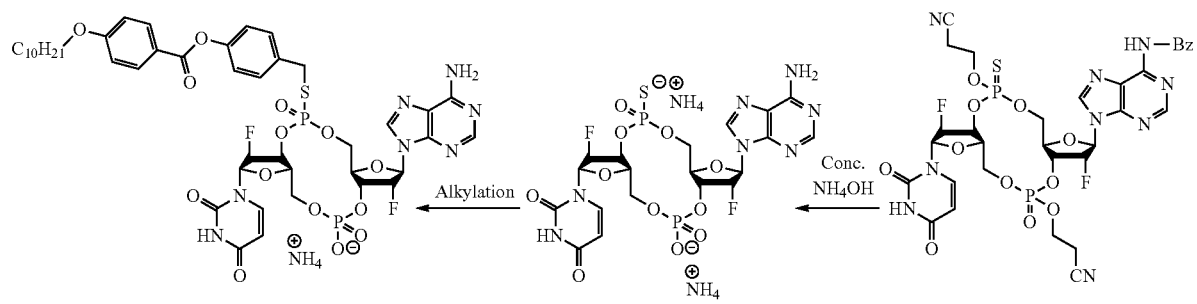

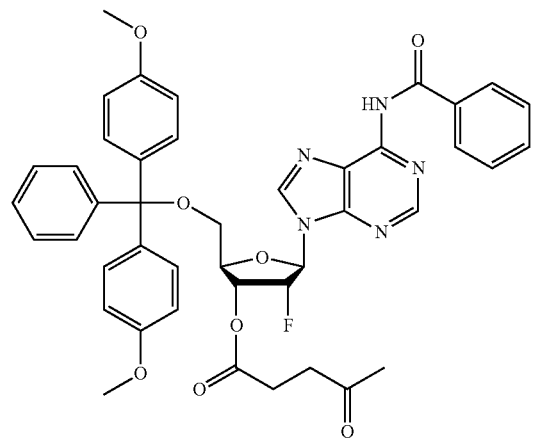

Synthesis of 5'-OH-3'-Levulinyl-2'F-dA:

Levulinic acid (2.148 g, 18.5 mmol) was dissolved in dry-dioxane (50 mL) and the solution was cooled to 5-10° C. on an ice-water bath. DCC (1.939 g, 9.4 mmol) was added portion wise over 1 h. The ice-water bath was removed and the reaction was allowed to warm to room temperature over 2 hours. The resulting dicyclohexyl urea precipitate was filtered off, and washed with dry-dioxane (10 mL). The filtrate was added to a solution of 5'DMT-2'F-3'OH-dA (5.0 g, 7.4 mmol) in dry pyridine (50 mL) and a catalytic amount of DMAP then was added under atmosphere of argon. After stirring for 2 hours at room temperature, the mixture was evaporated to dryness. The residue was dissolved in DCM (150 mL) and the organic phase was washed with 5% NaHCO$_3$ (100 mL) and brine (100 mL), dried over Na$_2$SO$_4$ and concentrated under reduced pressure to provide the desired product as a white solid.

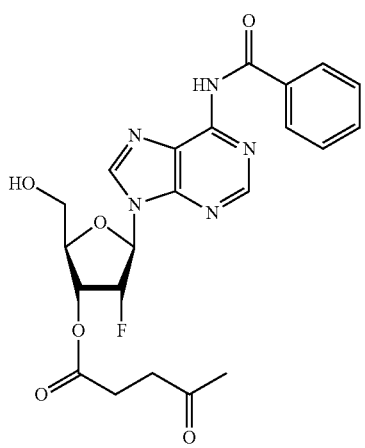

Detritylation:

Above solid was dissolved in DCM (100 mL), and water (1.33 mL, 74 mmol) was added to reaction mixture. 6% DCA in DCM (100 mL) was then added and the reaction mixture was stirred at room temperature for 10-15 min. The resulting mixture was quenched by the addition of methanol (25 mL) and then washed with 5% NaHCO₃ solution (150 mL) and brine (150 mL). The combined organic layers were dried over Na₂SO₄ and concentrated under reduced pressure. The crude residue was purified using combi-flash silicagel column chromatography eluting with 0-5% MeOH in DCM to give 3.45 g (62%0 yield) of pure desired product as a white solid.

atmosphere of argon. The resulting mixture was stirred at room temperature under argon for 2 h. Once TLC analysis showed reaction completion, water was added (80 µL, 2 equivalents to amidite).

Sulfurization:

In a silanized flask, Beaucage reagent (3H-BD) (592 mg, 2.96 mmol) was dissolved in acetonitrile (5.0 mL). The above coupling reaction mixture was transferred to solution of sulfurizing reagent (3H-BD) in acetonitrile and under an atmosphere of argon. The resulting mixture was stirred at room temperature for 45 min. to complete the sulfurization reaction. Methanol (10 mL) was added and the reaction mixture was then stirred for 30 min. The resulting mixture was evaporated under reduced pressure to dryness. The crude residue was dissolved in DCM (100 mL) and washed with water (75 mL). DCM layer was separated, dried over Na₂SO₄ and used for in the detritylation step.

Detritylation:

The above obtained DCM layer containing the sulfurization product was cooled in an ice-water bath. 5% PTSA solution in DCM:MeOH (7:3, 100 mL) was added and the reaction mixture was stirred for 15 min. to complete the detritylation reaction. Water (50 mL) was then added and the resulting mixture was stirred for another 15 minutes. The reaction mixture was transferred to separator funnel and the water was layer was separated. The organic layer was washed 5% NaHCO₃ solution (100 mL), pH of the aqueous layer is above 7.0. The combined organic layers were dried over Na₂SO₄ and concentrated under reduced pressure to give the crude product. The crude product was purified using combiflash silicagel column chromatography eluting with 0-5% MeOH in DCM to give 960 mg of pure desired product as a white solid.

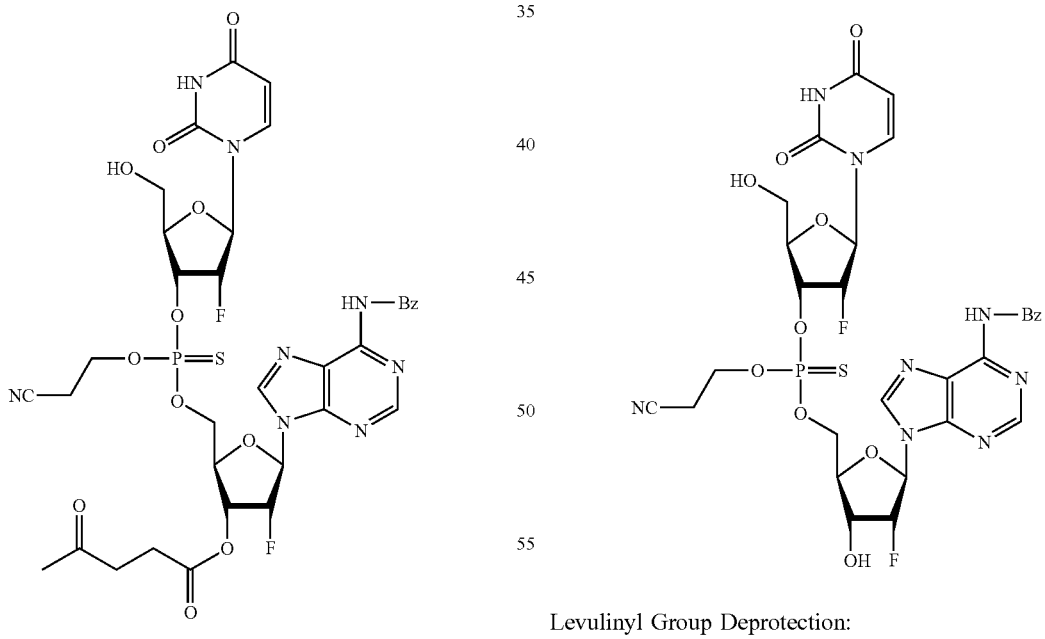

Coupling:

5'OH-3'-Levulinylated-2'F-deoxy-Adinosine (700 mg, 1.48 mmol) and 5'DMT-2'F-3'CED-Phosphoamidite-deoxy-Uridine (1.66 g, 2.22 mmol) mixture was dried under high vacuum for 1-2 hours. Argon was flushed over the round bottom flask containing reaction mixture. Anhydrous acetonitrile (40 mL) was added to reaction mixture Followed by ETT (279 mg, 2.146 mmol) in acetonitrile (5.0 mL) under Levulinyl Group Deprotection:

3'-Levulinyl protected dinucleotide thiophosphate was treated with 0.5M hydrazine monohydrate in a mixture of pyridine:acetic acid (3:2 and the reaction mixture stirred at room temperature for 15 minutes. Once TLC analysis showed reaction completion, 2,4-pentanedione (2.0, mL) was then added to quench unreacted hydrazine hydrate. The volatiles were removed under reduced pressure and the reaction mixture was partitioned between 25% IPA in DCM (50 mL) and water (50 mL). The organic layers were collected and evaporated to dryness under reduced pressure to give thick liquid, which was co-evaporated with toluene (2×15 mL) to provide crude residue which was purified on Combiflash silicagel column chromatography using 0-10% MeOH in DCM to give 725 mg of pure desired product as a white solid.

Cyclization:

Dinucleotide phosphorothioate trimester (1 equivalent) and 2-cyanoethyl tetra isopropyl phosphorodiamidite (bisamidite) (1 equivalent) were dissolved in a mixture of dry acetonitrile and dry DCM (2:1, 30 mL). Disopropylamino-tetrazolide (1 equivalent) was added to reaction mixture in 4 portions over a period of 1 hour under an inert atmosphere. The solution was stirred for an additional 2 h at r.t. and ETT (2.0 equivalent) was then added to the reaction mixture was stirred for overnight. Deoxygenated water (29 μL) was then added to reaction mixture.

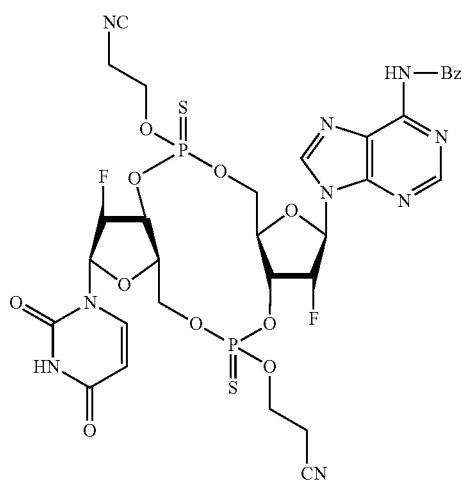

Sulfurization (Synthesis of Protected Cyclic Phosphorothiodiphosphate):

Beaucage reagent (3H-BD) (2.0 equivalent) was dissolved in acetonitrile in a silanized flask. One portion of above cyclization product (two thirds) was added to sulfurizing reagent under an atmosphere of argon. and the reaction mixture was stirred at room temperature for 45 minutes. Methanol (10 mL) was then added and the resulting mixture was stirred for 30 minutes. Solvents were evaporated under reduced pressure and the crude residue was dissolved in DCM (50 mL) and washed with water (50 mL). The DCM layers were separated, dried over Na$_2$SO$_4$ and concentrated under reduced pressure. The crude product was purified using Combiflash silica gel column chromatography eluting with 0-10% MeOH in DCM to give 150 mg of pure desired product.

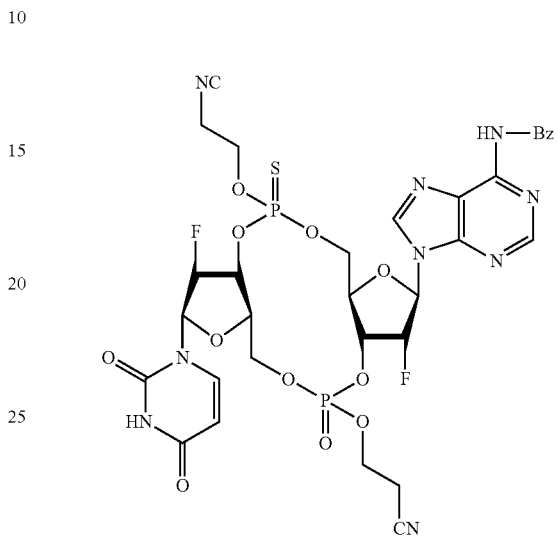

Oxidation (Synthesis of Protected Cyclic Phosphoromonothio Diphosphate):

TBHP (4.0 equivalent) was added to a stirred solution of a second portion of cyclization product (one third) at 0° C. and reaction mixture was warmed to r.t. over 15 minutes. Excess TBHP was quenched by addition of a saturated sodium bisulfite solution and the resulting mixture was evaporated under reduced pressure. The crude residue was dissolved in DCM (25 mL) and washed with water (20 mL). Organic layers were separated and dried over Na$_2$SO$_4$ and concentrated under reduced pressure. The resulting crude product was purified using Combiflash silicagel column chromatography eluting with 0-10% MeOH in DCM to give 60 mg of pure desired product.

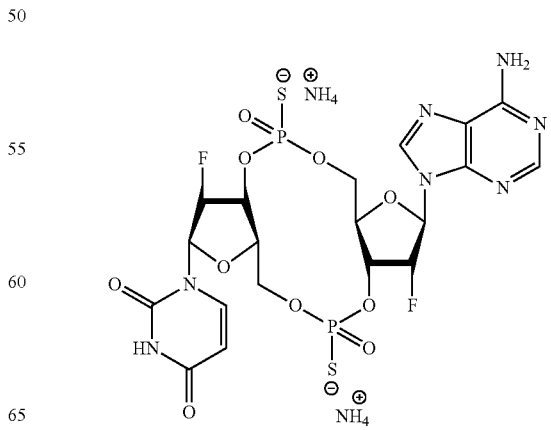

Deprotection of Cyclic Phosphorothiodiphosphate:

Protected cyclic phosphorothiodiphosphate (60 mg) was dissolved in conc. NH$_4$OH (2.0 mL) and stirred at r.t. overnight. Once LCMS showed reaction completion, the mixture was evaporated under reduced pressure to remove ammonia. The water layer was washed with ethyl acetate (5×5 mL), separated and lyophilized to provide 100 mg of crude product as a white fluffy solid.

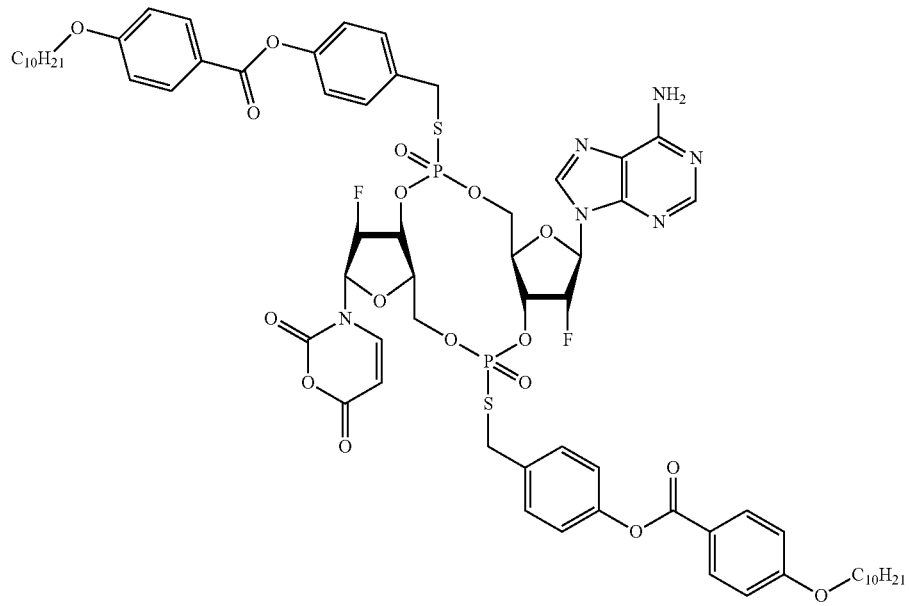

Cmd 4

Alkylation of Cyclic Phosphorothio Diphosphate:

Cyclic phosphorothio diphosphate (25 mg) was dissolved in water (250 µL). A solution of 4-(iodomethyl)phenyl 4-(decyloxy)benzoate (42 mg) in a mixture of THF:Acetone (1:1, 2.0 mL) was then added. Reaction mixture pH was approximately 3.5-4.0. The reaction mixture was stirred at r.t. for 40 hours. The crude product was purified using Combiflash silicagel column chromatography eluting 0-10% IPA in DCM to give 25 mg of the desired product as a yellowish brown solid.

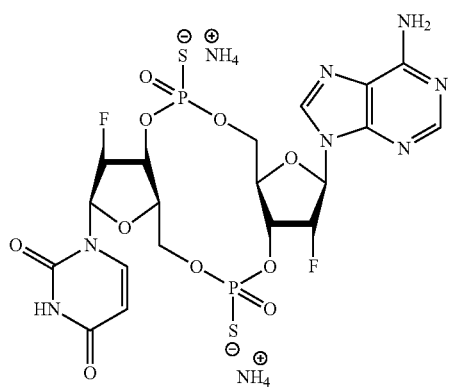

Deprotection of Cyclic Phosphoromonothio Diphosphate:

Protected cyclic phosphoro monothio diphosphate (60 mg) was dissolved in conc. NH$_4$OH (5.0 mL) and then stirred at r.t. for overnight. Once LCMS showed reaction, the mixture was evaporated under reduced pressure to remove ammonia. The water layer was washed with ethyl acetate (5×5 mL), separated and lyophilized to provide 50 mg of the crude desired product as a white fluffy solid.

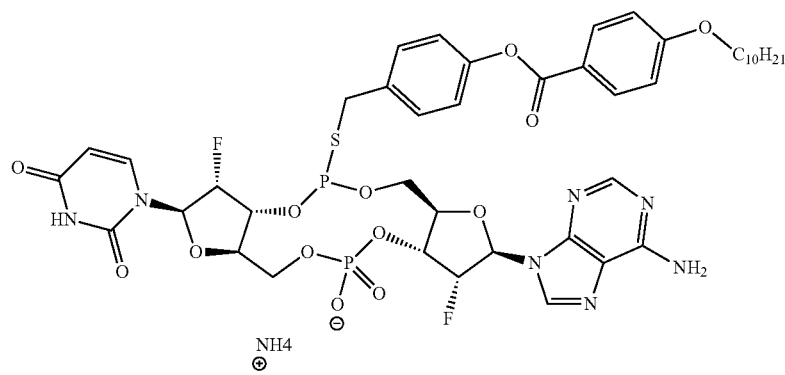

Alkylation of Cyclic Phosphoromonothio Diphosphate:

Cyclic phosphoromonothio diphosphate (20 mg) was dissolved in water (200 μL). A solution of 4-(iodomethyl)phenyl 4-(decyloxy)benzoate (18 mg) in a mixture of THF:Acetone (1:1, 1.4 mL) was then added. The reaction mixture pH was approximately 4.0. The reaction mixture stirred at r.t. overnight and solvents were removed under reduced pressure. The resulting crude residue was redissolved in water:acetonitrile (1:1, 2.0 mL). A precipitate (unreacted alkylating reagent) formed and was removed by centrifugation. The mother liquor was lyophilized and the crude product was purified by using C$_{18}$ sep pack column (Waters, 4.0 g) with 0.2M ammonium acetate buffer. The compound was eluted with acetonitrile:water (1:1). The pure fractions were collected and lyophilized to provide 5-6 mg of pure desired product as a white fluffy solid.

Example 2. Exemplary Synthesis of β-Glucuronide Drug-Linker Unit

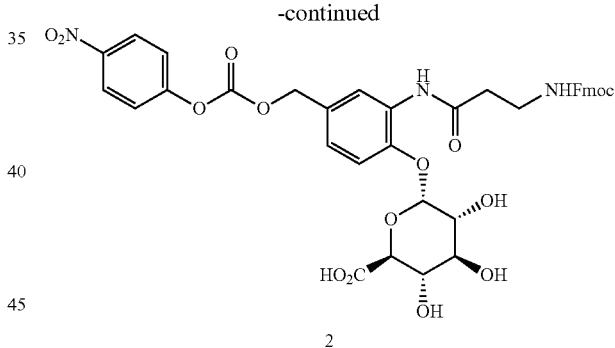

Aryl 3-glucuronide was acylated with acid chloride 1, and then converted to p-nitrophenyl (PNP) carbonate 2 (US 2017/0189542; incorporated by reference).

Example 3. Exemplary Synthesis of Methylene Carbamate Drug-Linker Unit Utilizing the Curtis Rearrangement Reaction

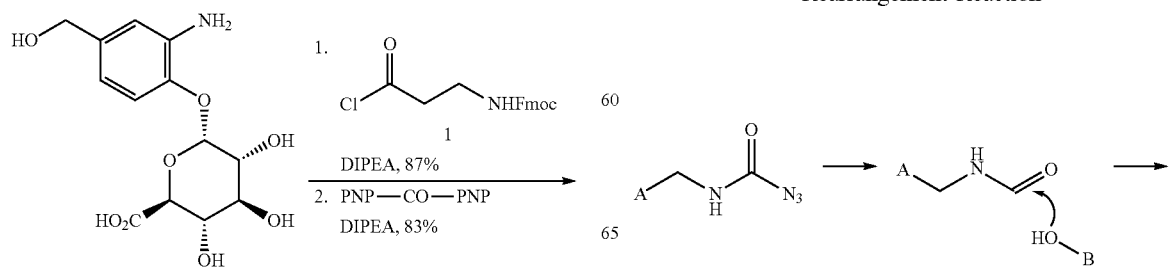

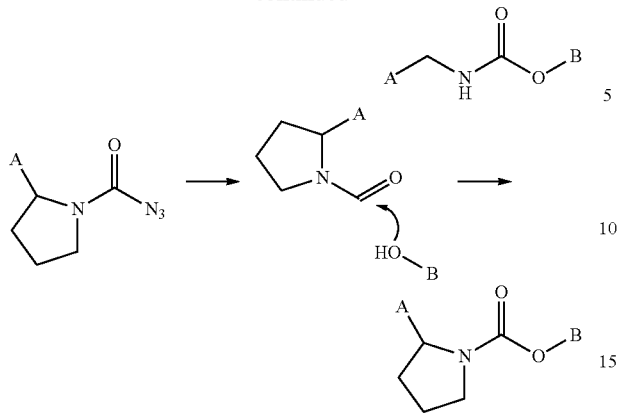

Exemplary synthesis utilizing the Curitus Rearragement reaction for methylene carbamate linkers wherein A represents a connection to the drug unit and B represents a connection to a selfimmolative unit (US 2016/0303254; incorporated by reference).

Example 4

General Procedure

NMR was obtained on a Varian-300 spectrometer, with $^1$H 300 MHz in deuterated DMSO unless otherwise specified. All chemical shifts are referenced to tetramethylsilane. Mass spectra were determined on a PE SCIEX, API 2000 LC-MS spectrometer. Solutions in organic solvents were dried with anhydrous $Na_2SO_4$. Solvents were evaporated under reduced pressure on a Buchi rotary evaporator. TLC was carried out on glass-backed silica gel plates (Merck 60 F254) with visualization of components by UV light (254 nm). Flash column chromatography was performed on silica gel (Merck 230-400 mesh) (US 2010/0273843; incorporated by reference).

Exemplary Synthesis of Heterocylic Self-Immimolative Groups

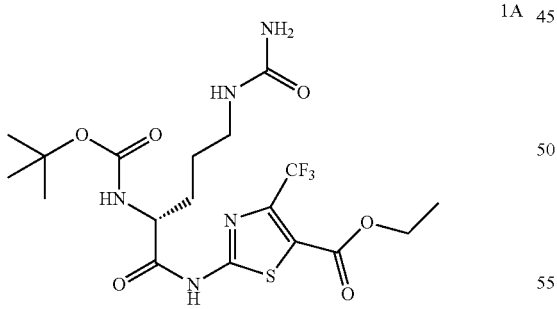

1A 8.6 g of Boc-Citrulline was dissolved in 250 mL of DMF. The solution was added 7.2 mL of DIEA and 6.7 g of CDI. After stirred at r.t. for 30 min, the solution was added 5 g of ethyl-2-amino-4-(trifluoromethyl)-5-thiazolecarboxylate (Matrix Scientific, Columbia S.C. USA). The reaction was quenched after additional 2 hours at r.t. by the addition of 25 mL of water. The mixture was diluted with 250 mL of EtOAc. The organic layer was washed with 1N HCl, brine and worked up as described in General Procedure. Pure title compound 1A was obtained by purification on a fresh silica gel column eluted with 5% MeOH in DCM (5.6 g, yield 54%) (US 2010/0273843; incorporated by reference).

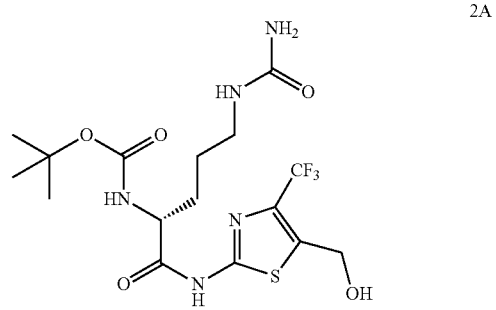 [SMILES: CC(C)(C)OC(=O)N[C@H](CCCNC(N)=O)C(=O)Nc1nc(C(F)(F)F)c(CO)s1]

2A 3 g of 1A was dissolved in 90 mL of THF. The solution was added 12 mL of lithium aluminum hydride (1.0M solution in THF) at 0° C. After stirring at 0° C. for 2 hours, the reaction was quenched by addition of 10 mL of water, diluted with 250 mL of EtOAc and filtered through a celite pad. The organic layer was washed with brine and worked up as described in General Procedure. Pure title compound 2A was obtained by purification on a fresh silica gel column eluted with 5% MeOH in DCM (2.2 grams yield 80%) (US 2010/0273843; incorporated by reference).

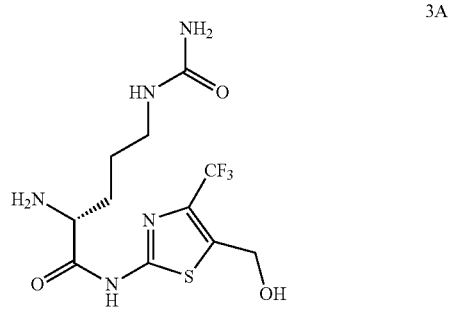 [SMILES: NC(=O)NCCC[C@@H](N)C(=O)Nc1nc(C(F)(F)F)c(CO)s1]

3A

Compound 2A (1.5 g) was dissolved in 45 mL methanol. To the solution was added 8 mL of HCl in dioxane (4.0M). After stirring at room temperature r.t. for 2 hours, the solution was concentrated down at a rotary evaporator under reduced pressure. The crude product was dried under vacuum for additional 18 hours at r.t. and used for next reaction without further purification (US 2010/0273843; incorporated by reference).

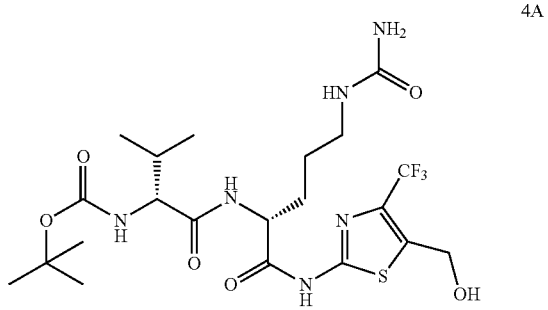 [SMILES: CC(C)[C@@H](NC(=O)OC(C)(C)C)C(=O)N[C@H](CCCNC(N)=O)C(=O)Nc1nc(C(F)(F)F)c(CO)s1]

4A

Compound 3A (1.2 gm), 1.1 grams of Boc-valine, 1.4 mL of DIEA, and 3.3 g of HBTU were dissolved in 36 mL DMF.

After stirring at r.t. for 18 hours, the reaction was quenched by addition of 5 mL of water and diluted with 400 mL of EtOAc. The organic layer was washed with brine and worked up as described in General Procedure. Pure title compound 4A was obtained by purification on a fresh silica gel column eluted with 10% MeOH in DCM (1.4 g, yield 75%) (US 2010/0273843; incorporated by reference).

5A

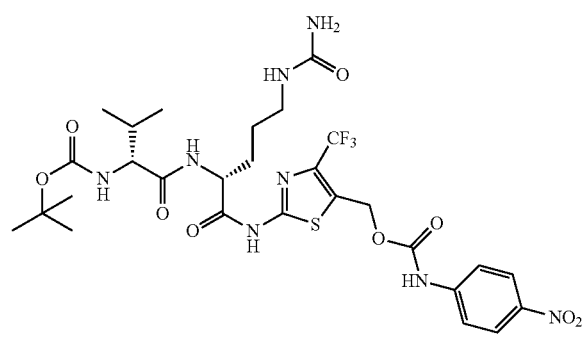

4A (50 mg) was dissolved in 0.5 mL of THF and DCM (1:1). To the solution was added 30 mg of 4-nitrophenyl isocyanate. After stirring at RT for 48 hours, the mixture was directly charged to a silica gel column eluted with 5% MeOH in DCM to give the pure title compound 5A (US 2010/0273843; incorporated by reference).

Example 5. Exemplary Synthesis of Malemide Self Immolative Groups

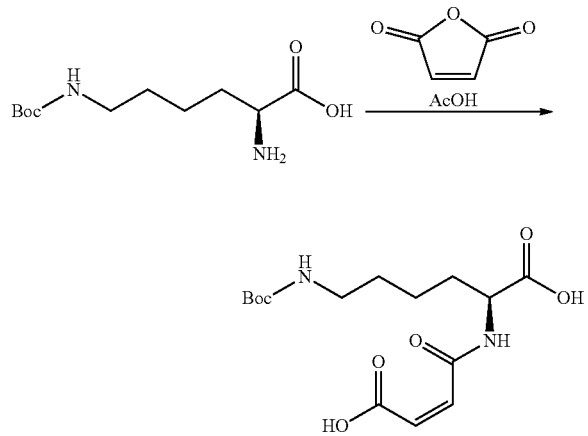

In a 50 mL round bottom flask H-Lys(boc)-OH (246 mg, 1 mmol) and maleic anhydride (98 mg, 1 mmol) were dissolved in 1 mL acetic acid and the solution was stirred at room temperature for 3 hours. The reaction mixture was concentrated to an oil on the rotovap, and the product was precipitated by adding ~10 mL dichloromethane. The precipitate was collected by vacuum filtration, washed with dichloromethane, and dried overnight in the vacuum oven. 270 mg of product was recovered as a white powder (85% yield) (WO 2013/173337; incorporated by reference).

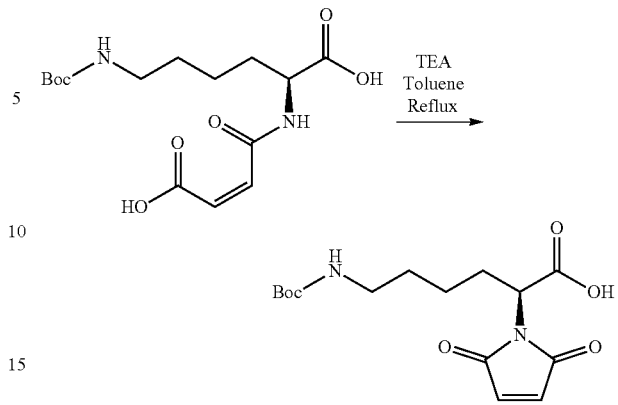

Maleyl-Lys(boc)-OH (100 mg, 0.29 mmol) was suspended in toluene (3 mL) and triethylamine (224 uL) over molecular sieves in a 50 mL round bottom flask equipped with a condenser. D1VIA (~150 uL) was added to aid solubility. The solution was heated to 125° C. and refluxed for 4 hours after which the reaction was shown to be complete by LCMS. The reaction mixture was concentrated to dryness on the rotovap, redissolved in DMSO and purified by preparative HPLC. 56 mg of product was isolated as a white powder (60% yield) (WO 2013/173337; incorporated by reference).

Example 6: Evaluation of Induction of IRF and NF-KB

THP1 dual cells grown in complete media were treated with various concentrations of a compound of the present disclosure or DMSO control. Dual cells carry both secreted embryonic alkaline phosphatase (SEAP) reporter gene under the control of an IFN-β minimal promoter fused to five copies of the NF-kB consensus transcriptional response element to measure NF-kB activity and Lucia reporter gene under the control of an ISG54 minimal promoter to measure IRF activity. After 20 h incubation, IRF activity was assessed using QUANTI-luc to measure levels of Lucia and NF-kB activity was determined by measure SEAP levels at 620-655 nm. % induction was calculated from fold change in luminescence/absorbance compared to DMSO treated sample. Any negative values were given base value 1 for plotting data in log scale for accurate demonstration of dose response. $EC_{50}$ values were generated by curve fit in Xlfit.

Cells grown in complete media were treated with various concentrations of a compound of the disclosure or DMSO control. Dual cells carry both secreted embryonic alkaline phosphatase (SEAP) reporter gene under the control of an IFN-β minimal promoter fused to five copies of the NF-kB consensus transcriptional response element to measure NF-kB activity and Lucia reporter gene under the control of an ISG54 minimal promoter to measure IRF activity. After 20 h incubation, IRF activity was assessed using QUANTI-luc to measure levels of Lucia and NF-kB activity was determined by measure SEAP levels at 620-655 nm. % induction was calculated from fold change in luminescence/absorbance compared to DMSO treated sample. $EC_{50}$ values are generated by curve fit in Xlfit.

Example 7: Exemplary Synthesis of Compounds of the Disclosure

Coupling of Fmoc protected valine as succinimide ester A was coupled with citrulline B in dimethoxyethane and sodium bicarbonate led to dipeptide C. This dipeptide was condensed with 4-aminobenzyl alcohol in the presence of EEDQ in DCM:MeOH (2:1) at r. t. for 36 h resulted in intermediate D. Intermediate D could then be coupled (e.g., via a CDI or phosgene mediated coupling) with STING agonist to yield E.

Synthesis of peptide, linked to a STING agonist could be achieved through the conversion of Fmoc dipeptide intermediate F to the corresponding iodo derivative G. Alkylation of STING agonist with G could yield the peptide linked STING agonist. Subsequent removal of Fmoc group would yield H.

Scheme 1: Exemplary Synthesis of E

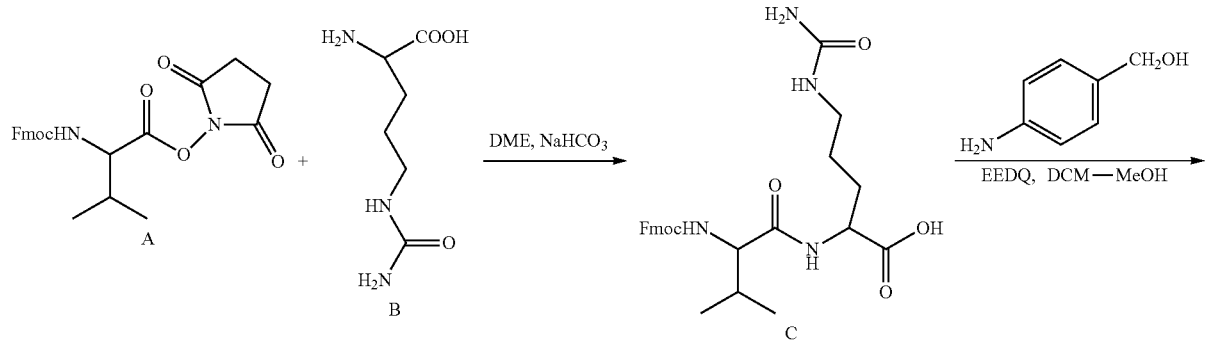

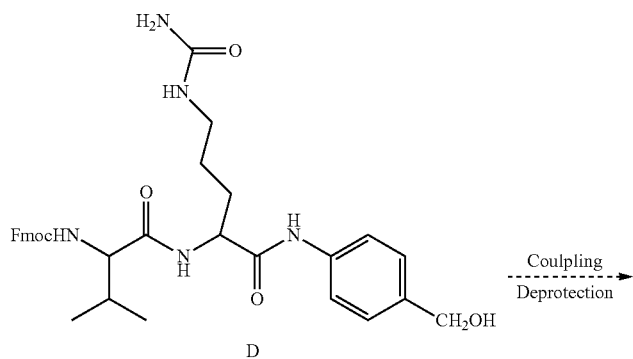

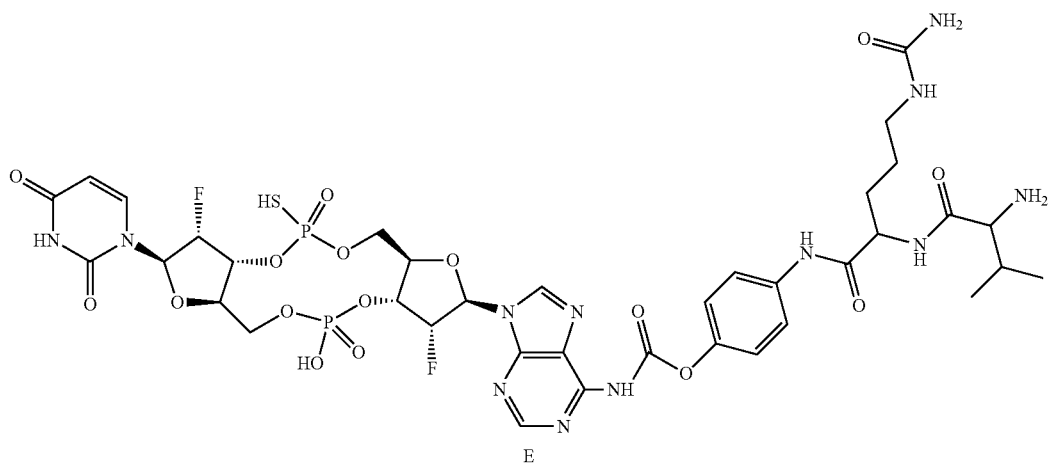

Scheme 2: Preparation of Peptide linked Phosphorothioate

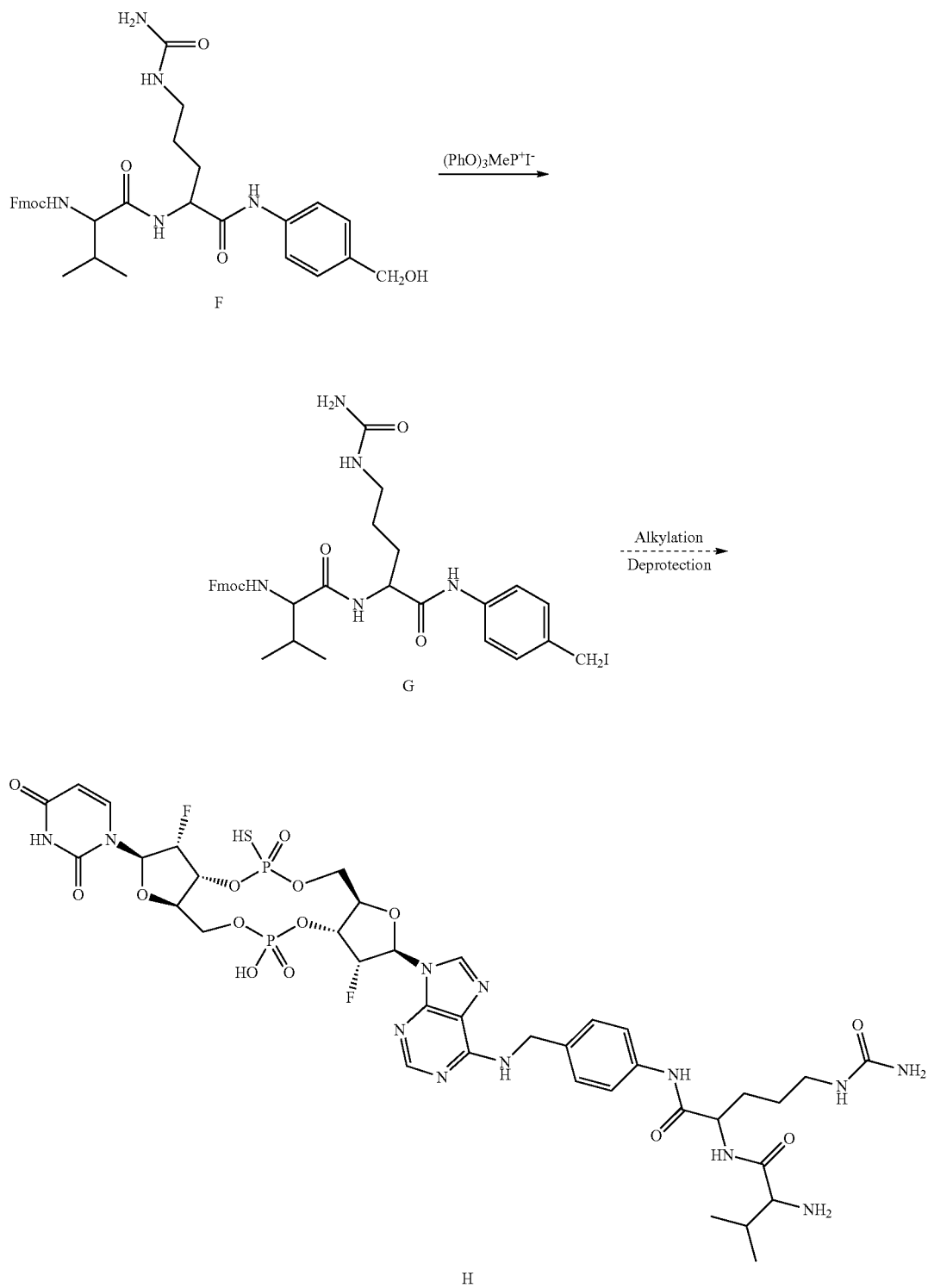

Subsequent removal of Fmoc group from I using diethyl amine in DMF at room temperature afforded dipeptide J, with free amino group. Maleimidocaproic acid as its succimidie ester was coupled with J in DMF at r. t. to yield maleimido derivative K. The terminal benzyl alcohol in K was converted to the benzyl iodide derivative L using phosphonium iodide. This could be used to alkylate a STING agonist give the N-alkylated M.

135 136
Scheme 3: Preparation of Maleimide-Peptide linked Phosphorothioate (Scheme 3)
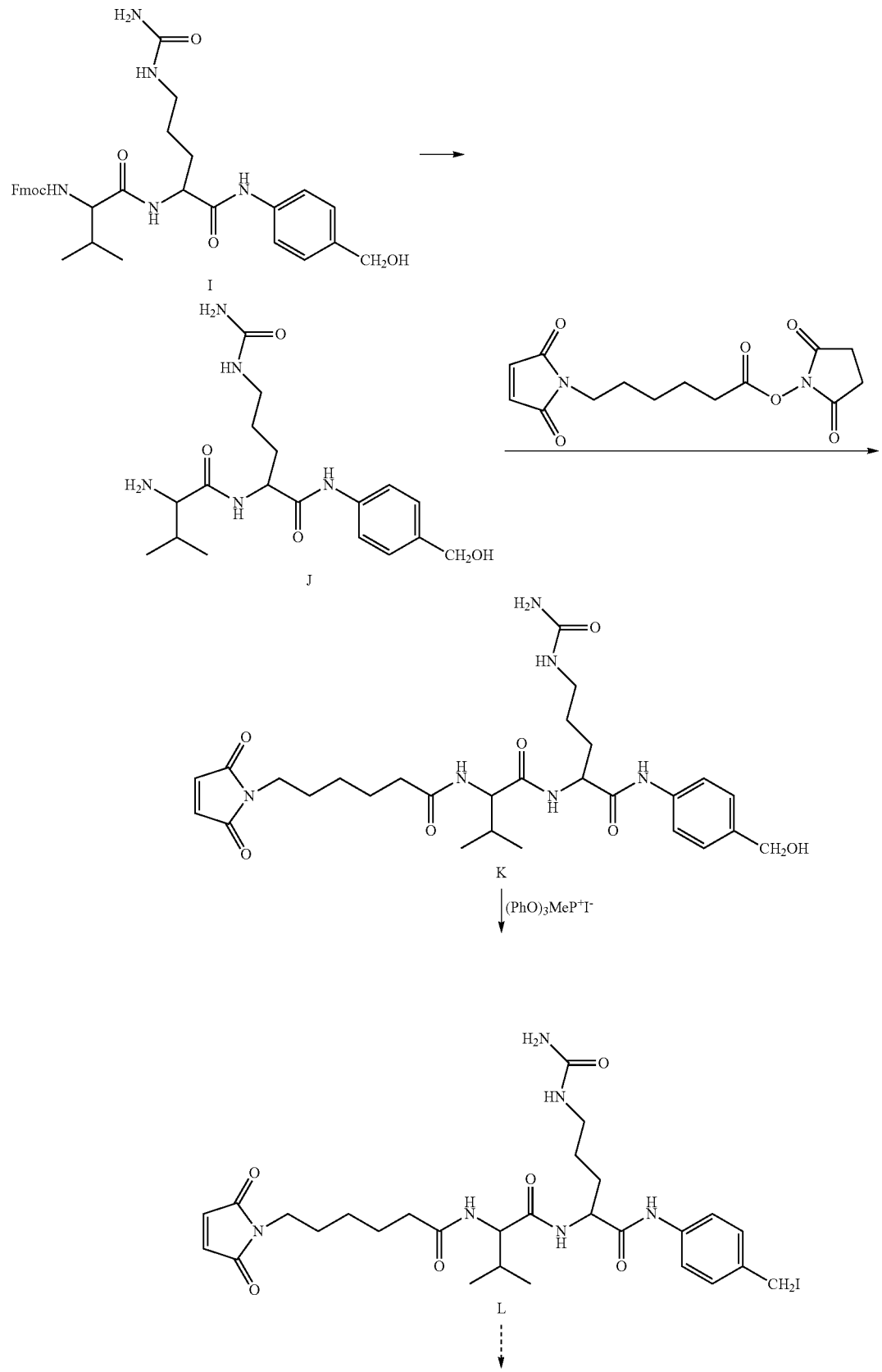

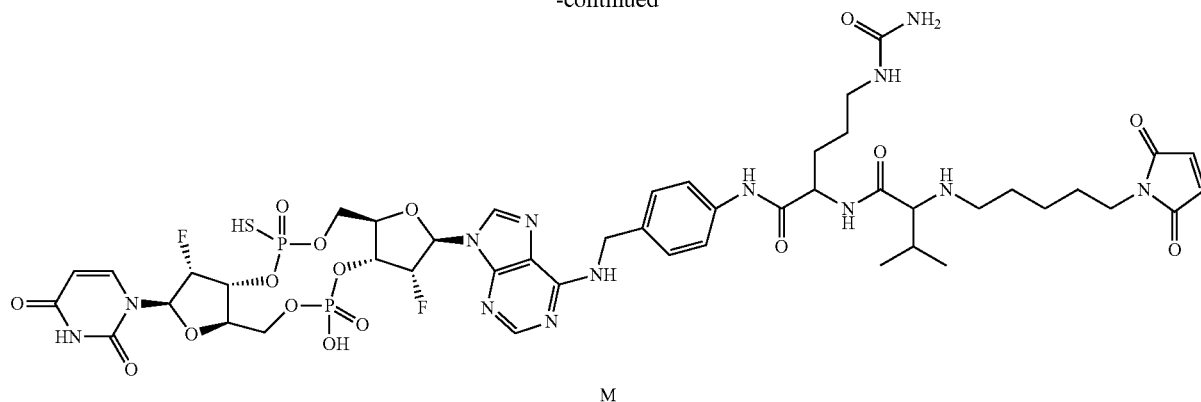
M
Key intermediate O, linking 2-aminoethanol with Fmoc-Val-CitOH N has been prepared. Further subsequent reactions can be carried out to synthesis the compounds illustrated below following protocols similar to those described above with benzyl alcohol derivative.
Scheme 4: Prophetic Synthesis of peptide linked STING agonists Q and S.
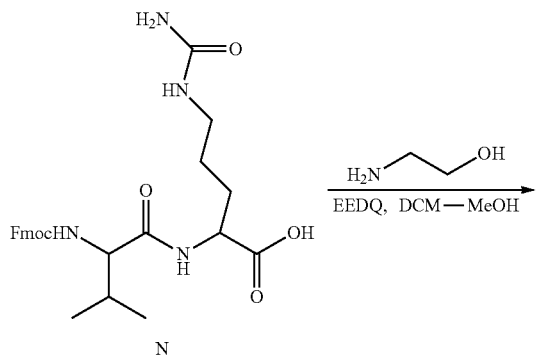
N
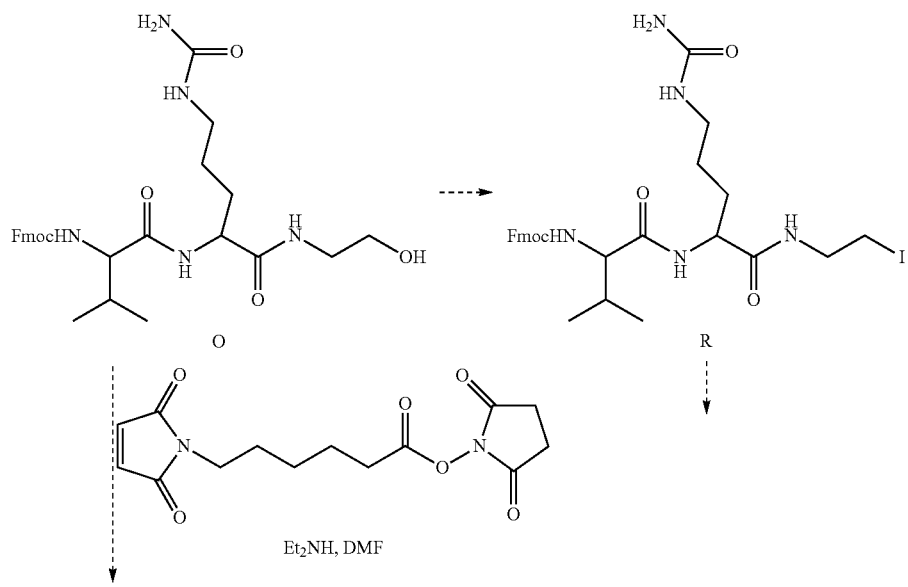

-continued
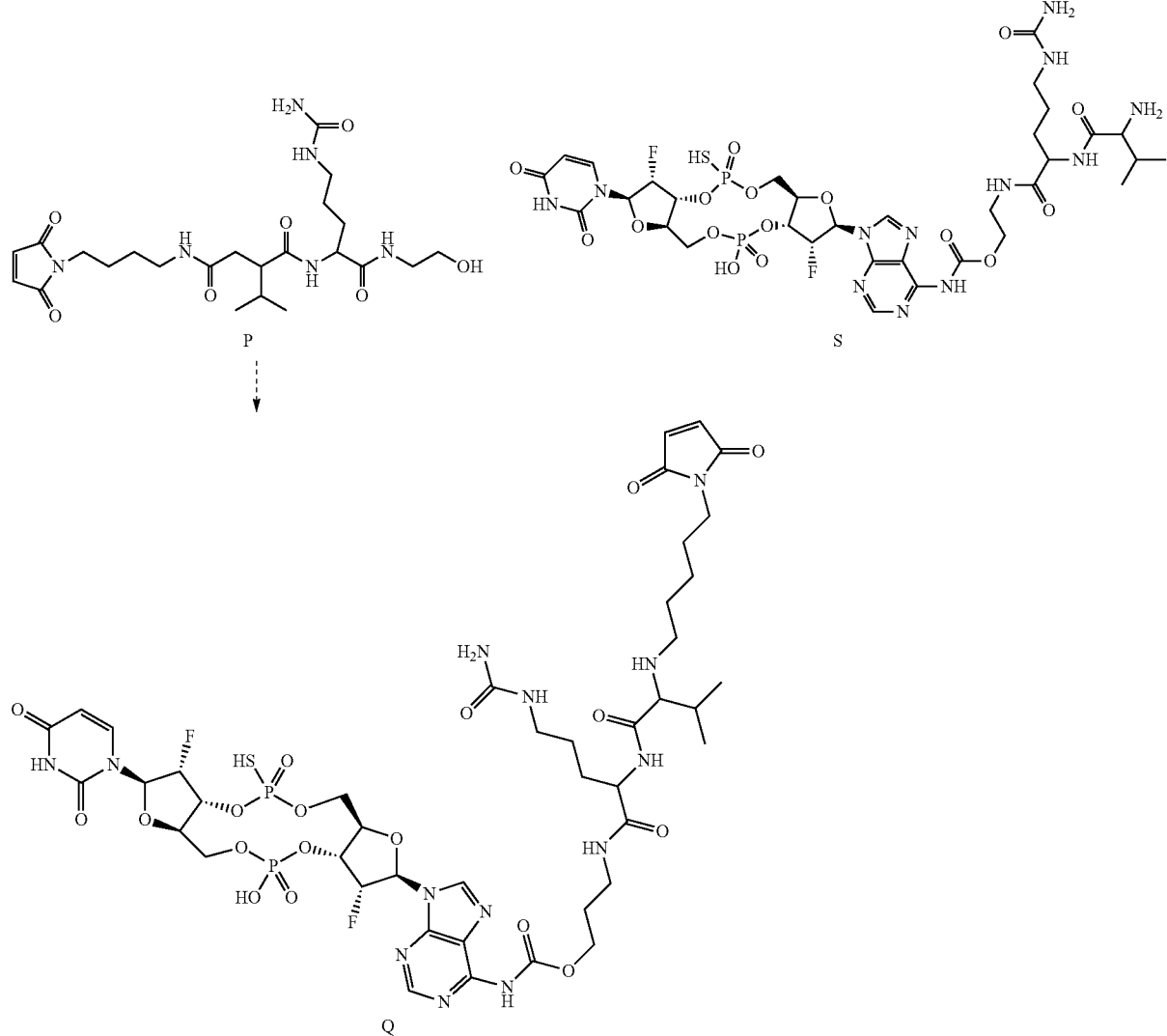
Example 9: Prophetic Synthesis of Peptide-Linked Phosphorothioate Compounds
Prophetic Synthesis of C*
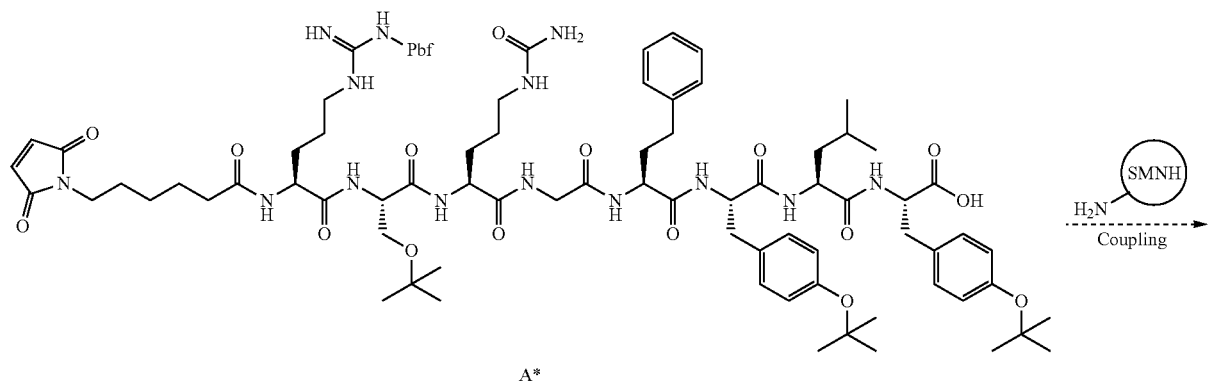

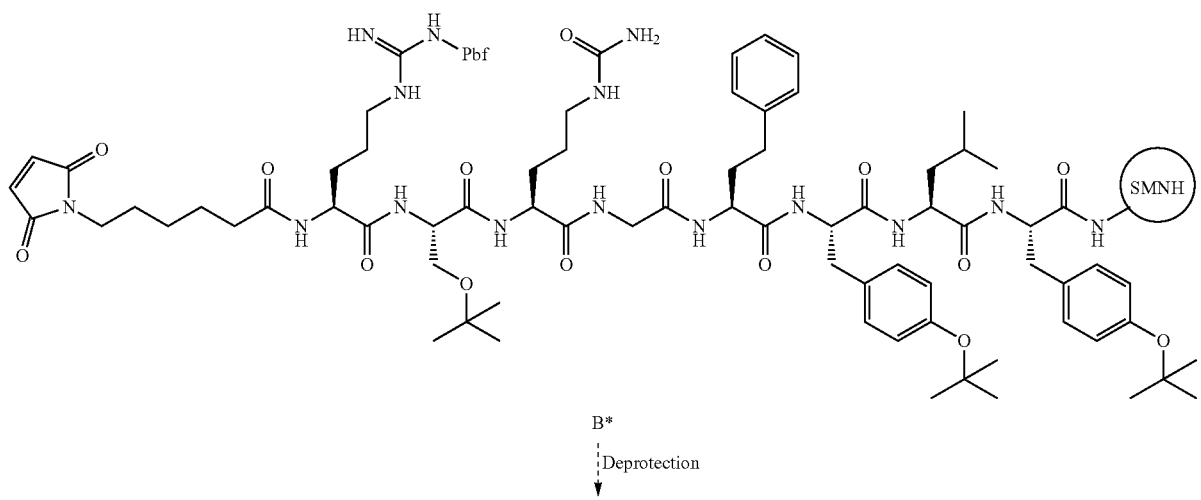
B*
Deprotection
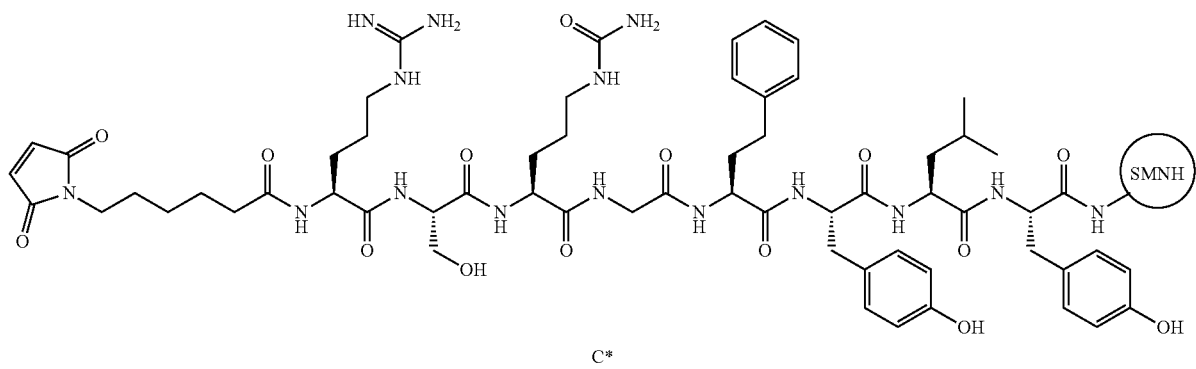
C*
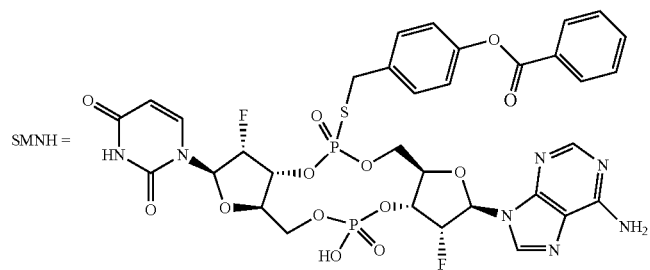

Intermediate A* could be coupled (e.g., via a CDI or phosgene mediated coupling) with STING agonist (SMNH) and then deprotected (e.g., via TFA, TES in H₂O) to yield C*.
Synthesis of G'
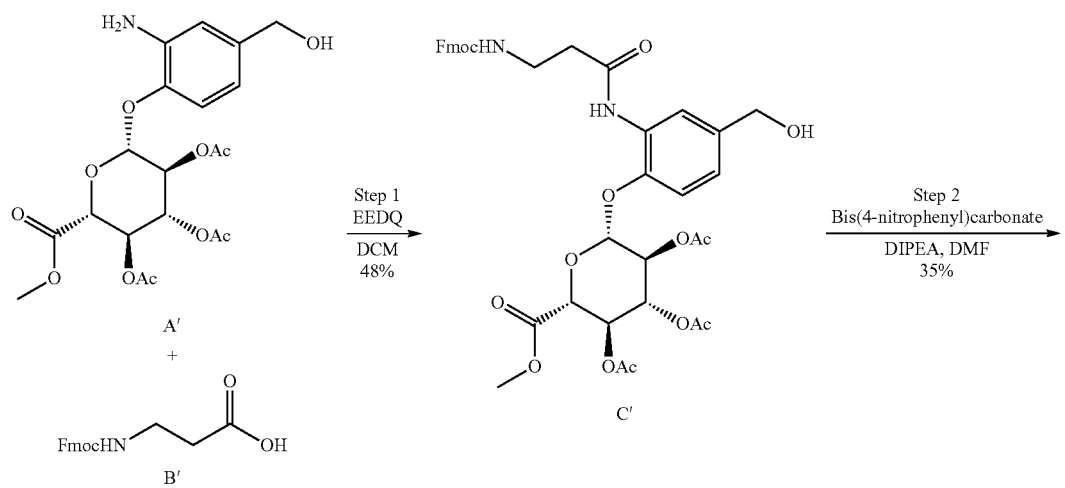
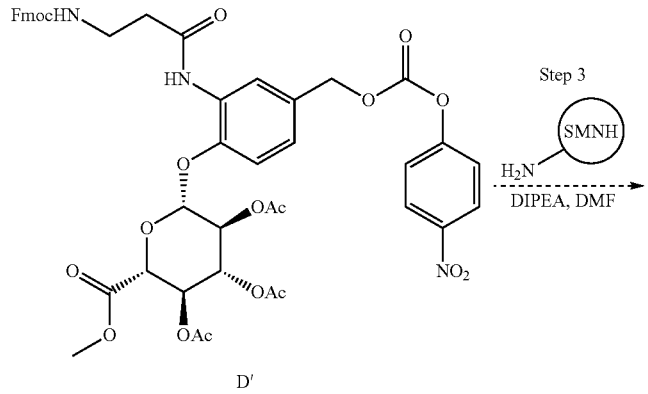
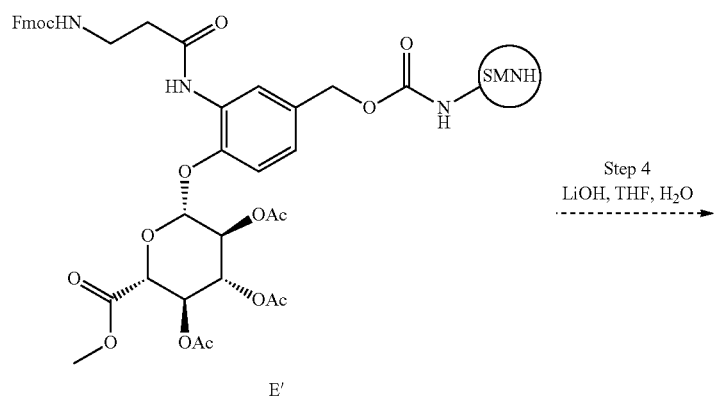

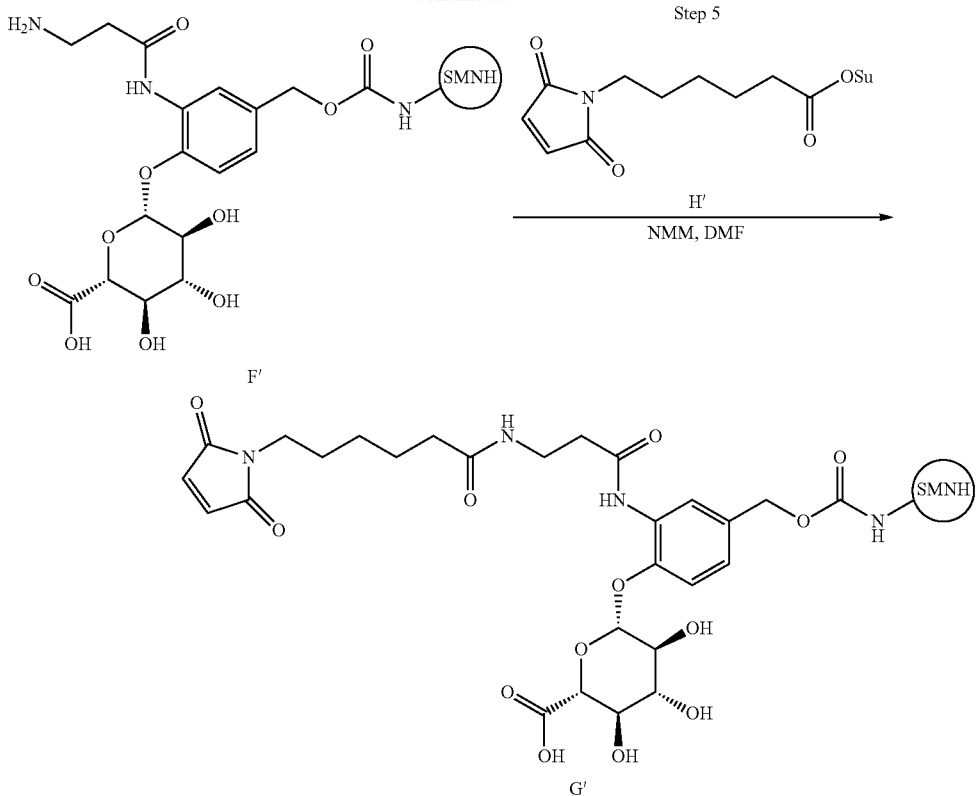

Step 1

To a solution of amine A' (250 mg, 0.5 mmol) in CH$_2$Cl$_2$ (3 mL) was added acid B' (1 eq), EEDQ (1.2 eq). The mixture was stirred at room temperature overnight. Saturated aqueous NaHCO$_3$ (3 mL) was added to the mixture and the organic product extracted with CH$_2$Cl$_2$ (3 mL). The combined organic layers were dried (Na$_2$SO$_4$), filtered through celite and concentrated in vacuo. Purification of the residue on silica gel eluted with MeOH:CH$_2$Cl$_2$: [0 to 100%] provided product C' (200 mg, 48% Yield).

Step 2

To a solution of amide C' (100 mg, 0.13 mmol) in DMF (1 mL) was added DIPEA (1.2 eq). The solution was stirred for 15 min. Then bis(4-nitrophenyl)carbonate (1.5 eq) was added and the mixture was stirred at room temperature for 18 h. Saturated aqueous NaHCO$_3$ (2 mL) was added to the mixture and the organic product extracted with CH$_2$Cl$_2$ (3 mL). The combined organic layers were dried (Na$_2$SO$_4$), filtered through Celite and concentrated in vacuo to provide product D' (39 mg, 32% Yield).

Step 3

Intermediate D' could then be coupled (e.g., via a CDI or phosgene mediated coupling) with a STING agonist to yield E'.

Step 4

The protected compound E' could be taken up in THF (1 mL). LiOH (5 eq) in water (0.5 mL) could then be added and stirred at room temperature for 3 hours. The solvent could then be removed in vacuo and the residue could be neutralized with 1 N HCl. The crude organic product could be extracted with EtOAc (2×5 mL). Combined organic layers could be dried (Na$_2$SO$_4$), concentrated in vacuo to yield acid F'.

Step 5

A solution of F' (2 mg, 0.0013 mmol) and compound H' (N-hydroxysuccinimide (NHS) ester; 1.1 eq) could be taken up in N-methyl morpholine (0.5 mL). Diisopropyl ethylamine (1 eq) could then be added to the reaction mixture and it could be stirred at 60° C. for 4 h. The resulting solution could then be concentrated to afford product G'.

EQUIVALENTS

The disclosures of each and every patent, patent application, and publication cited herein are hereby incorporated by reference in their entirety. While this disclosure has been described with reference to specific aspects, it is apparent that other aspects and variations may be devised by others skilled in the art without departing from the true spirit and scope of the disclosure. The appended claims are intended to be construed to include all such aspects and equivalent variations. Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference.

While this disclosure has been particularly shown and described with references to preferred embodiments thereof, it will be understood by those skilled in the art that various changes in form and details may be made therein without departing from the scope of the disclosure encompassed by the appended claims.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

What is claimed is:

1. A compound of Formula (II):

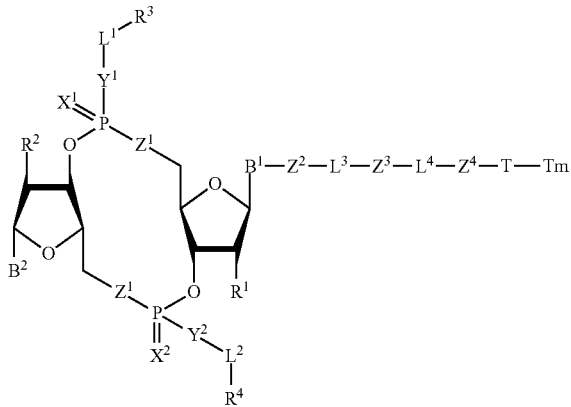

Formula (II)

or a pharmaceutically acceptable salt or stereoisomer thereof, wherein:

Tm is a targeting moiety;

$B^1$ is a purinyl nucleobase and $B^2$ is a pyrimidinyl nucleobase, or $B^1$ is a pyrimidinyl nucleobase and $B^2$ is a purinyl nucleobase;

each of $X^1$ and $X^2$ is independently O or S;

each of $Y^1$ and $Y^2$ is independently O, S, or $N(R^5)$;

each of $Z^1$ is independently O or S;

$Z^2$ is —O—, —N($R^5$)—, —S—, —C(O)—, —C(O)N($R^5$)—, —OC(O)N($R^5$)—, —N($R^5$)C(O)O—, -aryl-, -heteroaryl-, —S(O)—, —S(O)$_2$—, —S(O)N($R^5$)—, —S(O)$_2$N($R^5$)— or —N($R^5$)S(O)—;

$Z^3$ is absent, hydrogen, heterocyclyl, heterocyclyl-$C_1$-$C_{20}$-alkylene-$Q^1$, —OH, —N($R^5$)$_2$, $SR^5$, —CHO, —C(O)N($R^5$)$_2$, —OC(O)N($R^5$)$_2$, —N($R^5$)C(O)O$R^5$, aryl, heteroaryl, —S(O)$R^5$, —S(O)$_2R^5$, —S(O)N($R^5$)$_2$, —S(O)$_2$N($R^5$)$_2$, —N($R^5$)S(O)$R^5$, —OSi($C_1$-$C_4$ alkyl)$^3$, or —C(O)$C_2$-$C_6$ alkenyl;

$Z^4$ is a self-immolative group or absent;

T is absent or a spacer group;

each $L^1$ and $L^2$ is absent, —$C_1$-$C_6$— alkylene or —$C_1$-$C_6$— heteroalkylene, wherein each alkylene and heteroalkyl is optionally substituted with one or more $R^6$;

$L^3$ is oligopeptide-C(O)—, oligiopeptide-aryl-$C_1$-$C_6$-alkylene-, oligiopeptide-aryl-$C_1$-$C_6$-alklyene-C(O)—, oligiopeptide-aryl-$C_1$-$C_6$-heteroalkylene, oligiopeptide-$C_1$-$C_6$-alkylene-C(O)—, oligiopeptide-$C_1$-$C_6$-heteroalkylene-C(O)—, —$C_1$-$C_{40}$— alkylene, —$C_1$-$C_{40}$— heteroalkylene, —$C_1$-$C_{40}$— alkenylene, or —$C_1$-$C_{40}$— alkynylene, wherein the oligopeptide is optionally substituted by one or more $R^{14}$;

$L^4$ is absent or a linker connecting $Z^3$ and $Z^4$;

$Q^1$ is C(O), C(S), or CH$_2$;

each of $R^1$ and $R^2$ is independently hydrogen, halo, —CN, —$C_1$-$C_{20}$ alkyl, or —$OR^7$;

each $R^3$ and $R^4$ is independently hydrogen, —$C_1$-$C_{20}$— alkyl, —$C_1$-$C_{20}$ heteroalkyl, —OC(O)O$C_1$-$C_{20}$ alkyl, cycloalkyl, heterocyclyl, aryl, or heteroaryl, wherein each alkyl, heteroalkyl, cycloalkyl, heterocyclyl, aryl, and heteroaryl is optionally substituted with one or more $R^8$;

$R^5$ is hydrogen or —$C_1$-$C_{20}$ alkyl;

$R^6$ is halo, —CN, —$C_1$-$C_{20}$ alkyl, —$OR^7$, oxo, cycloalkyl, heterocyclyl, aryl, or heteroaryl, wherein each alkyl, cycloalkyl, heterocyclyl, aryl, and heteroaryl is optionally substituted with one or more $R^9$;

$R^7$ is hydrogen, —$C_1$-$C_{20}$ alkyl, cycloalkyl, heterocyclyl, aryl, or heteroaryl, wherein each alkyl, cycloalkyl, heterocyclyl, aryl, and heteroaryl is optionally substituted with one or more $R^9$;

each $R^8$ is independently —$C_1$-$C_{20}$ alkyl, —$C_1$-$C_{20}$ heteroalkyl, —C(O)—$C_1$-$C_{20}$ alkyl, —OC(O)—$C_1$-$C_{20}$ alkyl, —C(O)O—$C_1$-$C_{20}$ alkyl, —OC(O)O—$C_1$-$C_{20}$ alkyl, —C(O)N($R^5$)—$C_1$-$C_{20}$ alkyl, —N($R^5$)C(O)—$C_1$-$C_{20}$ alkyl, —OC(O)N($R^5$)—$C_1$-$C_{20}$ alkyl, —O-aryl, —O-heteroaryl, —C(O)-aryl, —C(O)-heteroaryl, —OC(O)-aryl, —C(O)O-aryl, —OC(O)-heteroaryl, —C(O)O-heteroaryl, —C(O)O-aryl, —C(O)O-heteroaryl, —C(O)N($R^5$)-aryl, —C(O)N($R^5$)-heteroaryl, —N($R^5$)C(O)-aryl, —N($R^5$)$_2$C(O)-aryl, or —N($R^5$)C(O)-heteroaryl, —S(O)$_2$N($R^5$)-aryl, wherein each alkyl, heteroalkyl, aryl, and heteroaryl is optionally substituted by one or more $R^9$;

each $R^9$ is independently —$C_1$-$C_{20}$ alkyl, —O—$C_1$-$C_{20}$ alkyl, —$C_1$-$C_{20}$ heteroalkyl, halo, —CN, —OH, oxo, aryl, heteroaryl, —O-aryl, or —O-heteroaryl; and each $R^{14}$ is independently —$C_1$-$C_{20}$ alkyl, $C_1$-$C_{20}$ heteroalkyl, —OC(O)O$C_1$-$C_{20}$ alkyl, C(O)N($R^4$)$_2$ cycloalkyl, heterocyclyl, aryl, or heteroaryl.

2. The compound of claim 1, wherein each $Z^1$ is O.

3. The compound of claim 1, wherein $B^1$ is adenosinyl or guanosinyl, and $B^2$ is cytosinyl, thyminyl, or uracilyl.

4. The compound of claim 1, wherein each of $R^1$ and $R^2$ is independently hydrogen, halo, $OR^7$, CN, or —$C_1$-$C_{20}$ alkyl.

5. The compound of claim 1, wherein each of $X^1$ and $X^2$ is independently O.

6. The compound of claim 1, wherein each of $Y^1$ and $Y^2$ is independently O or S.

7. The compound of claim 1, wherein one of $Y^1$ and $Y^2$ is O and the other of $Y^1$ and $Y^2$ is S.

8. The compound of claim 1, wherein each of $L^1$ and $L^2$ is independently $C_1$-$C_6$ alkylene.

9. The compound of claim 1, wherein each of $R^3$ and $R^4$ is independently hydrogen, aryl, or heteroaryl, wherein aryl and heteroaryl is optionally substituted with 1-5 $R^8$.

10. The compound of claim 1, wherein $R^3$ is phenyl substituted with 1 $R^8$, and $R^4$ is hydrogen.

11. The compound of claim 1, wherein each of $R^3$ and $R^4$ is independently phenyl substituted with 1 $R^8$.

12. The compound of claim 1, wherein each of $Y^1$ and $Y^2$ is O and each of $R^3$ and $R^4$ is independently hydrogen.

13. The compound of claim 1, wherein each of $Y^1$ and $Y^2$ is independently S and each of $R^3$ and $R^4$ is independently substituted with 1 $R^8$.

14. The compound of claim 13, wherein $Y^1$ is S and $R^3$ is substituted with 1 $R^8$.

15. The compound of claim 1, wherein $R^8$ is —OC(O)-aryl, and the aryl is optionally substituted by 1-5 $R^9$.

16. The compound of claim 15, wherein $R^9$ is —O—$C_1$-$C_{12}$ alkyl.

17. The compound of claim 1, wherein $Z^2$ is —N($R^5$)—; and $R^5$ is hydrogen.

18. The compound of claim 1, wherein $L^3$ is $C_1$-$C_{20}$—alkylene, —$C_1$-$C_{20}$-heteroalkylene oligiopeptide-C(O)—, oligiopeptide-aryl-$C_1$-$C_6$-alkylene-, oligiopeptide-aryl-$C_1$-$C_6$-heteroalkylene, oligiopeptide-aryl-$C_1$-$C_6$-alklyene-C(O)—, oligiopeptide-$C_1$-$C_6$-alkylene-C(O)—, or oligiopeptide-$C_1$-$C_6$-heteroalkylene-C(O)—.

19. The compound of claim 18, wherein the oligiopeptide comprises 2 amino acid residues, 3 amino acid residues, 4 amino acid residues, 5 amino acid residues, 6 amino acid residues, 7 amino acid residues, 8 amino acid residues, 9 amino acid residues, or 10 amino acid residues.

20. The compound of claim 18, wherein $L^3$ is

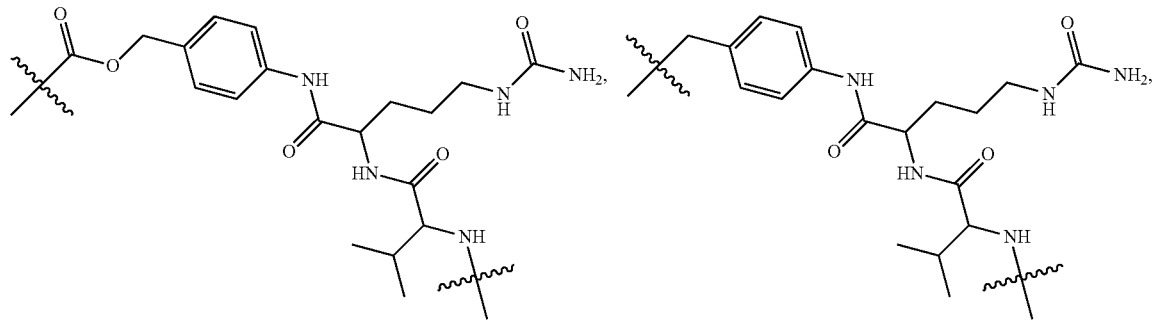

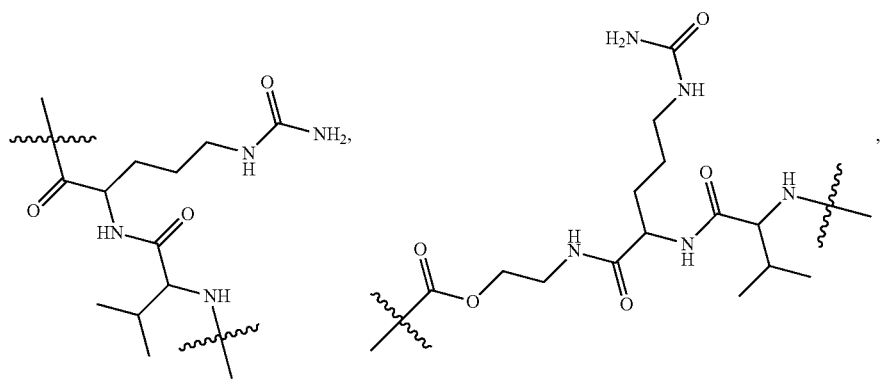

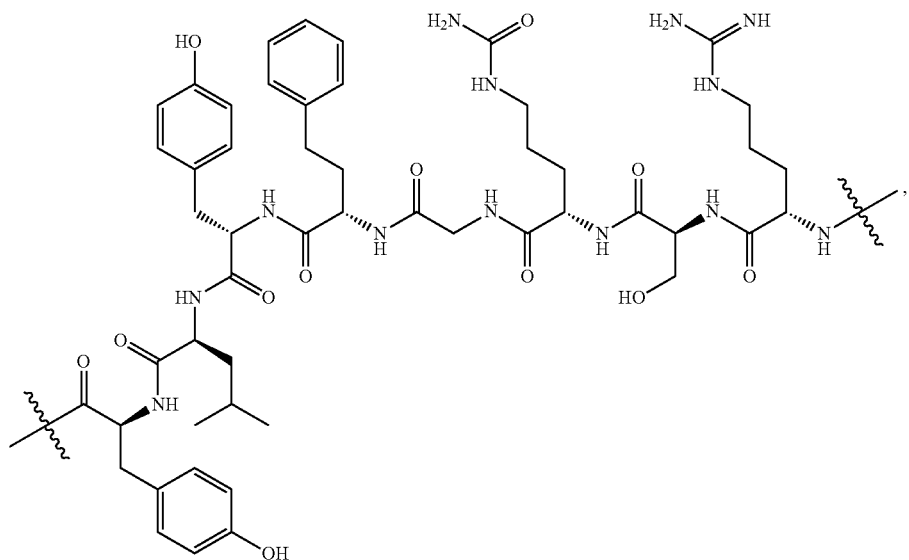

-continued

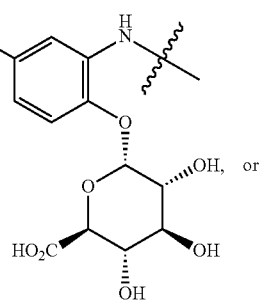

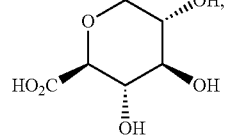

, or

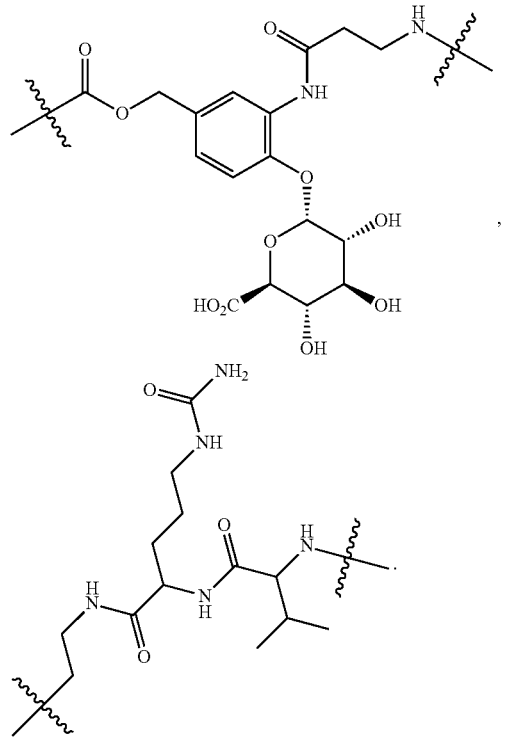

21. The compound of claim 1, wherein $Z^3$ is

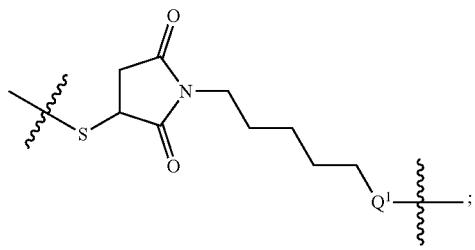

and $Q^1$ is C(O).

22. The compound of claim 21, wherein $L^4$ is absent.

23. The compound of claim 22, wherein T is absent.

24. The compound of claim 1, wherein Tm is an antibody, a hormone, a hormone derivative, folic acid, a folic acid derivative, a biotin, a small molecule, an oligopeptide, a sigma-2-ligand, or a sugar.

25. The compound claim 24, wherein the antibody is selected from the group consisting of intact polyclonal antibodies, intact monoclonal antibodies, antibody fragments, single chain Fv (scFv) mutants, multispecific antibodies, bispecific antibodies, chimeric antibodies, humanized antibodies, human antibodies, fusion proteins including an antigen determination portion of an antibody, immunoglobulin molecules including an antigen recognition site, an anti-CD22 antibody, and an anti-CD79b antibody.

26. The compound of claim 24, wherein the antibody is selected from the group consisting of muromonab-CD3, abciximab, rituximab, daclizumab, palivizumab, infliximab, trastuzumab, etanercept, basiliximab, gemtuzumab ozogamicin, alemtuzumab, ibritumomab tiuxetan, adalimumab, alefacept, omalizumab, efalizumab, tositumomab-I[131], cetuximab, bevacizumab, natalizumab, ranibizumab, panitumumab, eculizumab, rilonacept, certolizumab pegol, romiplostim, belimumab, anti-CD20, tocilizumab, atlizumab, mepolizumab, pertuzumab, tremelimumab, ticilimumab, inotuzumab ozogamicin, aflibercept, catumaxomab, pregovomab, motavizumab, efumgumab, Aurograb, raxibacumab, and veltuzumab.

27. The compound of claim 1, wherein the compound is selected from the following table:

| Number | Compound |
|---|---|
| 1 | 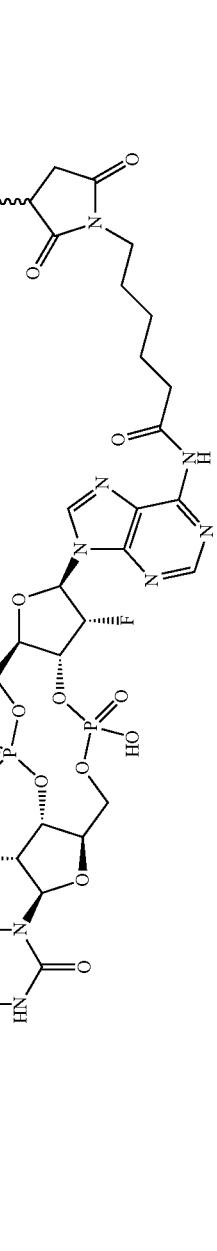 |
| 2 | 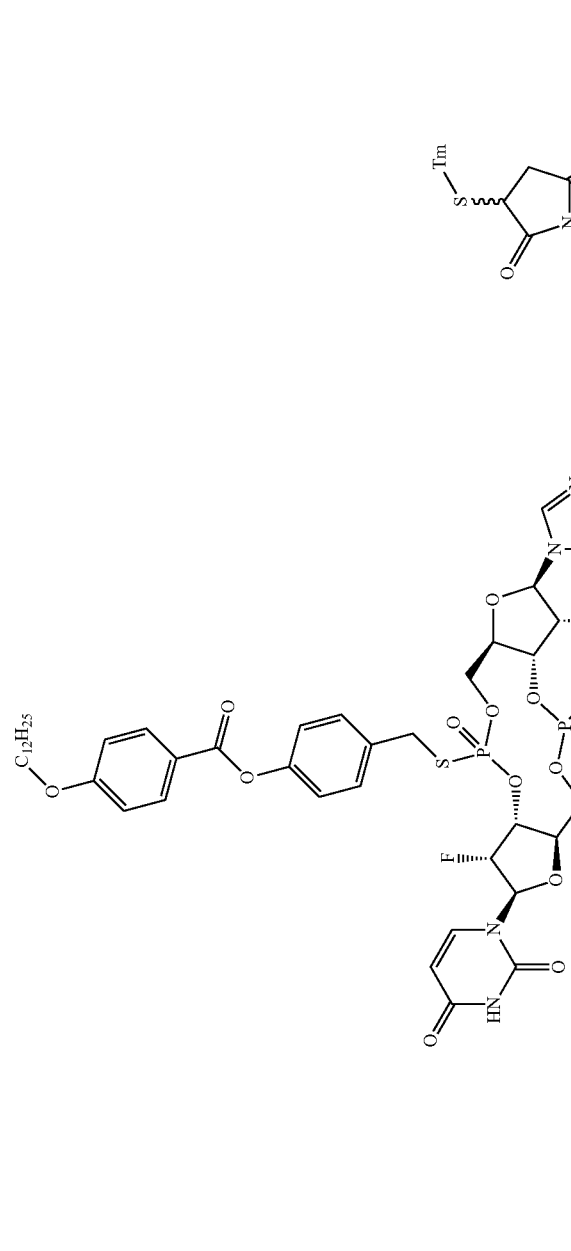 |

-continued
| Number | Compound |
|---|---|
| 3 | 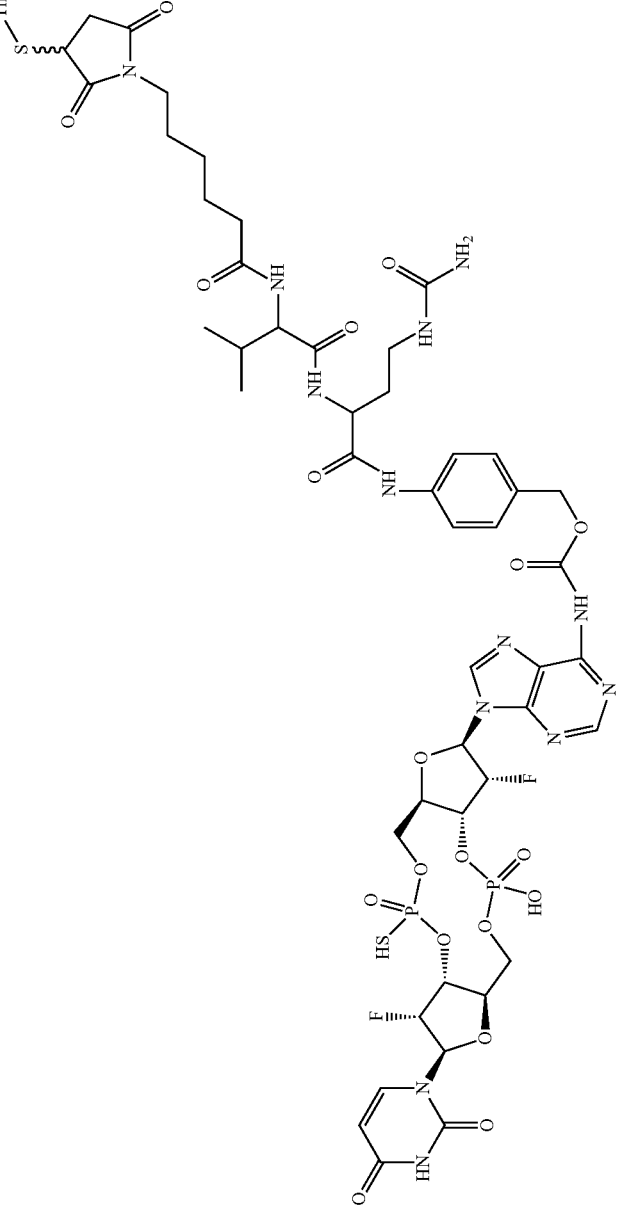 |

| Number | Compound |
|---|---|
| 4 | 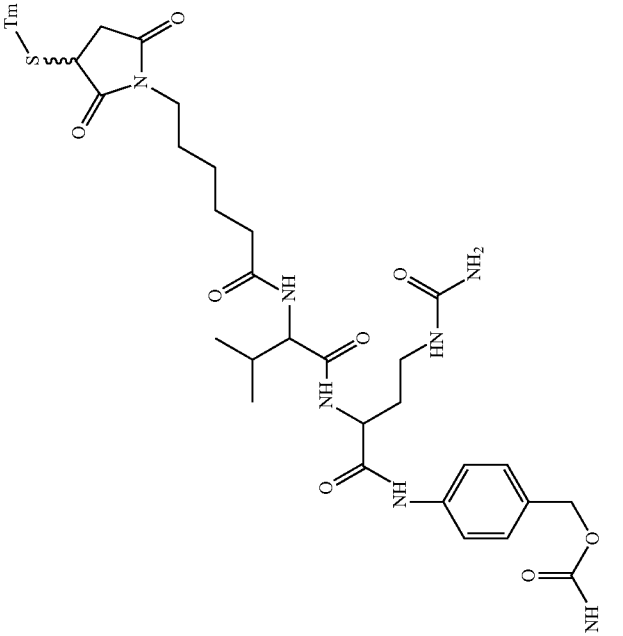 |
| 5 | 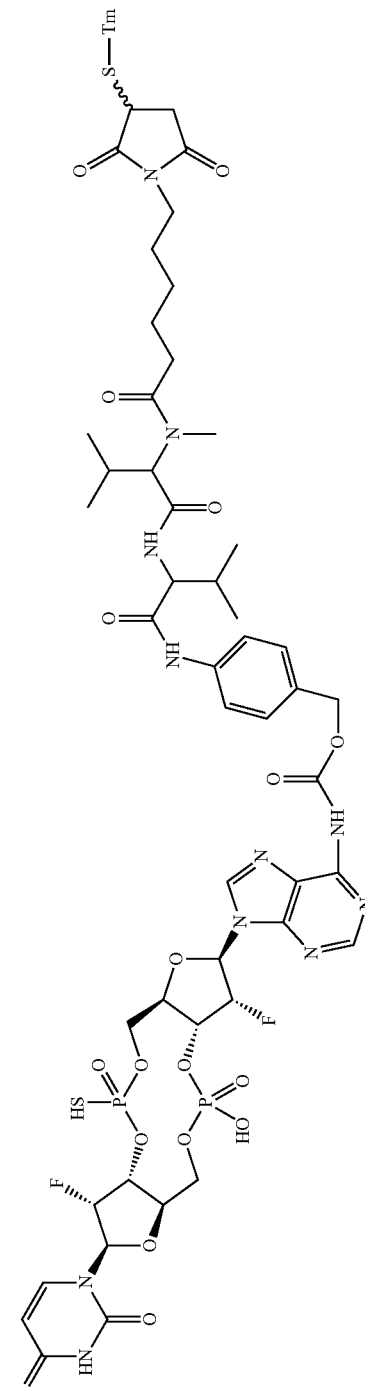 |

| Number | Compound |
|---|---|
| 6 | 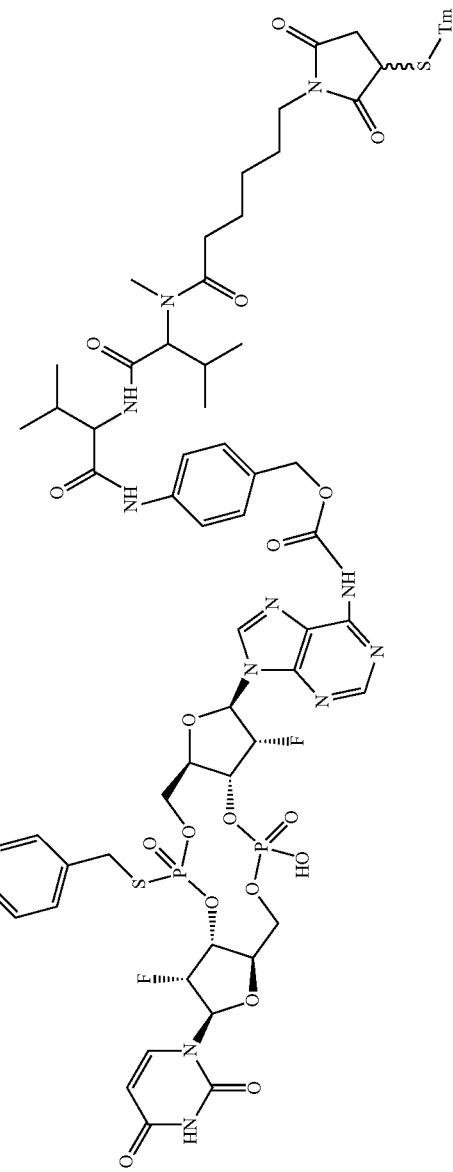 |

-continued
| Number | Compound |
|---|---|
| 9 | 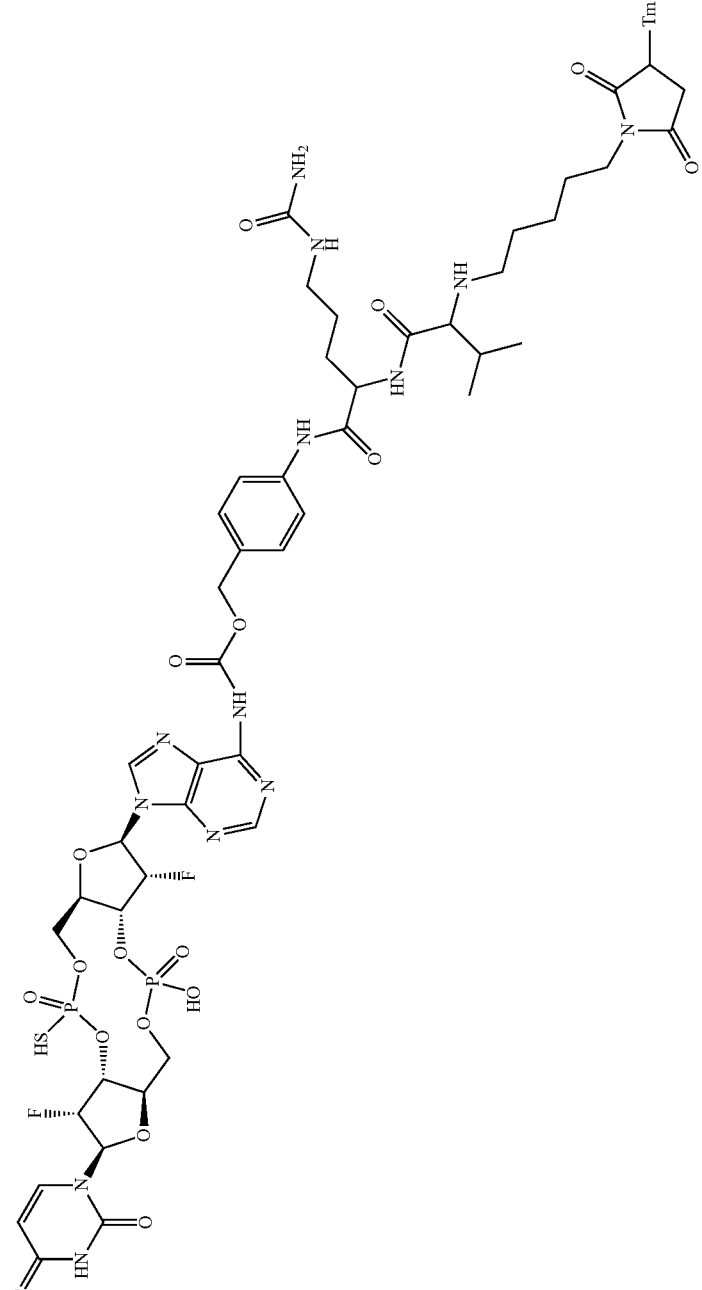 |

| Number | Compound |
|---|---|
| 12 | 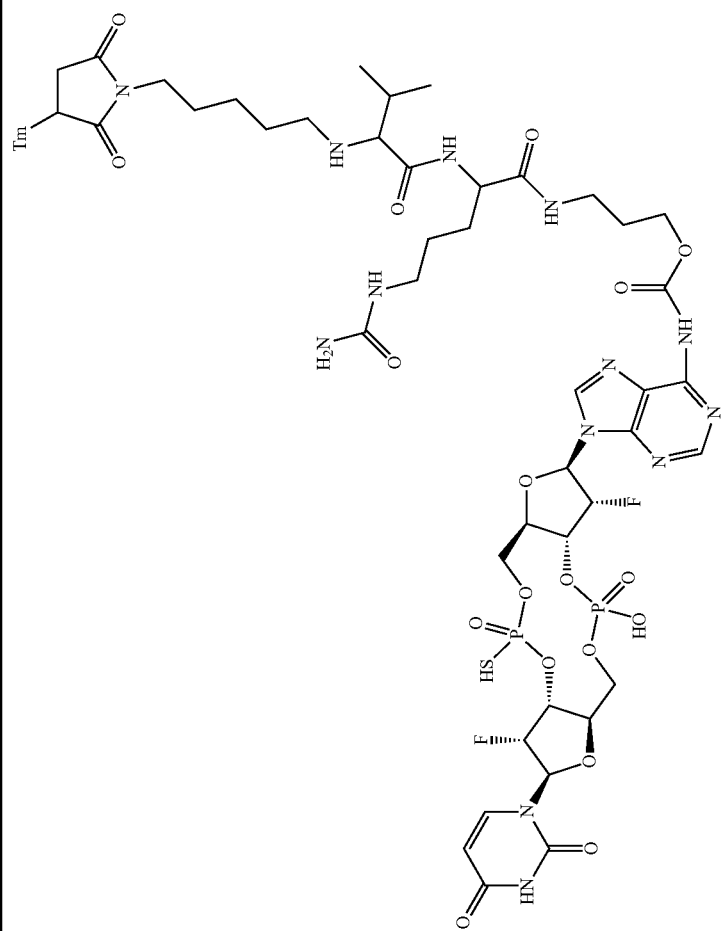 |

-continued
| Number | Compound |
|---|---|
| 15 | 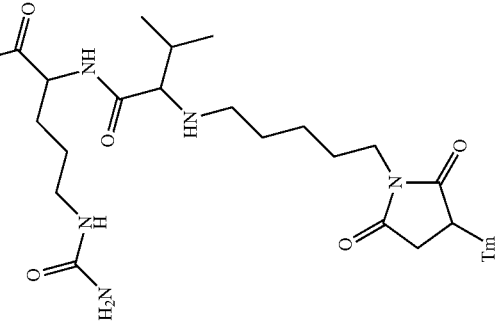 |

-continued
| Number | Compound |
|---|---|
| 18 | 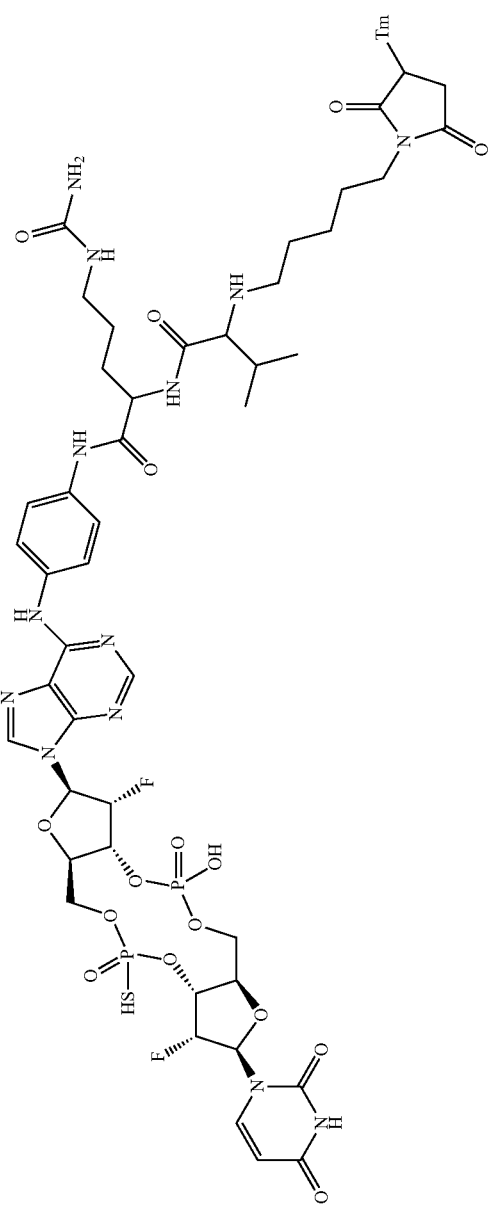 |

| Number | Compound |
|---|---|
| 20 | 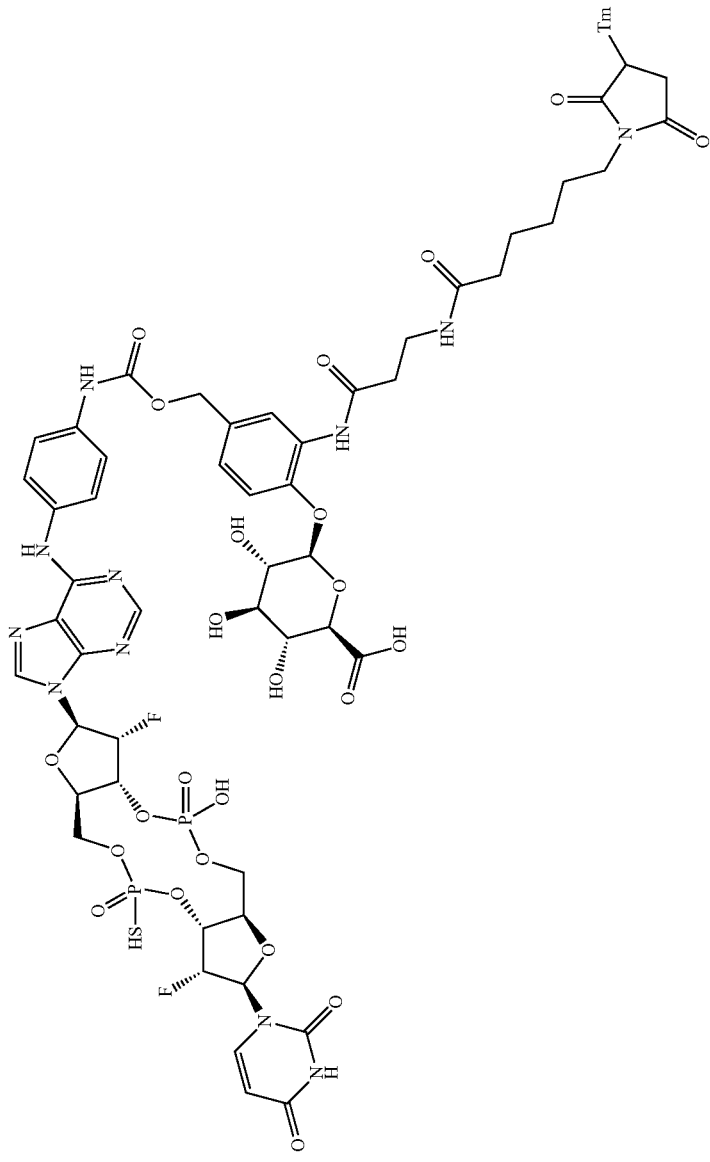 |

-continued
| Number | Compound |
|---|---|
| 22 | 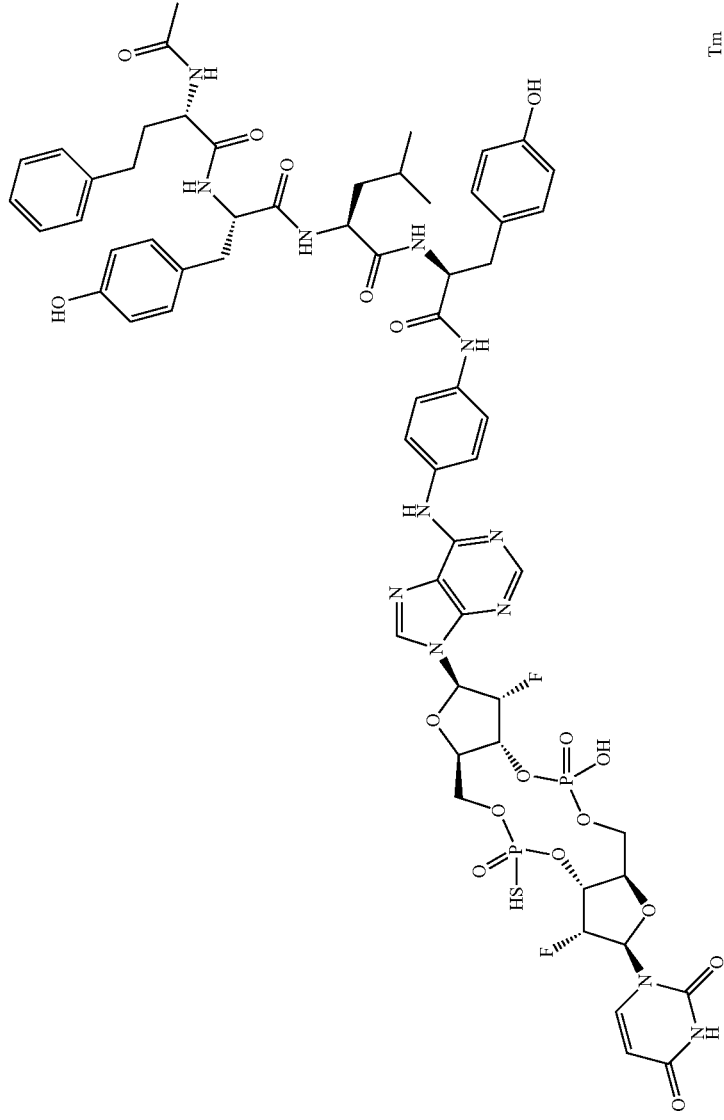 | or a pharmaceutically acceptable salt thereof; wherein Tm is a targeting moiety.

28. A method of alleviating a cancer in a subject in need thereof, comprising administering to the subject a therapeutically effective amount of a compound of claim 1 or a pharmaceutically acceptable salt thereof.

29. A method of inducing the expression of a pattern recognition receptor (PRR) for immune-modulation in a subject, comprising administering to the subject a therapeutically effective amount of a compound of claim 1 or a pharmaceutically acceptable salt thereof.

30. A method of inducing an immune response in a subject, comprising administering to the subject a therapeutically effective amount of a compound of claim 1 or a pharmaceutically acceptable salt thereof.

31. A method of alleviating a microbial infection or a viral infection in a subject in need thereof, comprising administering to the subject a therapeutically effective amount of a compound of claim 1 or a pharmaceutically acceptable salt thereof.

\* \* \* \* \*